US012606830B2

(12) United States Patent (10) Patent No.: US 12,606,830 B2
Kosak et al. (45) Date of Patent: Apr. 21, 2026

(54) PROTECTED ANTIBODY-DRUG AND APTAMER-DRUG CONJUGATES

(71) Applicants: Kenneth Michael Kosak, Salt Lake City, UT (US); Matthew Kenneth Kosak, Corona, CA (US)

(72) Inventors: Kenneth Michael Kosak, Salt Lake City, UT (US); Matthew Kenneth Kosak, Corona, CA (US)

( * ) Notice: Subject to any disclaimer, the term of this patent is extended or adjusted under 35 U.S.C. 154(b) by 200 days.

(21) Appl. No.: 16/729,297

(22) Filed: Dec. 27, 2019

(65) Prior Publication Data

US 2021/0198671 A1      Jul. 1, 2021

(51) Int. Cl.
| | |
|---|---|
| *C12N 15/115* | (2010.01) |
| *C07K 16/00* | (2006.01) |
| *C12Q 1/68* | (2018.01) |

(52) U.S. Cl.
CPC ............ *C12N 15/115* (2013.01); *C07K 16/00* (2013.01); *C07K 2318/00* (2013.01)

(58) Field of Classification Search
None
See application file for complete search history.

*Primary Examiner* — Sean Mcgarry

(57) ABSTRACT

This invention is a new strategy using a rational design for a "flexible" drug carrier composition, meaning that it provides drug release with a conformational change under specific conditions. Said carrier in its "closed" conformation, contains a drug wherein significant release of Said drug from its carrier only occurs during or after said conformational change, such as when a ligand binding domain is removed. Said carrier can then undergo a molecular, conformational change to an "open" form. The term "Allosteric Releasem" is inspired by this inventive concept.

2 Claims, 5 Drawing Sheets

Specification includes a Sequence Listing.

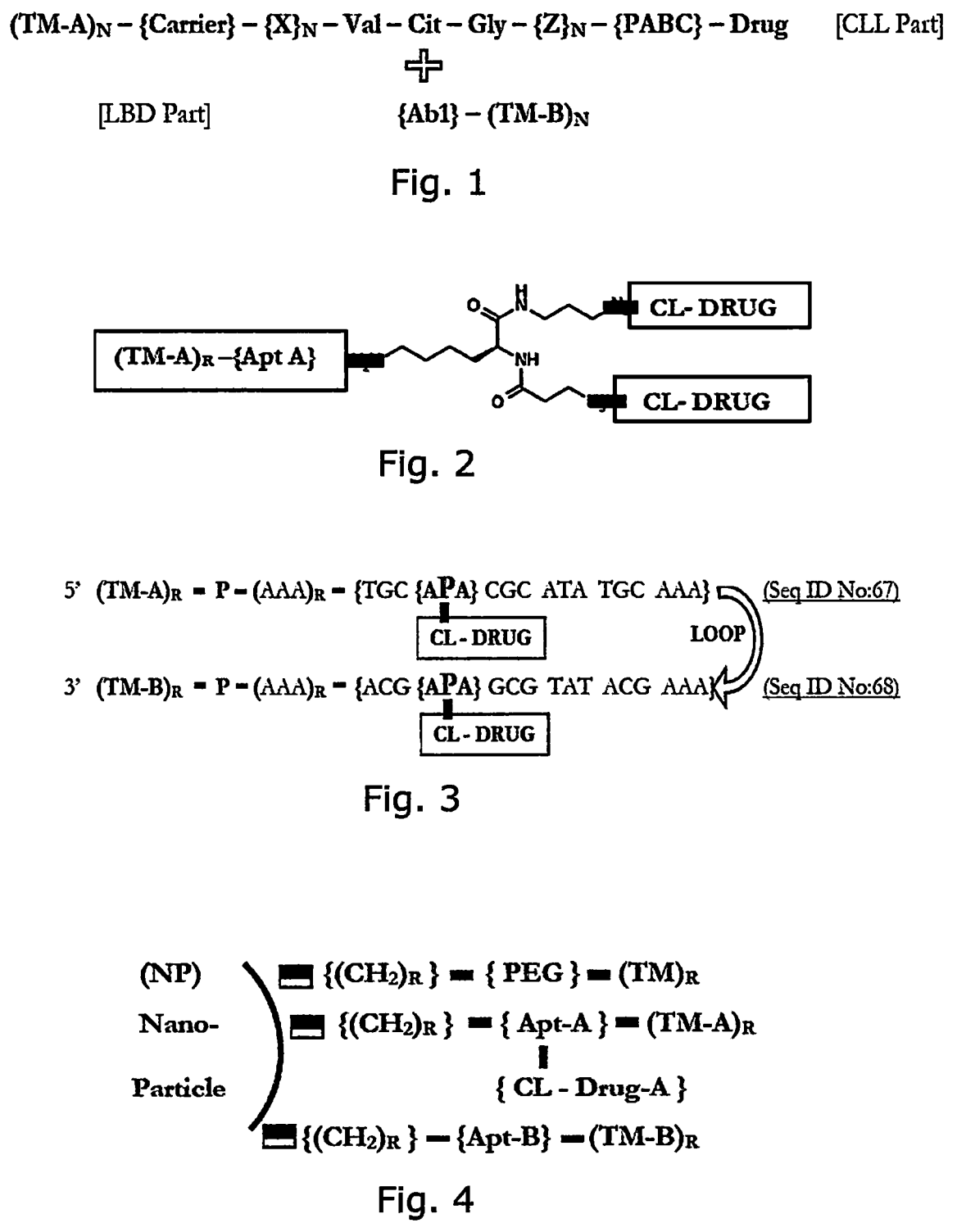

(TM-A)$_N$ – {Carrier} – {X}$_N$ – Val – Cit – Gly – {Z}$_N$ – {PABC} – Drug          [CLL Part]

+

[LBD Part]                              {Ab1} – (TM-B)$_N$

5'  (TM-A)$_R$ – P – (AAA)$_R$ – {TGC {APA} CGC ATA TGC AAA}          (Seq ID No:67)

CL - DRUG          LOOP

3'  (TM-B)$_R$ – P – (AAA)$_R$ – {ACG {APA} GCG TAT ACG AAA}          (Seq ID No:68)

CL - DRUG

Fig. 3

(NP)          {(CH$_2$)$_R$} – { PEG } – (TM)$_R$

Nano-          {(CH$_2$)$_R$} – { Apt-A } – (TM-A)$_R$

{ CL - Drug-A }

Particle

{(CH$_2$)$_R$} – {Apt-B} – (TM-B)$_R$

Fig. 4

(Seq ID No:138)

5' (TM-A)ᴿ ─(CH₂)ᴿ ─ P ─ (AAA)ᴿ ─{TCC CGC AAA TTT ACG GCG TAT AAA}

NCS - CL - DRUG

TM

3' (TM-B)ᴿ ─(CH₂)ᴿ ─ P ─ (AAA)ᴿ ─{AGG GCG TTT AAA TGC CGC ATA AAA}

(Seq ID No:139)

Fig. 5

5' (TM-A)ᴿ ─ P ─ (AAA)ᴿ ─{TCC CPC AAA TTT ACG GCG TAT AAA} (Seq ID No:140)

CL - DRUG

TM

3' (TM-B)ᴿ ─ P ─(AAA)ᴿ ─{AGG GCG TTT AAA TGC CGC ATA AAA} (Seq ID No:139)

Fig. 6

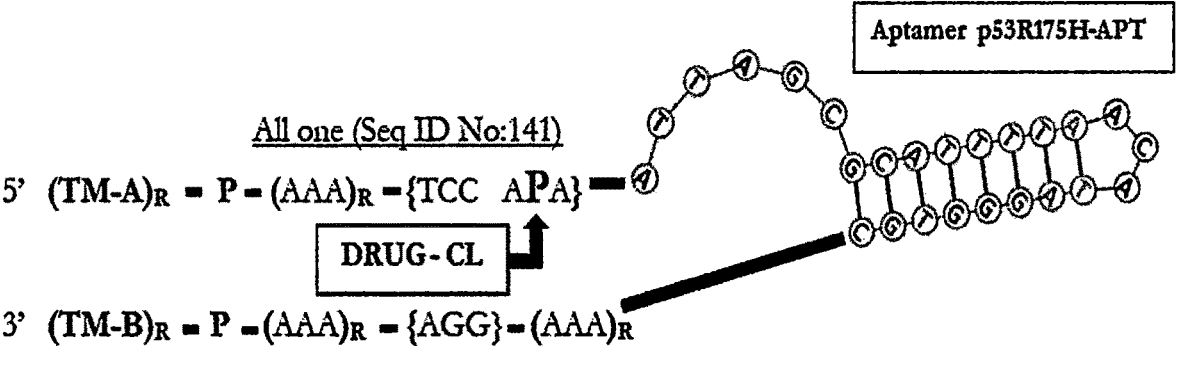

Aptamer p53R175H-APT

All one (Seq ID No:141)

5' (TM-A)ᴿ ─ P ─(AAA)ᴿ ─{TCC APA}─ A

DRUG - CL

3' (TM-B)ᴿ ─ P ─(AAA)ᴿ ─ {AGG}─(AAA)ᴿ

Fig. 7

5' (TM-A)ᴿ ─ P ─(AAA)ᴿ ─ {TCC CPC AAA TTT ACG GCG TAT AAA} (Seq ID No:138)

CL - DRUG

LOOP

CL - DRUG

3' (TM-B)ᴿ ─ P ─(AAA)ᴿ ─ {AGG GCG TTT AAA TGC CGC ATA AAA} (Seq ID No:139)

Fig. 8

CL - DRUG (TM-C)ᴿ

G·G·G·G·G·G·X·G·G·G·T·T
X·C·C·C·C·C·C·X·C·C·T·G    (Seq ID No:148)
5'

(TM-A)ᴿ

CL - DRUG

{APTAMER}

3'

3'

■ {PEG}

CL - DRUG (TM-C)ᴿ

G·G·G·G·G·X·G·G·G·G·T·T
X·C·C·C·C·C·C·X·C·C·T·G    (Seq ID No:149)
5'

(TM-B)ᴿ    CL - DRUG

CL-DRUG (TM-D)ᴿ

(TM-C)ᴿ

(TM-F)ᴿ

CL - DRUG

CL-DRUG (TM-E)ᴿ

CL - DRUG (TM-A)ᴿ

{PEG}    (TM-B)ᴿ    CL - DRUG

PROTECTED ANTIBODY-DRUG AND APTAMER-DRUG CONJUGATES

This is a Continuation in Part (CIP), and Nonprovisional U.S. Patent Application of Provisional U.S. Patent Application No. 62/786,340, filed Dec. 29, 2018, (herein called App. 62/786,340), the entire contents, including suitable methods and examples, and references therein which are hereby incorporated by reference as if fully set forth herein. All patent applications, patents, and publications, including supplementary materials, and additional references therein, that are cited herein, are hereby incorporated herein by reference in their entireties, except for any conflicting definitions, subject matter disclaimers or disavowals, and except to the extent that the incorporated material is inconsistent or in conflict with the express disclosures herein, in which case the language in this disclosure controls.

For this invention, certain useful compositions and synthesis methods, and all categories of active agents, ligands, all intercalators of nucleic acids and peptides, any antibodies, any nucleic acids, including carrier nucleic acid compositions, peptide nucleic acids (PNA) and derivatized nucleic acids, splicing RNA (spRNA), DNAzymes, any polymers, targeting moieties, target substances including cancer cells, disease microorganisms and biomarkers, coupling agents and functional groups, are all suitably modified as needed. All compositions that would be useful for this invention after suitable modification, defined herein, including crRNAs, sgRNAs, any CRISPR proteins and compositions, any zinc finger proteins and compositions, any TALEN proteins and compositions and any suitable derivatives thereof.

REFERENCE TO SEQUENCE LISTING

The instant application contains Sequence ID numbers, and a Sequence Listing which has been submitted in computer readable form (CRF), in ASCII format, file name: "AbDrugSeq16_729_297_Feb24_ST25.txt", and is hereby incorporated by reference in its entirety for all purposes.

DESCRIPTION OF THE DRAWINGS

FIG. 1 is: Example Diagram 1. CLL COmposition With a Valine-Citrulline-Glycine Cleavabie Linkage Sequence With Optional Moieties.

FIG. 2 is: Example Diagram II-A. Branched Cleavabie Linkage.

FIG. 3 is: Example Diagram V-A. Folded Drug Carrier Aptamer Composition and Structural LOOP.

FIG. 4 is: Example Diagram VI-A. Nanoparticle and Aptamer Carrier Composition.

FIG. 5 is: Example Diagram VIII-A. Drug Carrier Aptamer with Noncovalently CoupledNCS-CL-Drug.

FIG. 6 is: Example Diagram IX. Carrier Aptamer Hairpin with terminal (TM-A)R and (TM-B)R and TM LOOP.

FIG. 7 is: Example Diagram IX-A. Carrier Aptamer Hairpin with (TM-A)R and (TM-B)R and Aptamer p53R175H-APT as TM LOOP.

FIG. 8 is: Example Diagram X. Carrier Aptamer Hairpin with (TM-A)R and (TM-B)R and Structural LOOP.

TECHNICAL FIELD OF THE INVENTION

Figure 9:
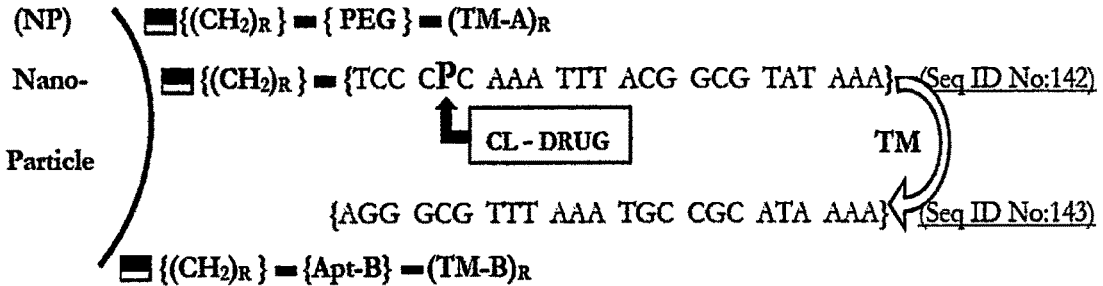
FIG. 9 is: Example Diagram XI. Nanoparticle with Hairpin "Zipper" Aptamer with Optional TM-LOOP.
Figure 10:
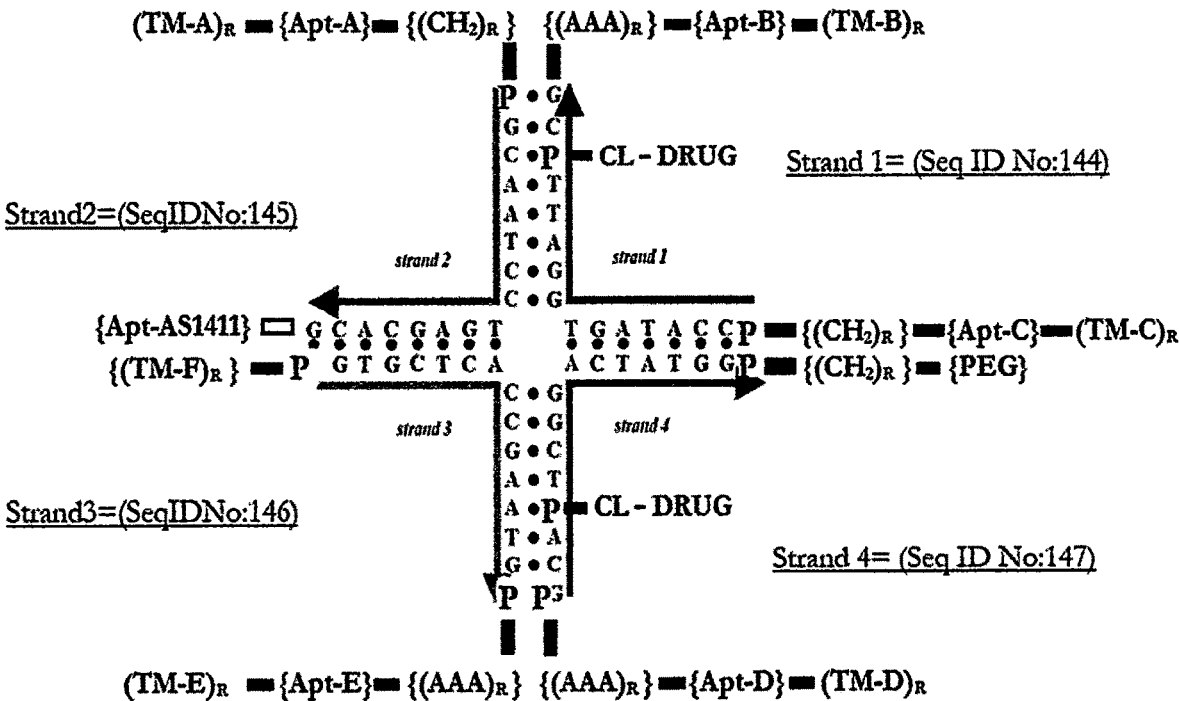
FIG. 10 is: Example Diagram XII. Holliday Carrier NanoParticle with Zipper Motifs.
Figures 11, 12:
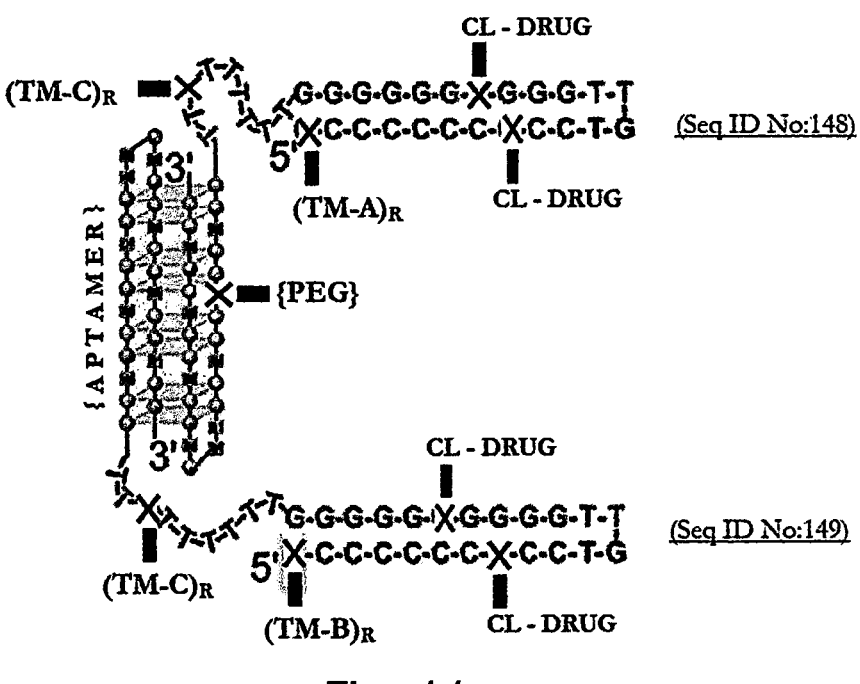
FIG. 11 is: Example Diagram XIII. Carrier Aptamer Quadruplex Composition with Zipper Extensions.
FIG. 12 is: Example Diagram XIV. Carrier Aptamer Tetrahedron Composition with Zipper Motifs.
Figure 13:
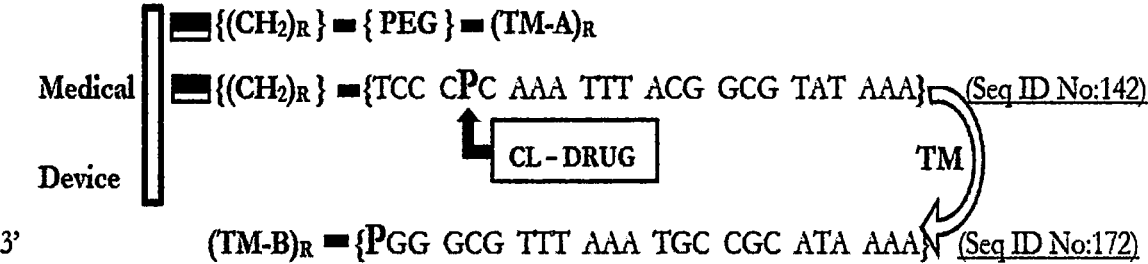
FIG. 13 is. Example Diagram XV. Device Coating Composition Hairpin "Zipper" Aptamer with Optional TM-LOOP.
Figure 14:
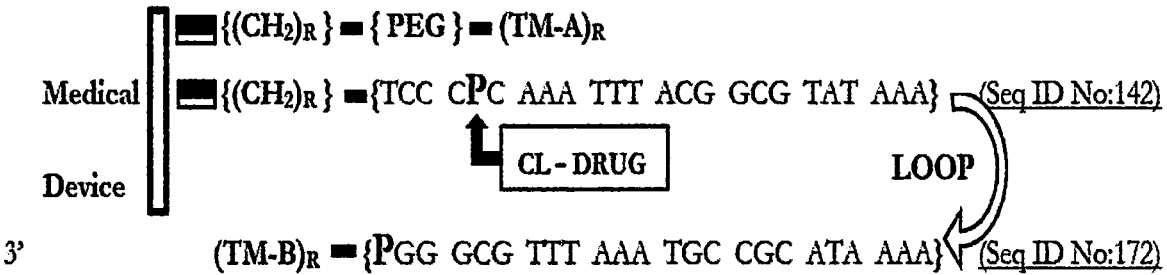
FIG. 14 is: Example Diagram XVI. Device Coating Composition Hairpin "Zipperf" Aptamer with Optional LOOP.

This invention discloses and claims new compositions that are in the field of nanomedicine compositions and drug delivery compositions. This invention comprises drugs or "active agents", defined herein, coupled with specific molecular, or nano-sized substances, compositions, or drug carrier, molecular compositions ("carriers"), not meant to include solvents, solubilizers, excipients, etc., used in certain formulations. This invention includes antibodies and aptamers and molecular coatings for medical devices, for delivering and releasing said active agents (i.e. drugs), to the desired target cells, tissues or organs for pharmaceutical or agricultural use. This invention is also applicable to in vitro diagnostic testing and research use. The compositions of this invention include carrier substances defined herein with active agents, defined herein coupled through covalent, cleavable linkages or by noncovalent coupling between said active agent and said carrier defined herein. The compositions can also contain covalently coupled said active agents that also function as ligands with noncovalent coupling with a ligand binding domain defined herein.

Said compositions of this invention can include at least one targeting moiety or biorecognition molecule, defined herein, capable of binding to its intended target substance. The compositions can include various carrier substances to which active agents are coupled that can include any suitable aptamers and/or proteins including antibodies, polypeptides, nucleic acids, polysaccharides, synthetic polymers, micelles, nanoparticles and other substances known in the art for carrying and releasing the active agents into the body for therapeutic effect. The invention also discloses methods for preparing and using said compositions.

BACKGROUND OF THE PRIOR ART

Various substances, including antibodies are coupled with active agents and used as drug carriers in various therapies such as treatment for cancer and other diseases. In the prior art, said active agents are released unintentionally from a variety of carriers primarily through chemical means that includes catalytic or enzymatic degradation or cleavage of linkages between the active agent and the carrier.

Apparently, nothing in the prior art discloses or suggests protecting said linkages through specific noncovalent binding that provides protection due to steric hindrance or inhibition, as is disclosed and claimed in the present invention.

A major purpose of this invention is to provide an additional level of protection in the delivery and release of active agents. Surprisingly, it is found that the embodiments of the present invention provide a new drug stability that has additional benefits. There is less risk of toxicity from unintended release of the active agent which thereby provides more specific and targeted release at the active site. It will be apparent that said compositions provide other unexpected advantages such as higher specific activity and cost savings.

SUMMARY DISCLOSURE OF THE INVENTION

This invention is a new strategy using a rational design for a "flexible" drug carrier composition, meaning that it provides drug release with a conformational change under specific conditions. Said carrier in its "closed" conformation, contains a drug wherein significant release of said drug from its carrier only occurs during or after said conformational change, such as when a ligand binding domain is removed. Said carrier can undergo a molecular, conformational change to an "open" form. The term "Mechanomed™" is inspired by this inventive concept. This invention discloses and claims said compositions that include a "Force Responsive Carrier™" (FRC), designed to deliver and release active agents. This invention comprises active agents coupled with specific nano-sized, or molecular-sized, carrier substances for delivering and releasing said active agents (i.e. drugs), to the desired target cells, tissues or organs in vivo for pharmaceutical or agricultural use.

Said closed conformation of said carrier contains structurally, various substances that provide a type of steric molecular protection, defined herein. In some embodiments, said active agent is suitably covalently coupled through a suitable linkage, to said carrier composition. And said active agent and/or said linkage is suitably sequestered or sterically hindered from being released from the carrier composition.

A major advantage of this invention is to provide a highly specific, targeted release of active agent(s). For this invention, "Force Responsive Release™" or "Allosteric Release™") is defined as the specific release of active agents from said "flexible" carrier composition.

Said term "flexible" is also applicable to certain ligands or active agents that provide binding sites for other moieties such as a "Ligand Binding Domain" (LBD), defined herein. Said flexible carrier can change from a closed form to an open form, defined herein. In the case of a covalently coupled active agent, the linkage between the flexible carrier and active agent is then exposed and then can be chemically cleaved, allowing the release of the active agent.

For certain embodiments of this invention, including drug carrier aptamers, drug carrier antibodies, (and other scaffolds, defined herein) of this invention, said carrier compositions are designed to provide Allosteric Release™, as defined herein. Said Allosteric Release™ is defined as significant release of an active agent (i.e. drug) from said carrier, defined herein, only after specific binding of said LBD, defined herein, is reversed. Without imposing limitations on the scope of this invention, the mechanism that causes said conformational change is brought about through binding forces known in the art of allosteric effects.

Said carriers can also function directly or indirectly as a targeting moiety ("TM"), or specific binding moiety, defined herein, that is incorporated into the compositions of this invention. The specific binding function and the drug release function are linked in a "cause and effect" relationship, but these events can occur some distance from each other. Therefore, the term "Allosteric Release™", is inspired by this invention.

Precision Lethality™.

When applicable and/or suitable, a major goal of this invention for employing said active agents, defined herein, will also provide a suitable means for overcoming resistance to treatment. It is well known in the art of treating disease, that development of resistance requires some members of a targeted population to survive and reproduce after receiving a "sub-lethal" dose of active agent.

Therefore, said goal of this invention is to provide, where possible, a "Precision Lethality™" (or PL), described herein. Said Precision Lethality™ means, for the purposes of this invention, that highly specific identification, and lethal targeting of specific organisms (i.e. vermin, or any disease organisms or especially cancer cells), can be provided by this invention. Therefore, ideally, one hundred percent (100%), of every said targeted organism or cell or virus is killed and/or rendered incapable of reproduction or further growth when exposed to a suitable Precision Lethality™ carrier molecule or nanoparticle of this invention.

INDUSTRIAL APPLICABILITY AND USE

These compositions containing active agents are for the pharmaceutical, agricultural and research markets. The compositions of this invention are useful for administration to people or other animals in a suitable dosage regimen (i.e. "therapeutic dose"), by any suitable route such as orally; by any injection route (i.e. intravenous, subcutaneous, intramuscular, intracranial, etc.); by pulmonary (i.e. inhalation), anal, vaginal or urethral route; through the eye, ear, nose or throat and topically through the skin. Administration can also include the use of any suitable drug delivery device, delivery patch, composition or vehicle that facilitates delivery of the compositions of this invention into the body. The compositions of this invention are also useful for administration to people, other animals and plants (i.e. food crops) against any disease organisms (i.e. viruses, bacteria, fungi, parasites and arthropods).

BEST MODES FOR CARRYING OUT THE INVENTION

Terms and Definitions

For the purposes of disclosing this invention, certain words, phrases and terms used herein are defined below. It will be understood in the art of drug carriers coupled to targeting moieties and active agents, that there are limitations as to which derivatives, coupling agents or other substances can be used with targeting moieties and active agents to fulfill their intended function. The terms "suitable", "suitably modified" and "appropriate" refer to derivatization and/or synthesis methods known to those skilled in the art for performing the described reaction, or synthesis and/or other procedures needed to provide the intended reaction, or composition and/or intended function of this invention. It will also be understood in the arts of active agents, biochemistry and drug carriers that there are many substances defined herein that, under specific conditions, can fulfill more than one function. Therefore, if they are listed or defined in more than one category, it is understood that each definition depends upon the conditions of their intended use.

Wherein certain definitions comprise a list of substances preceded by any grammatical form of the term "includes", such substances are presented as examples taken from a group of substances known in the art to fit the said definition and the invention is not limited to the examples and references given. All references listed herein, and references therein, are incorporated into this invention by reference, including active agents, carrier substances, other useful substances, nucleic acid sequences, peptide sequences and methods for their synthesis or use. All said definitions include disclosures and all references from previously filed App. 62/786,340.

Pharmaceutical.

For the purposes of this invention, pharmaceutical or "pharmaceutical use" is defined as being limited to substances, including active agents, defined herein, that are useful or potentially useful in therapeutic or prophylactic applications or therapeutic dose. Said compositions and "pharmaceutical active agents" or "therapeutic active agents", are used against diseases or disorders in humans, or any other vertebrate animals and in plants, especially plants of economic value. The most preferred substances defined as pharmaceutical are active agents and/or compositions useful against viral, bacterial, fungal, protozoan, parasitic and other disease organisms, against cancers, autoimmune diseases, genetic diseases, heart diseases, neurological diseases and other diseases or disorders in humans and other vertebrates. Generally, but not necessarily, pharmaceutical substances are also biocompatible. Biocompatible is defined here to mean substances that are suitably designed to be generally non-immunogenic, non-antigenic and will cause minimum undesired physiological reactions. They may or may not be degraded biologically and they are suitably "biologically neutral" for pharmaceutical applications due to suitably low non-specific binding properties.

Nanomechanical™ Force or Nanoforce™.

For certain embodiments of this invention a physical change in said composition from a closed conformation to an open conformation, as defined herein, is the result of sufficient physical, biological, molecular or macromolecular mechanical force or energy, that can include a binding force, a pulling force, stretching force, shearing force or pushing force applied to a suitable composition or carrier and/or active agent over a suitable distance. Said force applied to said carrier causes a suitable amount of movement in said carrier that can include flexing, stretching, unfolding, unzipping, uncoiling, twisting, rotating, bending, shifting, separation, compressing and/or combinations thereof, of the carrier's conformation or shape. For the purposes of this invention, said physical, molecular, allosteric or macromolecular mechanical force over a suitable distance, is defined as a Nanoforce™ that can occur when said specific binding of said LBD with said ligand has reversed.

Determining Nanomechanical™ Force or Nanoforce™.

In the art of measuring molecular forces, it is already known, or it can be determined empirically, how much force, or Nanoforce™, is needed (at suitably applied rates and temperature), to unbind, unfold or unzip or open various flexible molecular and nano-structure carriers useful in this invention. In certain embodiments of this invention, said Nanoforce™ is suitably employed to separate, unbind or unfold certain moieties of this invention that are bound or coupled noncovalently, defined herein.

Said measurements are made through the use of atomic force microscopy (AFM), atomic force-based spectroscopy, optical tweezers, x-ray crystallography, NMR and other methods. The forces reported in the art are generally described in piconewtons (pN), wherein the force needed is usually inversely proportional to the rate of application. The distances travelled (i.e. stretching distance) are usually reported in angstroms to nanometers. Therefore, without putting limitations upon this invention, it is also known, or it can similarly be determined, how much of said Nanoforce™ is needed to release said active agent from said compositions of this invention. Similarly, it is also known, or it can be determined, how much movement, in terms of distance, is needed to physically change the flexible carriers of this invention from a suitably closed form to a suitably open form.

Nucleic Acids.

For the purposes of this invention, "nucleic acids" (NA), includes all "derivatized nucleic acids" defined herein, and "nucleic acid carrier compositions" preferably "carrier nucleic acid" (Carrier NA), defined herein and includes their use in any compositions and examples disclosed herein. All said definitions for all nucleic acids and derivatives hereby include disclosures and all references from previously filed Provisional App. 62/786,340.

Said nucleic acids include any oligonucleotides (ON) and any oligodeoxynucleotides (ODN), and are also defined as classes of substances useful as "flexible carrier nucleic acids" (Flexible Carrier NA), in their flexible forms (including "backbone derivatized"), defined herein. Said nucleic acids are also preferred as targeting moieties (TM), defined herein, such as aptamers and under suitable conditions, in this invention, can function as both a carrier aptamer and as a TM aptamer. Said nucleic acids are also preferred, under suitable conditions, as active agents, suitable for their intended purpose. Preferred nucleic acids are any sense and antisense NA that include phosphodiester antisense ON and antisense ODN. For the purposes of this invention, said nucleic acids are suitably categorized.

Preferred categories of said nucleic acids are any "backbone derivatized" oligonucleotides or oligodeoxynucleotides where the sugar-phosphate "backbone" has been derivatized or replaced with "backbone analogues" which include phosphorothioate (PS), phosphorodithioate, phosphoroamidate, alkyl phosphotriester, or methyl-phosphonate linkages or other "backbone analogues". Such "backbone derivatized" oligonucleotides or oligodeoxynucleotides include those with non-phosphorous backbone analogues such as sulfamate, 3'-thioformacetal, methylene (methylimino) (MMI), 3'-N-carbamate, or morpholino carbamate.

Preferred categories of said nucleic acids also include mixed backbone derivatized, capped nucleic acids, hybrid nucleic acids, peptide nucleic acids (PNA), nucleotide mimics or co-oligomers like phosphoric acid ester nucleic acids (PHONA)s, triplex-forming nucleic acids and including nucleic acids capable of forming a nucleic acid "zipper" to form said flexible carrier or scaffold, defined herein, with specific DNA and/or RNA segments.

Flexible Drug Carrier Nucleic Acid (NA) Substances.

Preferred flexible drug carrier nucleic acids (Carrier NA) in this invention include any suitable nucleic acid, or nanoparticle (NP), as defined herein. In some embodiments, preferred Carrier NAs include RNA and/or DNA strands used in a flexible carrier composition that have suitably included, complementary base sequences that can produce an RNA and/or DNA duplex (i.e. nucleic acid "zipper") Any suitable complementary nucleic acid ("base") sequences can be substituted, added or subtracted in said zipper strands to provide the desired melting temperature and the desired binding affinity between said strands. Included within said Carrier NA is a suitable sequence of nucleic acids (i.e. 2 or more) or nucleic acid strands that can include oligonucleotide (ON), oligodeoxynucleotide (ODN), mixed backbone ON or ODN, or chimeric nucleic acids, backbone derivatized nucleic acids, or with LNA, or with PNA, or triplex-forming nucleic acids, or combinations of these defined herein, wherein some of the sequences are complementary to each other. Said carrier nucleic acid may contain structural "stems" "loops" and "bulges" known in the art, as needed and may also be suitably coupled, covalently or noncovalently as defined herein, to one or more active agents.

Upon hybridization, said complementary sequences can form a "closed" nucleic acid duplex carrier "zipper" capable of carrying one or more active agents, or intercalators, as defined herein. Said active agents are covalently or noncovalently coupled, as defined herein, to said zipper sequences so that they are suitably prevented from being released in their closed form.

One or both of the complementary nucleic acid strands (NA Zippers), can also include nucleic acids that provide a specific binding sequence, such as a "loop", that functions as a targeting moiety (TM), such as an aptamer. And/or said NA zipper may also contain one or more antibodies as targeting moieties covalently coupled to one or both of said strands.

Another preferred embodiment of this invention, under suitable conditions, is any suitable, single nucleic acid strand (i.e. aptamer), used as the flexible carrier, wherein part of said single strand aptamer has two complementary sections that can fold over to form a loop, with said complementary sections capable of hybridizing to form said zipper as a binding domain for any suitable active agent or NCS, defined herein. And said loop also structurally functions as a specific targeting moiety or TM, defined herein, wherein binding of said TM produces sufficient unfolding force to release said active agent.

Active Agents (AA).

For all embodiments of this invention, preferred, useful active agents (AA or "Drug"), include "pharmaceutical active agents" or "therapeutic active agents", defined herein, and those that are suitably modified and/or derivatized as needed for covalent or noncovalent coupling, defined herein, to flexible carriers and/or targeting moieties, defined herein. All said definitions for all active agents and derivatives include disclosures and all references from previously filed App. 62/786,340.

The groups of active agents defined as therapeutic for this invention are meant to exclude specific atoms, chemicals, proteins or other molecules used soley or primarily as signalling moieties or "beacons" in various detection methods in the art.

Therapeutic active agents include, but is not limited to, any active agents used for prophylaxis or treatment against pests or vermin or any diseases including cancer, heart disease, immune disorders, neurological diseases, harmful arthropods, any infectious disease organisms, especially intracellular organisms that include viruses, bacteria, mycoplasma, protozoa, fungi, any parasites, and prions. Said pharmaceutical active agent or drug can include any suitable anti-cancer agent, anti-viral agent, antibiotic, pesticide, oligonucleotide, DNA, DNA plasmid, RNA or interfering RNA, any suitable aptamer as described or referenced herein.

Small Molecular Active Agents (AAs) Useful in this Invention.

Small molecular active agents ("small active agents" or "small drugs"), are defined here as limited to pharmaceutical chemicals and other substances with a molecular weight usually less than 1500 Daltons and are inhibitory, antimetabolic, therapeutic or preventive toward any disease (i.e. cancer, viral diseases, bacterial diseases, protozoan diseases, neurological diseases and heart diseases) or inhibitory or toxic toward any disease causing organism. Most preferred small active agents are any suitable therapeutic or prophylactic small drugs categorized in The Merck Index, Thirteenth Ed., Merck & Co. Inc., Rahway NJ (2001), under Therapeutic Category and Biological Activity Index, pages Ther-1 through Ther-31; and those listed by Cserhati, T., Anal. Biochem. 225, 328-332 (1995) the contents of, and references therein, are included in this invention by reference. Small active agents are further defined to the following categories. Chloroquine Substances Useful in this Invention.

A chloroquine substance, is defined here as an AA, or suitably a TM, defined herein, that is usually (but not necessarily), a lysosomotropic substance that includes, but is not limited to, quinoline and quinoline derivatives and/or compounds, especially 4-aminoquinolines and 2-phenylquinoline compounds and amino, thiol, phenyl, alkyl, vinyl and halogen derivatives thereof.

In certain preferred embodiments of this invention, said chloroquine substances are incorporated into said flexible carrier compositions to provide suitable lysosomotropic properties to said carriers to facilitate intracellular trafficking and/or targeting. The most preferred chloroquine substances ("chloroquines"), include chloroquine, hydroxychloroquines, amodiaquins (camoquines), amopyroquines, halofantrines, mefloquines, nivaquines, primaquines, tafenoquine and quinone imines and chloroquine analogs or derivatives wherein the (−)-enantiomers of chloroquine and hydroxychloroquine are most preferred.

Also in this invention, preferred small AAs include "chloroquine combinative" AA or a chloroquine combinative agent (CCA) defined as AAs whose effectiveness or mode of action is potentially improved or potentially synergistic when used in any treatment with any chloroquine substances, defined herein. Antiviral AA Useful in this Invention.

Preferred antiviral AA include, but are not limited to, any enzyme inhibitors including; S-adenosyl-homocysteine (SAH) hydrolase inhibitors, bromovinyldeoxyuridine (BVDU) and derivatives thereof, any anti-human immunodeficiency virus (HIV) agents, valacyclovir, any anti-influenza agents, including any protease inhibitors such as amprenavir, tipranavir, indinavir, saquinavir, lopinavir, fosamprenavir, ritonavir, atazanavir, nelfinavir; mono- and bicyclic inhibitors of FIV and HIV proteases including, but not limited to, disclosures by C. C. Mak, et al, Bioorg Med Chem.11, 2025-40 (2003), that include monocyclic inhibitors containing a 15- or 17-membered macrocycle with an equivalent P3 or P3' group and an unnatural amino acid, (2R, 3S)-3-amino-2-hydroxy-4-phenylbutyric acid; bicyclic inhibitors containing the macrocycles that mimic the P1/P1'-P3/P3' tripeptide [Phe-Val-Ala] of TL3 and Compound 15 of C. C. Mak, et al.

Preferred antiviral AA include, but are not limited to, any nucleoside/nucleotide reverse transcriptase inhibitors (NRTIs) such as abacavir, alovudine, amdoxovir, dexelvucitabine, didanosine, elvucitabine, emtricitabine, lamivudine, stavudine, tenofovir, tenofovir disoproxil fumarate (DF), zalcitabine, zidovudine (AZT); any non-nucleoside reverse transcriptase inhibitors (NNRTIs) such as delavirdines, delavirdine mesylate, delavirdine methane sulfonate, efavirenz, nevirapine, (+)-calanolide A etravirine; any virus entry inhibitors (including fusion inhibitors) such as enfuvirtide (DP178), aplaviroc, maraviroc, vicriviroc, anti-fusion C-peptides and N-peptides (CCIZN17) including covalently stabilized such as those disclosed or referenced by E. Bianchi, et al, (2005) PNAS 102, 12903; any virus maturation inhibitors such as PA-457; any cellular inhibitors such as hydroxyurea; any neuraminidase (NA) inhibitors such as peramivir, oseltamivir (Tamiflu™), oseltamivir carboxylate and Zanamivir including but not limited to, antiviral cyclopentane derivatives, designated as BCX-1812, BCX-1827, BCX-1898, and BCX-1923 by P. Chand, et al, Bioorg Med Chem.13 (12): 4071-7 (2005); any ion channel blockers such as amantadine, rimantadine; and any analogs or derivatives of anti-viral agents. Preferred antiviral AA include, but are not limited to, those disclosed by E De Clercq, Antiviral Res. (2005) 67 (2): 56-75 and LD Lynd, et al, Pharmaco-econo. (2005) 23 (11): 1083-106, including references therein.

Preferred antiviral AA include, but are not limited to, any suitable drugs useful against severe acute respiratory syndrome human coronavirus (SARS) and include, but are not limited to, aurintricarboxylic acids; lopinavir; niclosamides; S-nitroso-N-acetylpenicillamines; 3CL protease inhibitors including those disclosed by Wu, C-Y, et al, PNAS 101, 10012-10017 (2004) (i.e. active compounds shown in FIG. 3, especially protease inhibitor compounds 1 and 2; macrolide compounds 11 and 12); A. Brik, et al, Chem. Biol. 9, 891-896 (2002); A. Brik, et al, Org. Biomol. Chem. 1, 1-14 (2003) and L. Chen, et al, J Virol. 79 (11): 7095-103 (2005) (i.e. cinanserin and the ten best binding candidates to SARS-COV 3CL Proteinase disclosed in supporting information file) that are hereby incorporated herein, including references therein. Most preferred are glycyrrhizins and derivatives, ginsenoside Rb1 and derivatives, alpha-hederins and derivatives, including glycyrrhizinic acid glycosides and derivatives; aescins (or escins) and derivatives and reserpines and derivatives.

Preferred antiviral AA include, but are not limited to, iminocyclitols and derivatives (SARS-COV inhibition perhaps due to the disruption of the envelope glycoprotein processing), valinomycin and derivatives and FP-21399. Preferred antiviral AA include, but are not limited to, any suitable nucleoside drugs including but not limited to, mizoribine, nelfinavir, ribavirin, ribavirin analogues and derivatives including ribavirin 5'-monophosphate; viramidines and derivatives; any inhibitors of inosine monophosphate dehydrogenases (IMPDH) and including but not limited to, the ribavirin-like molecules, ribavirin analogues and other drugs disclosed by R. G Gish, J. Antimicrobial Chemother. 57, 8-13 (2006), including references therein, hereby incorporated herein.

Preferred antiviral AA include, but are not limited to, any suitable drugs useful against human respiratory syncytial virus (HRSV) and include, but are not limited to, VP-14637 and JNJ-2408068, disclosed by L. Douglas, et al, Antimicrob. Agents Chemother. 49 (6): 2460-6 (2005); and synthetic peptides containing amino acids 77 to 95 (especially peptides 80-90) of the intracellular GTPase RhoA including those of P. J. Budge, et al, Antimicrob. Agents Chemother. 47 (11): 3470-7 (2003); and references therein.

Preferred antiviral AA include, but are not limited to, any suitable drugs useful against adenoviruses, adeno-associated viruses (AAV), alphaviruses, arenaviruses, coronaviruses, cytomegalovirus (CMV), flaviviruses, hepatitis viruses, herpesviruses, (oral & genital herpes), herpes zoster virus (shingles), human papiloma virus (HPV, genital warts, anal/cervical cancer), Molluscum Contagiosum, oral hairy leukoplakia (OHL), myxoviruses, oncornaviruses, papovaviruses, paramyxoviruses, parvoviruses, picornaviruses (poliovirus, coxsackievirus, echovirus), poxviruses, reoviruses, rhabdoviruses, rhinoviruses, togaviruses, viroids and any other viral diseases, including drug analogs and derivatives thereof.

Antimicrobial AA Useful in this Invention.

Preferred antimicrobial AA include, but are not limited to, any suitable antibiotic described or referenced herein including analogs and derivatives thereof. Antimicrobial AA include but are not limited to anticancer, antibacterial, antifungal and antiprotozoan substances including various antibiotics including derivatives and analogs such as antibiotic peptides (i.e. bacitracin, capreomycin, polymyxin B, polymyxin E, tyrothricin, vancomycin); beta-lactam antibiotics including penicillins and derivatives (i.e. ampicillin), cephalosporins, (i.e. cephalothin, cephaloridine, cephalexin, cefazolin, cefataxime); anthracyclines (i.e. doxorubicin (DOX), daunorubicin, mitoxantrone); aminoglycosides (i.e. streptomycin, gentamycin, amicacin, sisomycin, tobramycin); ansamycins (i.e. rifamycin); butoconazole, camptothecin, chalcomycin, chartreusin, chrysomicin M, chrysomicin V, chloramphenicol, chlorotetracyclines, clomocyclines, ellipticines, filipins, fungichromins, fusidic acid, fluconazoles, itraconazoles, griseofulvin, griseoviridin, guamecyclines; ilosamides (i.e. lincomycin, clindamycin); macrolides (i.e. azithromycin, brefeldin A, clarithromycin, chlorothricin, FK-506, L-865,818, oleanomycin, spiramycin); quinolones (i.e. ciprofloxacin, nalidixic acid, norfloxin, ofloxacin); methicillins, nystatins, chrymutasins, elsamicin, gilvocarin, ravidomycin, ristocetins A and B, lankacidin-group antibiotics (i.e. lankamycin), mitomycin, phosphomycin, teramycins, tetracyclines (i.e. doxycycline, minocycline, oxytetracyline); wortmannins.

Preferred antimicrobial AA also include, but are not limited to, any suitable drugs useful against *acinetobacter, achromobacter*, actinomycetes, bacterial diarrhea (*Salmonellosis*, Campylobacteriosis, Shigellosis), bacterial pneumonia, *bacteroides, clostridium, chlamydia*, corynebacteria, enteric bacilli, gram-negative bacteria, gram-positive bacteria, hemophilus-*bordetella* bacteria, *lactobacillus*, mycobacteria, (M. *Avium* Complex, MAC), *Mycobacterium Kansasii*, any *mycoplasma, neisseria*, spirochetes, syphilis, neuro-syphilis, pneumococci, *rickettsia*, staphylococci, streptococci, tuberculosis (TB) and any other bacterial diseases, including analogs and derivatives.

Preferred antimicrobial AA also include, but are not limited to, fungicides, antimycotics including polyenes (i.e. amphotericin B, pecilocin, pimarcin), any antifungal agents or drugs useful against any mycoses, ascomycetes, *aspergillus*, basidiomycetes, *blastomyces, candida*, candidiasis (thrush, yeast infection), coccidioidomycosis, coccidiodes, *cryptococcus*, cryptococcal meningitis, deuteromycetes, *histoplasma*, paracoccidiodes, phycomycetes, other yeasts and any other fungal diseases, including analogs and derivatives thereof.

Preferred antimicrobial AAs also include, but are not limited to, antimicrobials and antimalarials including artemisinin, artemisinin derivatives, reserpines, spironolactone, sulfacetamide sodium, sulphonamide, thiamphenicols, thiolutins, any antiprotozoan agents or drugs useful against any protozoan organisms or their diseases, amebiasis, cryptosporidiosis, isosporiasis, leishmaniasis, malaria, microsporidiosis, *pneumocystis* pneumonia (PCP), toxoplasmosis, and other protozoan diseases; pesticides; various purine and pyrimidine derivatives and analogs including 5'-fluorouracil, 5'-fluoro-2'-deoxyuridine, allopurinols, including analogs and derivatives thereof.

Small Hormonal AA Useful in this Invention.

Small hormonal AA include but are not limited to, prostaglandins; various steroidal compounds such as cortisones, estradiols, hydrocortisone, dehydroepiandrosterone (DHEA), testosterone, prednisolones, progesterones, dexamethasones, beclomethasones and other methasone derivatives, other steroid derivatives and analogs including digitoxins, digoxins and digoxigenins. Other AA that are included, but are not limited to, are any vitamins including vitamins A, B12, D3, K3, and folic acid, among others.

Anticancer Active Agents Useful in this Invention.

Preferred anticancer AA are defined as any antineoplastic agents, antibiotics, prodrugs or cell growth inhibitors that are potentially anticancer agents alone or enhanced when combined with other active agents. Anticancer AA include, but are not limited to any agents from other categories that are useful against cancer, such as antimicrobial AA, antiviral AA, protein and peptide AA disclosed or referenced herein. Preferred anticancer AA include but are not limited to, agents against drug resistant forms of cancer that rely on inhibition of apoptosis or on endosomal mechanisms to excrete active agents.

These also include, but are not limited to; aromatase inhibitors (i.e. Femara and Arimidex), anastrazole, any auristatins, monomethyl auristatins, monomethyl auristatin E (MMAE), monomethyl auristatin F (MMAF), calicheamicins, pyrrolobenzodiazepines (PBD), including any pyrrolobenzodiazepine dimers (i.e. SJG-136) or derivatives, maytansines, emtansine, cisplatins, methotrexate, cyclosporin A, taxanes including docetaxel, paclitaxel, fludarabine, cyclophosphamide, irinotecan, actinomycin D, amsacrine, atropine, catharanthine, chlorpromazine, clomiphene, colchicines, daunorubicin, diltiazem, doxorubicin, etoposide, podophyllotoxin, propranolol, quinidine, quinolinium dibromide, rescinnamine, teniposide, trimethoxybenzoylyohimbine, tryptamine, verapamil, desmethoxyverapamil, vinblastine, vincristine, vindoline, indole alkaloids (yohimbine, corynanthine, physostigmine including vindoline and catharanthine moieties of *Vinca* alkaloids), imatinib, cytosine arabinoside and dacarbazine, among others, including derivatives thereof. Preferred anticancer AA include, but are not limited to, disclosures by J H Beijnen, et al, Lancet Oncol. 5, 489-96 (2004) and S Neidle, et al, Nat Rev Cancer 5, 285-96 (2005), including references therein, hereby incorporated herein.

Also included are any suitable inhibitors of P-glycoprotein 1 (P-gp or Pgp, or MDR1) including amiodarone, clarithromycin, ciclosporin, colchicine, diltiazem, erythromycin, felodipine, lansoprazole, omeprazole and other proton-pump inhibitors, nifedipine, paroxetine, sertraline, quinidine, tamoxifen and -verapamil, among others.

Protein and Peptide AA Useful in this Invention.

The protein and peptide AA are defined here as various pharmaceutical proteins, peptides, bioactive peptides, peptide aptamers, nuclear localization sequences and transduction vectors defined herein and polypeptides that are inhibitory, antimetabolic, therapeutic or preventive toward any disease (i.e. cancer, syphilis, gonorrhea, influenza and heart disease) or inhibitory or toxic toward any disease causing agent. They include polypeptide hormones, insulins, interferons, interleukins, laminin fragments, tumor necrosis factors (TNF), cyclosporins, ricins, ricins A, B, C and D including extracts such as RCL I, II, III and IV, saporins including saporin-6 and other ribosome inactivating proteins, tyrocidines and bungarotoxins, among others. Also preferred, with suitable modification, including conjugations and/or derivatizations, are any lytic peptides, or fragments, including those disclosed by Zhou, X-R, et al, Biochimica et Biophysica Acta 1858, 1914-1925 (2016) and Peeler, D J, et al, Biomaterials 192, 235-244 (2019), including all references hereby incorporated herein:

| Name | Source | Amino Acid Sequence |
|---|---|---|
| Melittin | Bee venom | GIGAVLKVLTTGLPALISWIKRKRQQC (Seq ID No: 1) |
| C6M3 | Synthetic | RLWHLLWRLWRRLHRLLRC (Seq ID No: 2) |
| MEP-2 | Bee venom | GFLSILKKVLKVMAHMKC (Seq ID No: 3) |
| CaLL | Synthetic hybrid | KWKLFKKIFKRIVQRIKDFLRC (Seq ID No: 4) |
| CMA-2 | Melittin | GIGAVLKVLTTGLPALISWIHHHHEEC (Seq ID No: 5) |
| FL-20 | Florae/Melittin | GIGAILKVLATGLPTLISWIC (Seq ID No: 6) |
| EB1 | Penetratin | LIRLWSHLIHIWFQNRRLKWKKKC (Seq ID No: 7) |
| Meucin-18 | Scorpion venom | FFGHLFKLATKIIPSLFQC (Seq ID No: 8) |
| LAH | KALA/synthetic | KKLAHALHLLALLWLHLAHALKKAC (Seq ID No: 9) |
| V681-S11K | Synthetic | KWKSFLKTFKKAVKTVLHTALKAISSC (Seq ID No: 10) |
| Endoporter | Synthetic | LHKLLHHLLHHLHKLLHHLHHLLHKLC (Seq ID No: 11) |
| Crabrolin | Hornet venom | FLALILRKIVTALC (Seq ID No: 12) |
| LPE3-1 | GALA/melittin | GWWLALAEAEAEALALASWIKRKRQQC (Seq ID No: 13) |
| Aurein1.2 | Southern bell frog | GLFDIIKKIAESFC (Seq ID No: 14) |
| IsCT | Scorpion venom | ILCKIWEGIKSLFC (Seq ID No: 15) |
| Lyco-L17E | M-lycotoxin | IWLTALKFLGKHAAKHEAKQQLSKLC (Seq ID No: 16) |
| HE | Magainin 2 | GIHHWLHSAHEFGEHFVHHIMNSC (Seq ID No: 17) |
| SPFK | Bovine semen | PKLLKTFLSKWIGC (Seq ID No: 18) |
| TAT | HIV | YGRKKRRQRRRC (Seq ID No: 19) |
| ZXR-1 | mauriporin (Zhou) | FKIGGFIKKLWRSKLA (Seq ID No: 20) |
| ZXR-2 | mauriporin (Zhou) | FKIGGFIKKLWRSLLA (Seq ID No: 21) |

Preferred protein and peptide active agents include pro-apoptotic peptides including the mitochondrial polypeptide called Smac/Diablo, or a region from the pro-apoptotic proteins called the BH3 domain and other pro-apoptotic peptides.

Preferred protein AA also include any therapeutic antibodies, which includes all types of antibodies disclosed or referenced herein that are useful against any disease or disorder. Preferred peptide AAs include all those disclosed by Rastogi, S. et al, Drug Discovery Today, Website: doi.org/10.1016/j.drudis. 2018.10.002 (2018).

Nucleic Acid Active Agents.

When nucleotides and nucleic acids are used as active agents in this invention, preferred nucleic acids include derivatized nucleotides, nucleic acids and aptamers defined herein, and are limited by category to include any pharmaceutical nucleic acids, meaning useful or potentially useful in therapeutic or prophylactic applications in humans, or any other vertebrate animals and in plants. The most preferred nucleic acids defined as pharmaceutical are nucleic acid active agents against viral and other microbial diseases, against cancers, heart diseases, autoimmune diseases, genetic and other diseases or disorders in humans and other vertebrates. Also included are nucleic acid active agents against viral and other microbial diseases in plants. They also include specific DNA sequences used for gene therapy.

Preferred examples of derivatized nucleotides and nucleic acids useful as active agents include any suitably derivatized nucleic acids disclosed and/or categorized herein, including, but are not limited to; any antisense nucleic acids that include phosphodiester antisense oligonucleotides (ON) and antisense oligodeoxynucleotides (ODN); any "backbone derivatized" oligonucleotides or oligodeoxynucleotides (sense and/or antisense), where the sugar-phosphate "backbone" has been derivatized or replaced with "backbone analogues"; any "mixed backbone derivatized" oligonucleotides or oligodeoxynucleotides (sense and/or antisense); any capped nucleic acids; any nucleic acid hybrids (i.e. RNA-DNA hybrids); any nucleic acid chimeras (i.e. RNA-DNA chimeras); any synthetic nucleic acid polymers including peptide nucleic acids (PNA); any nucleotide mimics or co-oligomers like phosphoric acid ester nucleic acids (PHONA); any triplex-forming nucleic acids and mutagenic triplex-forming nucleic acids.

RNA Active Agents Useful in this Invention.

Preferred nucleic acid active agents are any RNA (ribonucleic acid), which includes all types of single stranded or double stranded RNA (dsRNA), including antisense RNA, messenger RNA (mRNA), short hairpin RNA (shRNA), micro RNA (miRNA), crispr RNA (crRNA), single guide RNA (sgRNA) and transfer RNA (tRNA). Also RNA aptamers including aptamers with incorporated 2'-fluoro-pyrimidines. Most preferred are any RNAs useful in RNA interference (RNAi) therapeutics such as small interfering RNAs (siRNA) and interfering dsRNA. Also any micro RNAs (miRNA) defined generally as small (about 20-25 nucleotide), non-protein-coding RNAs that regulate gene expression. Preferred miRNAs include precursor microRNAs such as from primary microRNA (pri-miRNA) and pri-miRNA hairpins.

Also preferred are any antisense nucleic acids used to inactivate mRNA or miRNA, such as antisense nucleic acids containing 2'-O-methyl groups, including those disclosed by Hutvagner, et al, PLOS Biol. 2, 10. 10371/J.pbio.0020114 (2004) and Meister, et al, RNA 10, 544 (2004). Also preferred nucleic acids are any ribozymes and hairpin ribozymes including those disclosed or referenced by Y. Lian, et al, in Gene Therapy, Vol. 6, 1114-1119 (1999).

Also preferred nucleic acid active agents are any splicing RNA (spRNA), defined as any RNA capable of reprogramming or repairing mRNAs (or pre-mRNA) and the proteins they encode. Preferred spRNA repairs or reprograms mRNA through various splicing or trans-splicing mechanisms including through spliceosome-mediated RNA trans-splicing (SMaRT). Also preferred are any suitable riboswitches.

Also preferred are 5' derivatized RNA, or 3' derivatized RNA where the 5' or 3' ends have been capped, or labeled, or extended with additional nucleic acids, or amino acids, or a mutagen, or suitably derivatized in any way. Also preferred are "backbone derivatized" RNAs in which the sugar-phosphate "backbone" has been derivatized or replaced with "backbone analogues" which include phosphorothioate, phosphorodithioate, phosphoroamidate, alkyl phosphotriester, or methylphosphonate linkages or other backbone analogues. Such derivatized RNA includes any sense or antisense sequences. Also preferred are any "modified ribose" nucleic acids and "locked" nucleic acids (LNA) disclosed by Kaur, et al, Chem. Rev. (2007) 107, 4672-4697, hereby incorporated herein including references therein.

Useful for this invention are Locked Nucleic Acid (LNA), wherein the LNA bases are ribonucleotide analogues containing a methylene linkage between the 2'-oxygen and 4'-carbon of the ribose ring. The constraint on the sugar moiety results in a locked 3'-endo conformation that allows for high affinity hybridization. Their advantages for use in said aptamers are close structural resemblance to RNA, high affinity and specificity for suitable target strands and substances, high in vivo stability and low toxicity. DNA Active Agents (AAs) Useful in this Invention.

One category of preferred nucleic acid active agents is DNA (deoxyribonucleic acid), which includes all types of single stranded or double stranded DNA (dsDNA), any DNA aptamers and oligodeoxynucleotides. Preferred DNAs include any 5' derivatized DNA, or 3' derivatized DNA where the 5' or 3' ends have been capped, or labeled, or extended with additional nucleic acids, or amino acids, or a mutagen, or suitably derivatized in any way. Preferred nucleic acids also include all types of inhibitory nucleic acids including those with a poly G motif and the sequences disclosed by A. M. Krieg, et al, U.S. Patent Applic. 20040009949, incorporated herein. Preferred nucleic acids also include enzymatic or RNA-cleaving DNA such as DNAzymes. Potential therapeutic targets for all DNA AAs including any plasmids in this invention include any cancer, and viral, bacterial, protozoan and parasitic diseases, and immunological, cardio-vascular, neurodegenerative diseases and macular degeneration, among others.

Plasmid Active Agents Useful in this Invention.

One category of preferred nucleic acid active agents includes all types of plasmids, defined for this invention as a nucleic acid sequence that can be transcribed to produce or generate RNA or can express a protein. Preferred plasmids can be single, double or triple stranded and include viral vectors (i.e. recombinant) or non-viral based plasmids. Preferred plasmids can contain any suitable vector including viral vectors, nonviral vectors, bacterial vectors (i.e. pCOR) and bacterial element-less vectors and can contain nuclear seeking or nuclear penetrating moieties. Preferred plasmids can suitably be circular, linear (i.e. end protected) or super coiled (covalently closed circular, ccc) plasmid DNA. Preferred plasmids can be conventional expression plasmids, or conditionally replicating plasmids, or nonreplicating mini-circles, or linear dumbbell-shaped expression cassettes.

They can suitably contain native and/or derivatized DNA, nonexpressing sequences such as multiple thymidines or uridines, native and/or derivatized RNA. Preferred plasmids are coupled covalently to any suitable flexible carrier or coupled by intercalation or coupled noncovalently to a suitable cationic flexible carrier substance by cationic-anionic charge attraction.

Some examples (among others), of suitable types of genes and plasmids, including their preparation, useful in this invention are disclosed by JM Silva, et al, Nat Genet. 37 (11): 1281-8 (2005); D. A. Dean, et al, Gene Therapy 12, 881-890 (2005); C. R. Ill, et al, Gene Therapy 12 (10): 795-802 (2005); T. M. Fountaine, et al, Curr Gene Ther. 5 (4) 399-410 (2005); M. Nishikawa, Biol. Pharm. Bull. 28 (2): 195-200 (2005); M. Nishikawa, et al, Adv Drug Deliv Rev. 57 (5): 675-88 (2005); W. M. Pardridge, Expert Opin Biol Ther. 4 (7): 1103-13 (2004); M. Schleef, et al, J Gene Med. 6 Suppl 1: S45-53 (2004); P. Y. Lu, et al, Adv Genet. 54:117-42 (2005); L. Zentilin, et al, Curr Pharm Biotechnol. 5 (4): 341-7 (2004) and are incorporated herein by reference. Also preferred nucleic acids are any suitable plasmids and pCOR plasmids.

Plasmid Active Agents for siRNA, miRNA, spRNA and Vaccination Useful in this Invention.

Preferred small interfering RNA (siRNA) generating plasmids can generate any suitable form of siRNA (i.e. RNAi expression cassettes) and can express any suitable type of single stranded RNA or double stranded RNA, including short hairpin RNA (shRNA). Said plasmids for siRNA can contain any suitable promoters (i.e. RNA polymerase II or III), expression sequences and stop sequences.

Preferred micro RNA (miRNA) generating plasmids can generate any suitable form of micro RNA, micro RNA hairpins or precursor miRNA. Said miRNA generating plasmids contain any suitable promoters (i.e. RNA polymerase II or III), expression sequences and stop sequences.

Preferred plasmids include splicing RNA (spRNA) generating plasmids that generate RNA that can repair or reprogram mRNA through various splicing or trans-splicing mechanisms including through spliceosome-mediated RNA trans-splicing (SMaRT). Preferred plasmids for vaccination can express or generate any suitable form of antigen alone or co-expressed with other proteins. Said plasmids for vaccination can contain any suitable promoters, expression sequences and stop sequences.

Intercalators as Active Agents and NCS.

An intercalator is defined as a substance that is capable of binding to any suitable carrier NA, defined herein, and any nucleic acid defined herein (i.e. nucleic acid zipper), and under suitable conditions, said intercalator can include a substance that is capable of binding to any suitable peptide or polypeptide defined herein. Said intercalators of this invention include those suitable for use in a "noncovalent coupler substance" (NCS), to provide an "active agent coupled NCS" (Active Agent-NCS), defined herein. All said definitions for intercalators include disclosures and all references from previously filed App. 62/786,340.

Said binding is by attractive forces of intercalation known in the art, which generally but not necessarily, involves insertion of all or part of said substance between base pairs of a nucleic acid, or between amino acid residues of a peptide. Said attractive forces can include ionic forces, hydrogen bonding, van der Waals forces and/or hydrophobic (lipophilic) attractive forces. For the purposes of this invention, preferred nucleic acid intercalators are defined by category to compounds that bind to single stranded nucleic acid ("hemi-intercalator") or most preferred, to double stranded (duplex) nucleic acid or to triple stranded (triplex) nucleic acid. Useful with said intercalators, is any suitable double-stranded DNA, which generally consists of two strands running in opposite directions. One is in the direction 5'-3', and the other one is in the direction of 3'-5', providing an antiparallel stranded, (APS-duplex). Also useful with the intercalators in this invention, are any suitable Locked Nucleic Acids (LNA), defined herein.

Also useful with the intercalators in this invention, is single-stranded DNA with a parallel-stranded (PS-duplex) conformation in which both strands adopt the 5'-3' orientation. For this invention, the construction of two-stranded ps-DNA duplexes requires a selection of sequences that are suitably complementary in the parallel orientation but which at the same time are poorly matched toward the function of other possible alternative, potentially competitive antiparallel homo- and heteroduplexes. Preferred ps-duplexes provide suitable resistance to certain nucleases and to restriction endonucleases.

For this invention, ps-duplexes can be formed both in hairpin and in linear form. Several synthetic methods are known which allow preparation of ps-duplexes in vitro. These can be achieved by polarity reversal using a 3'/3' or 5'/5' linkage, using modified oligodeoxynucleotides (ODNs), or via the use of modified backbone, defined herein.

Also useful with the intercalators in this invention are triple helices, wherein a third strand, also called the triplex-forming ODN (TFO), binds within the major groove of the duplex DNA via Hoogsteen (or reverse Hoogsteen) type hydrogen bonding with the exposed groups on the base pairs. The binding of the third strand is highly sequence-specific, and this property of sequence specificity forms the basis of the triplex-based applications that aim to bind a single-stranded DNA (TFO) to a specific target site in duplex DNA, which is known as "Antigene Strategy". Triplexes for this invention can be prepared from either RNA or DNA chains or their combinations, and these can be either intra-molecular or intermolecular. For this invention, the intercalators and disclosures of groove binding compounds, APS duplex DNA, PS duplex DNA and DNA triplexes by Jain, et al, in Bioconjugate Chem. 21, 1389-1403 (2010), are hereby incorporated herein, including references therein.

Intercalators are preferred that have a functional group available that also allows covalent coupling of the intercalator to a specific targeting moiety (i.e. antibody or aptamer), defined herein, and/or an active agent without adversely affecting the nucleic acid intercalating or nucleic acid binding function of the intercalator. When such a functional group is not present, it can be added through suitable derivatization of the intercalator, as defined herein. Preferred intercalators also include intercalator dimers, intercalator trimers or intercalator polymer compositions wherein two, three or more intercalator moieties can bind cooperatively to nucleic acid for increased affinity. There are many preferred types and categories of intercalators for this invention as described herein. Some preferred types and categories of intercalators and can include minor groove binding substances, as described herein that can be used in various ways for this invention. Therefore, one skilled in the art can appreciate that some types of intercalators are more preferred for the intended purpose of this invention than others, and may be listed in more than one category. For this invention, certain preferred intercalators are useful as a noncovalent coupler substance (NCS), defined herein, and/or as active agents, suitably modified, if needed, for their intended purpose.

Covalent Coupling Nucleic Acid Intercalators.

A covalent coupling nucleic acid intercalator is defined as a substance suitable for pharmaceutical use that, in addition to intercalating with nucleic acid, is also capable of forming covalent bonds with the nucleic acid when activated through a photo reactive or chemical process.

Covalent Intercalation Linkage.

A covalent intercalation linkage is defined in this invention as a composition wherein an intercalator is a covalent coupling agent between a nucleic acid and a flexible carrier substance defined herein. Said intercalator is covalently coupled to said flexible carrier substance through suitable functional groups and/or through a covalent cross linking agent and also covalently coupled by "covalent intercalation" to said nucleic acid. Said covalent intercalation comprises intercalation with said nucleic acid and subsequent conversion of the intercalation binding to a covalent bond through chemical or photochemical means.

Photo Reactive Intercalators Useful in this Invention.

The most preferred category of covalent coupling intercalators are the photo reactive intercalators including, but not limited to, furocoumarin compounds disclosed by G. D. Cimino in Ann. Rev. Biochem. 54, 1151-1193 (1985), incorporated herein by reference. Some preferred examples of photoreactive intercalators include psoralens, psoralen amines, hydroxyl psoralens (4'-hydroxymethyl psoralens), trioxsalens (4,5',8-trimethylpsoralens), trioxsalen amines (4'-aminomethyl-4-5'-8-trimethyl psoralens), hydroxyl trioxsalens (4'-hydroxymethyl trioxsalens), methoxsalens, 5-methoxypsoralens, 8-methoxy-psoralens, 4'-hydroxymethyl-4,5',8-trimethylpsoralens, 4'-methoxymethyl-4,5',8-trimethylpsoralens, 4'-chloromethyl-4,5',8-trimethylpsoralens and 4'-N-phthalimidomethyl-4,5',8-trimethylpsoralens.

Also preferred are any suitable amino, vinyl, sulfhydryl or phosphoramidite derivatives of psoralen or trioxsalen including 6-(4'-hydroxymethyl-4,5',8-trimethylpsoralen) hexyl-1-O-(beta-cyanoethyl-N,N'-diisopropyl) phosphoramidite, among others. A preferred amino derivative is "psoralen amine" available from Sigma-Aldrich, St. Louis, MO, 2003 Catalog #P 6100. Also preferred are any suitable derivatives of psoralen or trioxsalen including biotinylated forms as is disclosed by C. Levenson, et al, in Methods in Enzymology 184, 577-583 (1990). Also preferred are any suitable psoralen or trioxsalen active esters (i.e. N-hydroxysuccinimide, or 4-nitrophenyl), including 4'-[(3-carboxy-propionamido) methyl]-4,5',8-trimethylpsoralen N-hydroxysuccinimide ester, as is disclosed by M. A. Reynolds in Bioconj. Chem. 3, 366-374 (1992). Also preferred are suitable amino acid derivatives of psoralen or trioxsalen including aspartic acid-beta-(4'-aminomethyl-4,5',8-trimethylpsoralen) in Z. Wang, et al, in JACS 117, 5438 (1995).

Also preferred are any suitable psoralen or trioxsalen derivatized with anhydride, carboxylate, chloroformate, tosylate or isothiocyanate functional groups. Also preferred are any suitable psoralen or trioxsalen derivatives herein disclosed that include alkyl, or alkyl amino extensions, or spacer groups. Also preferred intercalators include photoreactive anthraquinone derivatives as disclosed by T. Koch, et al, in Bioconj. Chem. 11, 474-483 (2000).

Nucleic Acid Alkylating Agents Useful in this Invention.

Another category of nucleic acid intercalators useful as active agents, includes alkylating agents such as p-azidophenacyl, duocarmycin A (i.e. pyrinamycins) and duocarmycin C. Also the agent (+)-CC-1065 and its analogs possessing the 1,2,9,9a-tetrahydrocyclopropa [1,2-c] benz [1,2-e]indol-4-one (CBI) alkylation subunit including 1-(chloromethyl)-5-dihydro-3H-benz [e] indole (seco-CBI)

disclosed by A. Y. Chang, et al, JACS 122, 4856-4864 (2000), and naphthopyranone epoxides disclosed by K. Nakatani, et al, in JACS 123, 5695-5702 (2001) and references therein. Another category of nucleic acid intercalators includes certain intercalators known to produce covalent nucleic acid complexes such as aflatoxin B oxide and certain pluramycin antibiotics (i.e. kapuramycin A).

Non-Covalent Coupling Nucleic Acid Intercalators Useful in this Invention.

A non-covalent coupling nucleic acid intercalator is defined as a substance suitable for pharmaceutical use, such as an active agent or as an NCS, as defined herein, that generally does not form covalent bonds with the nucleic acid, but is coupled through the forces of intercalation. The most preferred non-covalent coupling nucleic acid intercalators are those that form and maintain the most suitable non-covalent binding with double stranded nucleic acid (duplexes) or triple stranded forms of nucleic acid. Also preferred non-covalent coupling nucleic acid intercalators are those that are suitable for use as an active agent or with an active agent as a noncovalent coupling substance (NCS), defined herein.

Non-Covalent Intercalation Linkage.

A noncovalent intercalation linkage is defined for this invention as a composition wherein any suitable intercalator can be covalently coupled through a cleavable linkage as defined herein, to an active agent but is noncovalently coupled, directly or indirectly (i.e. NCS) as defined herein, through the forces of intercalation to a flexible carrier nucleic acid, defined herein.

Minor Groove Binding Substances.

A preferred type of intercalator for this invention, includes major groove binding substances and especially minor groove binding (MGB) substances. Said groove binding is through attractive forces known in the art, which generally but not necessarily, involves alignment of all or part of said substance with several base pairs of any nucleic acid, or alignment with several amino acid residues of a peptide (i.e. peptide helix or peptide ligand). Said attractive forces can include ionic forces, hydrogen bonding, van der Waals forces and/or hydrophobic (lipophilic) attractive forces. Said minor groove binding substances are defined as substances that bind to the minor groove of double stranded DNA, and can include substances that have both groove-binding and intercalating properties.

Examples of useful groove binding compounds for this invention include, but are not limited to, calicheamicins, monomethylauristatins including, monomethylauristatin E (MMAE), any duocarmycin type of minor groove binders, cyclopropylindoles, natural products such as CC-1065, and synthetic analogues such as the racemic seco chloride amino-CBI compound and racemic seco chloride hydroxy aza-CBI compound, MGB substances disclosed by Jeffery, et al, J. Med. Chem. (2005) 48, 1344-1358, also included are oligopeptides such as netropsin and distamycin, benzimidazoles (Hoechst 33258, Hoechst 33342), DAPI, berenil, bis-quaternary cations (SN 6999, SN 7167, SN 18071), and cyanine dyes (DTDC, DODC). Also included are triple-helix specific compounds, including LS-08, acridine derivatives, MHQ-12, 4-(4-methylpiperazino-2-ethyl-(2-naphthyl) quinoline, and 1-phenyl-4-pyrrolidino-2,3-dihydro-1H-pyrrolo [2,3-b]quinoline, among others.

Acridine and Acridine Derivatives.

Another category of useful nucleic acid intercalators, includes acridine and acridine derivatives such as acridine orange and derivatives thereof, acridine carboxamides, 9-aniloacridine, 3-(9-acridinyl amino)-5-hydroxyethyl aniline (AHMA) derivatives and their alkylcarbamates, acronycines including 1,2-dihydroxy-1,2-dihydro acronycine and 1,2-dihydroxy-1,2-dihydro benzo[b] acronycine diesters, pyrimidol [5,6,1-de] acridines, pyrimidol [4,5,6,-kl] acridines, bis (amine-functionalized) 9-acridone-4-carboxamides, bis (amine-functionalized) acridine-4-carboxamides and pyrazolo[3,4,5-kl] acridine-5-carboxamides.

Also included are bis-acridines disclosed by May, et al, in PNAS, vol. 100, 3416-3421 (2003), and references therein, including bis-(6-chloro-2-methoxy-acridin-9-yl) and bis-(7-chloro-2-methoxy-benzo[b][1,5]-thyridin-10-yl) analogs such as (6-chloro-2-methoxy-acridin-9-yl)-(3-{4-[3-(6-chloro-2-methoxyacridin-9-ylamino)-propyl]-piperazin-1-yl}-propyl)-amine, N,N'-bis-(6-chloro-2-methoxy-acridin-9-yl)-1,8-diamino-3,6-dioxaoctane, and (1-{[4-(6-chloro-2-methoxy-acridin-9-ylamino)-butyl]-[3-(6-chloro-2-methoxy-acridin-9-ylamino)-propyl]-carbamoyl}-ethyl)-carbamic acid tert-butyl ester. Also included are quinacrines and covalent dimers of quinacrine.

Anthracyclines, Anthracenes, Actinomycins and their Derivatives.

Other useful nucleic acid intercalators include anthracyclines such as nogalamycin, daunomycin and adriamycin (doxorubicin), mitoxantrone and ametantrone. Also included are any enediyne antibiotics such as dynemicins and C-1027 including those disclosed by Chen, Y. et al, J Nat. Prod. 74, 420-424 (2011) and Yan, X. et al, J. Nat. Prod. 81, 594-599 (2018), including all references, hereby incorporated herein. Another useful category of nucleic acid intercalators includes anthracenes, phenylanthracenes and their derivatives, including anthraquinolyns. Another useful category of nucleic acid intercalators includes actinomycins including actinomycins C, actinomycins D, 7-amino actinomycins, mitomycin C.

Aminoglycosides and Derivatives.

Another useful category of nucleic acid intercalators includes aminoglycosides such as neomycin B, kanamycin A, and tobramycin including derivatives such as their conjugates with 9-aminoacridine as are disclosed by Luedtke, et al, in Biochemistry 42, 11391-11403 (2003) and references therein. Also included are conjugates neo-N-acridine, neo-C-acridine, tobra-N-acridine, kana-N-acridine, neo-N-neo, tobra-N-tobra, neo-S-acridine, neo-neo, tobra-tobra, and kanaA-kanaA.

Other useful nucleic acid intercalators include porphyrins, hematoporphyrins and derivatives, metal-free porphyrins such as H2TMpyP-4. Also included are four-coordinate metalloporphyrins such as CuTMpyP-4, NiTMpyP-4 and PdTMpyP-4 and [Ru(II)12S4dppz]Cl$_2$.

Pyrenes and Other Intercalators.

Another useful category of nucleic acid intercalators includes suitable pyrene intercalators including 1-O-(1-pyrenylmethyl) glycerol and derivatives thereof. Another category of nucleic acid intercalators includes ethidiums, propidiums, proflavins, ellipticines and 4,6'-diaminide-2-phenylindole (DAPI). Another useful category of nucleic acid intercalators includes distamycin, berenil, Hoechst dyes including Hoechst 33258 and Hoechst 33342.

Noncovalent Coupling Vs. Covalent Coupling of Substances and Coupling Methods.

For the instant invention, two distinct types of coupling are defined to produce several preferred compositions. One type of coupling can be through noncovalent coupling forces, defined as "attractive" forces to form a complex, and/or "host-guest" binding as with a host cyclodextrin and guest molecule, an intercalator and nucleic acid, an antibody binding an antigen, avidins, NeutrAvidins, biotins and D-desthiobiotins, any "binding domain" and ligand or active agent, an aptamer and specific ligand or an aptamer and specific target substance, defined herein. Said noncovalent coupling forces, defined herein, can include binding between substances through ionic bonds, or hydrogen bonds or van der Waals forces, and/or their lipophilic (L+) or hydrophilic (H+) properties and interactions. Most preferred noncovalent coupling can be between an active agent and a flexible carrier composition defined herein, and can contain other moieties either covalently or noncovalently coupled. Also included is said noncovalent coupling between an active agent or TM and a micelle, nanoparticle or liposome.

Unless stated otherwise, the preferred coupling used in coupling said substances and moieties, defined herein, is through covalent coupling, defined as electron-pair bonds or linkages that may be biocleavable (i.e. self immolative), defined herein. Many suitable methods and coupling agents for covalently coupling (or cross linking) of flexible carrier substances including polyethylene glycol and other polymers are known and, with appropriate modification, can be used to couple the desired substances through their "functional groups" for use in this invention. Where stability is desired, the preferred covalent linkages are amide bonds, peptide bonds, ether bonds, and thio ether bonds, among others.

Functional Groups and Intermediate Substances.

A functional group or reactive group is defined here as a potentially reactive moiety or "coupling site" on a substance where one or more atoms are available for covalent coupling to some other desired substance. When needed, functional groups are suitably added to said flexible carrier substances and/or active agents and/or TM of this invention through derivatization or substitution reactions. Examples of functional groups are aldehydes, allyls, amines, amides, azides, carboxyls, carbonyls, epoxys (oxiranes), ethynyls, hydroxyls, phenolic hydroxyls, indoles, ketones, certain metals, nitrenes, phosphates, propargyls, sulfhydryls, sulfonyls, vinyls, bromines, chlorines, iodines, "nucleotide binding site" or domain and others. The prior art has shown that most, if not all of these functional groups can be incorporated into or chemically added to the compositions of this invention.

An intermediate substance is defined as any suitable substance that is optionally included to facilitate coupling between the various moieties of this invention, usually by providing suitable functional groups. Preferred intermediate substances are used to facilitate the coupling of active agents (and/or amplify their number), to the carriers or targeting moieties of this invention. Intermediate substances are suitably modified or derivatized for their intended purpose, and can be any peptides, branched peptide linkages, nucleic acids, polymers and copolymers such as dextrans, poly lactides, poly (dl-lactide/glycolide) polymers, N-(2-hydroxypropyl)-methacrylamides (HPMA), such as cleavable copolymers disclosed by Han, W., et al, Mol Pharm. 14(5): 1405-1417 (2017), polyethylene glycols (PEG), and grafted polymers and any suitable combinations. Also useful in this invention is a pendant or "branched" functional or reactive group defined as a functional group, that is located on any suitable polymer or polypeptide backbone such as pendant polyethylene glycol and any "comb shaped" polymers.

Coupling Agents Useful in this Invention.

A coupling agent (or cross-linking agent), is defined as a chemical substance or moiety, that reacts with and/or provides functional groups on substances to produce a covalent coupling, conjugation or linkage, defined herein, with said substances. When stability is needed in coupling various substances in this invention, covalent coupling, is the preferred method. Depending on the chemical makeup or functional group on a flexible carrier substance, active agent, amphiphilic molecule, cyclodextrin, or targeting moiety (TM), the appropriate coupling agent is used to provide the necessary active functional group or to react with the functional group. In preferred preparations of the instant invention, coupling agents can include cleavable linkages including self immolative linkages, defined herein. All said definitions for coupling agents include disclosures and all references from previously filed App. 62/786,340.

In certain synthesis methods of the instant invention, coupling agents are needed that also provide a linkage with a "spacer" or "spacer arm" as described by O'Carra, P., et al, FEBS Lett. 43, 169 (1974). Said spacer can be included between any flexible carrier substance and targeting molecule and/or an active agent and targeting molecule or intercalator. Preferably, the spacer is a substance of 2 or more carbon atoms in length and can include aliphatic, aromatic and heterocyclic structures and include any suitable "self immolative" spacer, or linkage such as para-aminobenzyloxycarbonyl (PABC) disclosed herein.

With appropriate modifications by one skilled in the art, the coupling methods referenced in U.S. Pat. No. 6,048,736 and PCT/US99/30820, including references contained therein, are applicable to the synthesis of the preparations and components of the instant invention and are hereby incorporated by reference. Useful derivatizing and/or coupling agents for preparing said compositions are bifunctional, trifunctional or polyfunctional cross linking agents that will covalently couple to the functional groups of said compositions, suitable monomers and other substances.

Useful in this invention are coupling agents selected from the group of oxiranes or epoxides. Some preferred examples of oxiranes and epoxides include; epichlorohydrin, 1,4 butanediol diglycidyl ether (BDDE), bis(2,3-epoxycyclopentyl) ether 2,2'-oxybis (6-oxabicyclo[3.1.0]hexane) (BECPE), glycerol diglycidyl ether (GDE), trimethylolpropane triglycidyl ether (TMTE), tris (2,3-epoxypropyl) isocyanurate (TEPIC), glycerol propoxylate triglycidyl ether (GPTE), 1,3-butadiene diepoxide, triphenylolmethane triglycidyl ether, 4,4'-methylenebis (N,N-diglycidylaniline), tetraphenylolethane glycidyl ether, bisphenol A diglycidyl ether, bisphenol A propoxylate diglycidyl ether, bisphenol F diglycidyl ether, cyclohexane-dimethanol diglycidyl ether, 2,2'-oxybis (6-oxabicyclo[3.1.0]hexane), polyoxyethylene bis (glycidyl ether), resorcinol diglycidyl ether, ethylene glycol diglycidyl ether (EGDE) and low molecular weight forms of poly (ethylene glycol) diglycidyl ethers or poly (propylene glycol) diglycidyl ethers, among others.

Other preferred derivatizing and/or coupling agents for hydroxyl groups are various disulfonyl compounds such as benzene-1,3-disulfonyl chloride and 4,4'-biphenyl disulfonyl chloride and divinyl sulfone (J. Porath, et al, J. Chromatog. 103, 49-62, 1975), among others.

Most preferred coupling agents are also chemical substances that can provide the bio-compatible linkages for synthesizing the compositions of the instant invention. Covalent coupling or conjugation is done through functional groups using coupling agents such as glutaraldehyde, formaldehyde, cyanogen bromide, azides, p-benzoquinone, maleic or succinic anhydrides, carbodiimides, ethyl chloroformate, dipyridyl disulfide and polyaldehydes.

Also most preferred are derivatizing and/or coupling agents that couple to thiol groups ("thiol-reactive") such as agents with any maleimide, vinylsulfonyl, bromoacetal or iodoacetal groups, including any bifunctional or polyfunctional forms. Examples are m-maleimidobenzoyl-N-hydroxysuccinimide ester (MBS), succinimidyl 4-(N-maleimidomethyl) cyclohexane-1-carboxylate (SMCC), succinimidyl 4-(p-maleimidophenyl) butyrate (SMPB), dithiobis-N-ethylmaleimide (DTEM), 1,1'-(methylenedi-4,1-phenylene) bismaleimide (MPBM), o-phenylenebismaleimide, N-succinimidyl iodoacetate (SIA), N-succinimidyl-(4-vinylsulfonyl)benzoate (SVSB), and tris-(2-maleimidoethyl) amine (TMEA), among others.

Other coupling groups or agents useful in this invention are: p-nitrophenyl ester (ONp), thiazolidine-2-thione functional group (TT), on various linkers and polymers, bifunctional imidoesters such as dimethyl adipimidate (DMA), dimethyl pimelimidate (DMP), dimethyl suberimidate (DMS), methyl 4-mercapto-butyrimidate, dimethyl 3,3'-dithiobis-propionimidate (DTBP), and 2-iminothiolane (Traut's reagent);

bifunctional tetrafluorophenyl esters (TFP) and bifunctional NHS esters such as disuccinimidyl suberate (DSS), bis[2-(succinimido-oxycarbonyloxy) ethyl] sulfone (BSOCOES), disuccinimidyl (N,N'-diacetylhomocystein) (DSAH), disuccinimidyl tartrate (DST), dithiobis (succinimidyl propionate) (DSP), and ethylene glycol bis (succinimidyl succinate) (EGS), and various derivatives such as their sulfo-forms;

heterobifunctional reagents such as p-nitrophenyl 2-diazo-3,3,3-trifluoropropionate, N-succinimidyl-6 (4'-azido-2'-nitrophenylamino) hexanoate (Lomant's reagent II), and N-succinimidyl-3-(2-pyridyldithio) propionate (SPDP), including various derivatives such as their sulfo-forms;

homobifunctional reagents such as 1,5-difluoro-2,4-dinitrobenzene, 4,4'-difluoro-3,3'-dinitrophenylsulfone, 4,4'-diisothiocyano-2,2'-disulfonic acid stilbene (DIDS), p-phenylene-diisothiocyanate (DITC), carbonylbis (L-methionine p-nitrophenyl ester), 4,4'-dithiobisphenylazide and erythritolbiscarbonate, including derivatives such as their sulfo-forms.

Also useful are energy activated coupling agents wherein ultraviolet (UV), visible and/or microwave radiation can promote coupling or cross linking of suitably derivatized substances. Preferred examples are photochemical coupling agents disclosed in U.S. Pat. No. 4,737,454, among others.

Coupling agents useful in this invention are photoactive coupling agents such as N-5-azido-2-nitrobenzoylsuccinimide (ANB-NOS), p-azidophenacyl bromide (APB), p-azidophenyl glyoxal (APG), N-(4-azidophenylthio) phthalimide (APTP), 4,4'-dithio-bis-phenylazide (DTBPA), ethyl 4-azidophenyl-1,4-dithiobutyrimidate (EADB), 4-fluoro-3-nitrophenyl azide (FNPA), N-hydroxysuccinimidyl-4-azidobenzoate (HSAB), N-hydroxysuccinimidyl-4-azidosalicylic acid (NHS-ASA), methyl-4-azidobenzoimidate (MABI), p-nitrophenyl-2-diazo-3,3,3-trifluoropropionate (PNP-DTP), 2-diazo-3,3,3-trifluoropropionyl chloride, N-succinimidyl-6 (4'-azido-2'-nitrophenylamino) hexanoate (SANPAH), N-succinimidyl (4-azidophenyl) 1,3'-dithiopropionate (SADP), sulfosuccinimidyl-2-(m-azido-o-nitobenzamido)-ethyl-1,3'-dithiopropionate (SAND), sulfosuccinimidyl (4-azidophenyldithio) propionate (Sulfo-SADP), sulfosuccinimidyl-6-(4'-azido-2'-nitrophenylamino) hexanoate (Sulfo-SANPAH), sulfosuccinimidyl-2-(p-azidosalicylamido) ethyl-1,3'-dithiopropionate (SASD), and derivatives and analogs of these reagents, among others. The structures and references for use are given for many of these reagents in, "Pierce Handbook and General Catalog", Pierce Chemical Co., Rockford, IL, 61105. Also useful in synthesizing the components of the instant invention are enzymes that produce covalent coupling such as nucleic acid polymerases and ligases, among others.

Cleavable and Biocleavable Linkages or Bonds Useful in this Invention.

A linkage is defined as a chemical moiety within the compositions disclosed that results from covalent coupling or bonding of the substances disclosed to each other. A linkage can be cleavable, biodegradable (biocleavable) or non-biodegradable and can contain suitable "spacers" defined herein.

For the instant invention, a cleavable linkage (CL) includes biocleavable linkages or chemical bonds and is defined as any type of specific chemical moiety or group that can be used within the compositions to covalently couple together or cross-link any suitable combination of the moieties of this invention, including flexible carrier substances, intermediate substances, active agents, polypeptides, nucleic acids, intercalators, targeting moieties, amphiphilic molecules and grafted polymers described herein.

And wherein said cleavable linkage (CL) is suitably chemically cleavable for the purposes of this invention. And wherein said biocleavable linkage is defined as a cleavable linkage cleavable in a biological environment or process that includes, but is not limited to, enzymatic cleavage, reductive cleavage, hydrolysis, and any suitable chemical or physical cleavage. They may also be contained in certain embodiments of the instant invention that provide the function of force responsive release of active agents as described herein. Some suitable examples are disclosed for use in oral delivery by V. R. Sinha, et al, Europ. J Pharm. Sci. 18, 3-18 (2003) and references therein. Cleavable linkages are distinguishable by their structure and function and are defined here under distinct categories or types.

Self Immolative Linkages or Spacers.

Preferred cleavable linkages, with suitable modification for this invention, include any suitable "self immolative" linkages, defined herein. Preferred are self immolative linkages are those that also contain a cleavable disulfide (SS) linkage defined here as "self immolative SS linkage" (SISS linkage). Also preferred are self immolative linkages that contain any suitable cleavable peptide linkage, defined here as "self immolative peptide linkage" (SIP linkage) and any suitable diazeniumdiolate (DZD) linkage, defined herein.

With suitable modification for this invention, preferred "self immolative" linkages include those disclosed by Toki, et al, J. Org. Chem. 67, 1866-1872 (2002), Chen, et al, Bioconj. Chem. 21, 979-987 (2010), Elsadek, et al, ACS Med Chem Lett., pubs.acs.org, (2010), Jeffrey, et al, J. Med. Chem. 48, 1344-1358 (2005), and Shamis, et al, in JACS 126, 1726-1731 (2004), including references therein. Also preferred are any forms of para-aminobenzyl carbonyls (PABC), as disclosed by Alouane, A., et al, Angew. Chem. Int. Ed. 54, 7492-7509 (2015); DeWit, M A, et al, Org. Biomol. Chem., 9, 1846 (2011); Seidi, F., et al, Chem. Rev. 118, 3965-4036 (2018), including references therein. Another suitable self immolative linkage for this invention can contain a diazeniumdiolate (DZD), moiety including the coupling of any suitable active agent in said invention, that can release nitric oxide upon cleavage or degradation.

Example Synthesis of Self Immolative Disulfide (SISS) Linker.

Preferred embodiments of this invention include an NHS-activated ester of an SISS linker that includes a covalently coupled active agent, that can be directly coupled to any suitable amino group on any suitable nucleic acid, any suitable flexible carrier, NCS, any aptamer, or any suitable antibody, defined herein. Preferred disulfide linkages are cleavable linkages that are initially hindered or protected, until said flexible carrier is opened. With suitable modification for this invention, synthesis is suitably adapted from disclosures of Chen, et al, Bioconj. Chem. 21, 979-987 (2010), among others. Useful methods are also suitably adapted for the preparation of TIPS-Protected, Self Immolative Dithiol (SISS) Linkers, suitably coupled to any suitable hydroxylated active agent, such as Taxol or hydroxychloroquine, among others, defined herein. Or, for the preparation of N-Hydroxy-succinimide (NHS)-Activated Ester of SISS Linker coupled to any hydroxylated active agent, defined herein. Useful methods are also suitably adapted for the preparation of any suitable active agent coupled to a flexible carrier, or NCS, defined herein.

Ester Linkages.

The ester bond is a preferred type of linkage that includes those between any carboxylic acid and any alcohol or hydroxyl group. Preferred cleavable ester bonds are between a flexible carrier or NCS, defined herein, and an active agent and can be protected from cleavage when said flexible carrier is in its closed form, as disclosed herein. Preferred ester bonds include any of the ester bonds used in the preparation of prodrugs or prodrug conjugates including but not limited to disclosures by S. Gunaseelan, et al, Bioconj. Chem. 15, 1322-1333 (2004) and VR Sinha, et al, Europ. J Pharma. Sci. 18, 3-18 (2003), including references therein. Another preferred type is certain imidoesters formed from alkyl imidates. Also included are certain maleimide bonds as with sulfhydryls or amines used to incorporate a cleavable linkage. With suitable modification for this invention, said ester linkages can include any suitable "self immolative" linkage disclosed herein.

Acid Labile Linkages.

Another preferred category in this invention comprises cleavable linkages that are more specifically cleaved after entering the cell (intracellular cleavage). Preferred cleavable acid labile bonds are between a flexible carrier or NCS, defined herein, and an active agent and can be protected from cleavage when said flexible carrier is in its closed form, as disclosed herein.

The preferred cleavable linkages for release of active agents and other moieties within the cell are cleavable in acidic conditions like those found in lysosomes. One type is an acid-sensitive (or acid-labile) hydrazone linkage as described by Greenfield, et al, Cancer Res. 50, 6600-6607 (1990), and references therein. Another type of preferred acid-labile linkage is any type of ortho ester, polyortho or diortho ester linkage, examples disclosed by J. Heller, et al., Methods in Enzymology 112, 422-436 (1985), J. Heller, J. Adv. Polymer Sci. 107, 41 (1993), M. Ahmad, et al., J. Amer. Chem. Soc. 101, 2669 (1979) and references therein. Also preferred are acid labile phosphonamide linkages disclosed by J. Rahil, et al, J. Am. Chem. Soc. 103, 1723 (1981) and J. H. Jeong, et al, Bioconj. Chem. 14, 473 (2003). Another preferred category is certain aldehyde bonds subject to hydrolysis that include various aldehyde-amino bonds (Schiff's base), or aldehyde-sulfhydryl bonds. With suitable modification for this invention, said acid labile linkages can include any suitable "self immolative" linkage disclosed herein.

Cleavable Peptide Linkages.

A preferred category of cleavable linkages or bonds is cleavable peptides or polypeptides from 2 to 100 residues in length, preferably from 2 to 20 residues in length. Preferred cleavable peptide linkages are between a flexible carrier, or a noncovalent coupling substance (NCS), or a cleavable ligand linkage (CLL), defined herein, and an active agent ("Drug"), and can be protected from cleavage when said flexible carrier is in its closed form, as disclosed herein. These are defined as certain natural or synthetic polypeptides that contain any amino acid sequences (i.e. hydrophobic or citrullinated) that are cleaved by specific enzymes such as any cathepsins (i.e. cathepsin B, L, V, etc.), found primarily inside the cell (intracellular enzymes). Using the convention of starting with the amino or "N" terminus on the left and the carboxyl or "C" terminus on the right, some examples are: any peptides that contain the amino acids; Leu, Arg, Phe-Leu, Leu-Phe, Phe-Phe, Arg-Arg, Ala-Leu, Phe-Arg, Phe-Lys, Ala-Phe-Lys, Gly-Leu-Phe-Gly (Seq ID No:22), Valine-Citrulline (i.e. VC(S)) and Ala-Leu-Ala-Leu (Seq ID No:23), Gly-Phe-Leu-Gly (GFLG) (Seq ID No: 24), Tyr-Arg-Arg-Leu (YRRL) (Seq ID No:25) including any stereoisomers (i.e. VC (R)), and other combinations. Preferred examples (among others) include leucine enkephalin derivatives and any cathepsin cleavable peptide sequences and include linkages disclosed by Fujii, Y., et al, Protein Express. Purif. 95, 240-247 (2014); Peterson, J J, et al, in Bioconj. Chem. 10, 553-557 (1999); Tabata, S., et al, Protein Express. Purific. 147, 94-99 (2018); Schmid, et al, Bioconj. Chem. 18, 702-716 (2007); Shiose, et al, Bioconj. Chem. 20, 60-70 (2009); Wood, D W, Current Opin. Struct. Biol. 26:54-61 (2014) and Zhong, Y-J, et al, Chem. Rev. 118, 3965-4036 (2018) and references therein and U.S. patent application Ser. No. 10/923,112 that are incorporated herein by reference.

Preferred peptide linkages include any peptide linkages used in the preparation of prodrugs or prodrug conjugates, and antibody drug conjugates (ADC). With suitable modification for this invention to include coupling to suitable aptamers, nanostructures and medical devices, said peptide linkages can include any suitable "self immolative" spacer, or linkage moiety such as para-aminobenzyloxycarbonyl (PABC) disclosed herein and by Anami, Y., et al, Nature Comm. 9, 2512 (2018) and Dorywalska, M., et al, Mol. Cancer Ther. 15, 958 (2016), for valine-citrulline (VCit) dipeptide linkers. And as disclosed by Anami, and others, said linkers can include a PABC group and/or additional amino acids such as glutamic acid (i.e. Glu-Val-Cit-PABC) and further can include suitable branched linkers. And wherein said branched linkers can have any suitable hapten or ligand, including digoxigenin, coupled to one of said branched linkages and one or more suitable active agents (i.e. monomethyl auristatin F (MMAF)), coupled to other said branches, wherein said ligand with branched linker and MMAF, provides a suitable cleavable ligand linkage of this invention, defined herein. All of said references disclosed in this invention, including supplementary materials and references therein, are incorporated herein by reference.

Disulfide Linkages.

A preferred category comprises the disulfide linkages that are well known for covalent coupling. Preferred cleavable disulfide bonds are between a flexible carrier or NCS, defined herein, and an active agent and can be protected from cleavage when said flexible carrier is in its closed form, disclosed herein. Preferred types of disulfide linkages are any produced by thiol-disulfide interchange (J. Carlsson, et al, Eur. J. Biochem. 59, 567-572 (1975). Preferred disulfide bonds include any of the disulfide bonds used in the preparation of prodrugs or prodrug conjugates. With suitable modification for this invention, said disulfide linkages can include any suitable "self immolative" linkage disclosed herein.

Protected Disulfide Linkages.

Under suitable conditions, another preferred type of cleavable linkage is any "hindered" or "protected" disulfide bond that includes moieties in the bond that sterically hinder or inhibit attack from thiolate ions or other cleavage mechanisms. Examples of (but not limited to) such protected disulfide bonds are found in the coupling agents: S-4-succinimidyl-oxycarbonyl-alpha-methyl benzyl thiosulfate (SMBT) and 4-succinimidyloxycarbonyl-alpha-methyl-alpha-(2-pyridyldithio) toluene (SMPT). Another useful coupling agent resistant to reduction is SPDB disclosed by Worrell, et al., Anticancer Drug Design 1:179-188 (1986). Also included are certain aryldithio thioimidates, substituted with a methyl or phenyl group adjacent to the disulfide, which include ethyl S-acetyl 3-mercaptobutyrothioimidate (M-AMPT) and 3-(4-carboxyamido phenyldithio) propriothioimidate (CDPT), disclosed by S. Arpicco, et al., Bioconj. Chem. 8 (3): 327-337 (1997). With suitable modification for this invention, said protected disulfide linkages can include any suitable "self immolative" linkage disclosed herein.

Azo and GIT Specific Linkages.

Another preferred type of cleavable linkage in this invention are any suitable azo linkages and aromatic azo linkages that are cleavable by specific azo reductase activities in the colon. Gastrointestinal tract (GIT) specific linkages are defined for this invention as chemical linkages or bioconjugates between any active agents, prodrugs, nucleic acids, flexible carrier substances and any suitable moiety wherein said linkage is cleavable by bacterial action including bacterial hydrolysis. Preferred cleavable azo and GIT specific bonds are between a flexible carrier or NCS, defined herein, and an active agent and can be protected from cleavage when said flexible carrier is in its closed form, as disclosed herein. They include, but are not limited to, azo, aromatic azo, amide, glycosidic, glucuronide, and ester linkages.

Examples that can be suitably modified for this invention are disclosed by, but not limited to, J. Kopecek, et al., In: Oral Colon Specific Drug Delivery; D. R. Friend, Ed., pp 189-211 (1992), CRC Press, Boca Raton, FL. and Sinha, V R, et al, European J Pharma. Sci. 18, 3-18 (2003), the contents of which, including references therein, are incorporated into this invention by reference.

Targeting Moiety (TM).

For the purposes of this invention and throughout all disclosures and examples herein, a "targeting moiety" (TM, plural TMs), is a moiety (or molecule), or biorecognition molecule, or "specific binding moiety", that binds to the surface of, or the antigenic site of, or specific biological site of any suitable target substance, defined herein. Any suitable target substance includes any specific molecule, macromolecule, organelle, membrane, cell, tissue, biomarker, disease marker, antigen, microorganism, virus, parasite, pest or other organism, defined herein. All said definitions for targeting moieties include disclosures and all references from previously filed App. 62/786,340.

In all the composition examples provided herein, TM or $(TM)_R$ is a moiety selected from the group of targeting moieties as described herein and is suitably incorporated into, or is covalently coupled to any said flexible carrier substance of this invention through a covalent linkage, as defined herein. Said TM is preferably part of the same synthetic structure of its respective composition, such as a continuous nucleic acid or amino acid sequence, or strand, such as when said composition is a flexible carrier aptamer, defined herein. Or is part of a recombinant antibody structure, as defined herein. Said TM is located and/or coupled at any suitable position, including at or near the end of said flexible carrier substance.

In all the examples provided herein, where applicable, any iteration of said TM, including TM-A, TM-B, TM-C, TM-D, (TM)$_R$, (TM-A)$_R$, (TM-B)$_R$, (TM-C)$_R$, (TM-D)$_R$, etc., is a targeting moiety as defined herein. And wherein, unless specified otherwise, represents one or more said targeting moieties, and when applicable, subscript R is an integer between 1 and 20, preferably between 1 and 5, or said subscript R is an integer 0 (meaning no TM).

Under suitable conditions, said targeting moiety, TM may be an optional substance such as a member independently selected from the group consisting of hydrogen (H), hydroxyl (OH), halogens, lipids, peptides, transduction vectors (TV), and chloroquine substances, defined herein, that provides a specific function such as facilitating longer circulation time and/or cell internalization and/or intracellular trafficking of said composition.

In addition to being said targeting moiety, TM may also be a member independently selected from the group consisting of amphiphilic molecules, capping moieties and grafted polymers as disclosed herein.

Also with the proviso wherein said flexible carrier substance can contain a suitable combination of active agents (with cleavable linkages), functional groups, halogens, targeting moieties, cell transduction vectors, amphiphilic molecules and grafted polymers, as defined herein, that are coupled on the same flexible carrier substance and/or are within the same flexible carrier substance composition.

Antibodies as Targeting Moieties (TM).

Preferred TMs also include any suitable antibodies as are defined herein, with suitable modification of specificity and synthesis methods, as needed. Useful antibodies can be engineered or are commercially available, including rituximab and gemtuzumab, including mutant-specific p53 antibody, PAb240 (Abcam), including isoforms as disclosed by Milicivec, Z., et al, Scient. World J., Article ID 618698, 1-10 (2014); among others. And include suitable bispecific antibodies, chimeric antibodies, antibody fragments, Fabs, scFv dimers (i.e. diabodies), minibodies, triabodies, tetrabodies, and single domain antibodies, scFv, including those disclosed by Govorko, D., et al, J. Immunological Meth. 258, 169-181 (2001) and Slastnikova, T. A., et al, Frontiers in Pharmacol. 9, Article 1208 (2018), for engineered antibodies, antibody derivatives and/or polypeptides including in all references, that are incorporated herein. Also included are other antibody-like scaffolds, engineered antibodies and/or proteins including engineered Complementarity-Determining Regions (CDR) and CDR loops such as disclosed by Huovinen, T., et al, Protein Engin., Design & Selection 26, 683-693, (2013), among others. Preferred antibodies can be suitably engineered as monoclonal antibodies against any suitable mutated protein such as the R175H, R248Q, and R273H hotspot mutations of the tumor suppressor p53 protein, as disclosed by Hwang, L-A., et al, Cell Reports 22, 299-312, (2018), and others, including antibodies and synthesis methods disclosed in supplementary information and in references, that are incorporated herein.

In this invention, compositions containing active agents or drugs can be "targeted" by coupling them to a targeting moiety (or molecule), defined herein, that has a specific binding affinity for the cells, tissue or organism that the drug is intended for. For this invention, a biorecocognition molecule or targeting molecule is coupled to any suitable active agent or to any suitable flexible carrier substance or nanoparticle, defined herein. Or, a targeting moiety is coupled to any suitable active agent or NCS, that is also suitably coupled to a flexible carrier substance. Preferred targeting moieties include, but are not limited to, disclosures by S. Jaracz, et al, Bioorg Med Chem. (2005) 13 (17): 5043-54, including references.

Preferred TMs such as aptamers, are further defined herein, including their use when coupled to the flexible carriers and/or the active agents of this invention. Preferred TMs are also suitable for pharmaceutical or diagnostic use. Categories of TMs useful in this invention are described herein.

Ligand TM.

For this invention, a ligand is suitably defined as a type of targeting moiety or biorecognition molecule defined as a selectively bindable material that has a selective (or specific), affinity for another substance. The ligand is recognized and bound by a usually, but not necessarily, larger specific binding body or "binding partner", or "receptor". Examples of ligands suitable for use as targeting moieties are suitably coupled to the nucleic acids, peptides, aptamers, antibodies and other compositions of this invention and include organic molecules (including certain drugs), peptide ligands, antigens, haptens, biotin, D-desthiobiotin, biotin derivatives, lectins, galactosamine and fucosylamine moieties, receptors, enzyme substrates, coenzymes and cofactors among others. All said definitions for ligands include disclosures and all references from previously filed App. 62/786,340.

For this invention preferred TMs include but are not limited to, prostaglandins; various steroidal compounds such as cortisones, estradiols, hydrocortisone, dehydroepiandrosterone (DHEA), testosterone, prednisolones, progesterones, dexamethasones, beclomethasones and other methasone derivatives, other steroid derivatives and analogs including digitoxins, digoxins and digoxigenins. Other useful TMs that are included, but are not limited to, are any vitamins including vitamins A, B12, D3, K3, ascorbic acid, poly-ascorbic acid and folic acid, including derivatives thereof, among others.

For instance, certain ligands are known in the art for preferential targeting of various diseases, including cancer cells. They include, with suitable modification, disclosures by Xia, W., et al, J. Med. Chem. 53, 6811-6824 (2010), Vlahov, I R, et al, Bioconj. Chem. 23, 1357-1369 (2012), for folate receptor targeting; Luleburgaz, S., et al, Macromol. Rapid Commun. 38, 1600772 (2017), using ADMET for synthesizing poly-ascorbic acid, Li, F., et al, Macromol. Biosci. 14, 280-288 (2014), for caprolactone ascorbic acid, Salmaso, S., et al, Bioconj. Chem. 20, 2348-2355 (2009), for PEC conjugates using Br-derivatized ascorbic acid, also useful for coupling to any suitable amino-containing drug or carrier, disclosed herein. Wherein said references are hereby incorporated herein, including all supporting information and references therein.

When applied to this invention, a ligand can include an antigen (i.e. epitope), or hapten that is capable of being bound by, or to, its corresponding antibody or fraction thereof. Also included are viral antigens, nucleocapsids and cell-binding viral derivatives including those from any DNA and RNA viruses, AIDS, HIV and hepatitis viruses. Also included are any suitable substances (i.e. peptides, triscatecholate siderophores) that bind to and/or penetrate parasites or microorganisms, such as siderophores, sideromycins, albomycins and suitable conjugates thereof. Preferred examples, with suitable modification, include those disclosed by Gorska, A, et al, Trends in Pharmacological Sci. 35, 442 (2014), Ghosh, M, et al, J. Med. Chem. 60, 4577-4583 (2017) and useful linear small peptides RWr and RWrNM with high affinity and specificity to αvβ3 integrin disclosed by Ma, Y., et al, Theranostics 7(6): 1511-1523 (2017) and wherein said references are hereby incorporated herein, including all supporting information and references therein.

Most preferred in this invention, are ligands, peptides and other molecules useful as targeting moieties (i.e. ligand TM, or TM), that specifically bind to proteins, DNA, RNA or other substances identified as disease-specific targets. Said molecules are generally described as drugs that can bind "druggable" proteins and include so-called "stabilizing drugs" that bind mutated proteins such as tp53, among others. Said ligand TMs can be suitably coupled through suitable covalent linkages, defined herein, using well known methods, to the flexible carrier compositions of this invention. Said linkages can also include, as needed, suitable spacer groups, defined herein. Under suitable conditions and modifications to fit their purpose, said ligand TMs can be used in any examples disclosed for this invention. For instance, for use as a ligand TM in this invention, any suitable ligand can be modified, using well known methods, to increase affinity and/or specificity. Said modification can include suitable ligand dimerization or ligand linking and/or, they can be modified to include a functional group or coupling agent, defined herein, that will covalently couple said ligand to the target substance and/or target site after specific binding. Preferred ligands and molecules useful for this invention, including screening and optimization methods, are disclosed by, but not limited to, the following references, which are incorporated herein, including references therein.

Basse, N., et al, Chemistry & Biol. 17, 46-56 (2010), including Supplemental Information; for scaffolds and useful lead ligands "lead fragments" that all bind the mutational cavity of mutated protein p53-Y220C, including, but not limited to, "fragments" 3, 4, 11, 14 and the benzothiazole-based fragment 15, and disclosure of two molecules of fragment 2 that can be linked to increase affinity, among others, Leung, I., et al, J Mol Biol 429, 115-127 (2017) and Zhang, W., et al, PLOS Pathog 13(5): e1006372 (2017), for useful scaffolds based on diverse phage-displayed naïve ubiquitin variants (Ubv) library that can be applied to intracellular targeting including viruses, in this invention. Liu, H., et al, Front. Immunol. 8:38 (2017), for useful bispecific and other antibody scaffolds. Also, Joerger, A C, et al, Annu. Rev. Biochem. 85, 375-404 (2016), including all references therein; for useful "small-molecule stabilizers of p53" mutations and "mutant-specific drugs" against oncogenic proteins. Most preferred are chemically diverse tp53 Y220C stabilizers with unique binding modes, including but not limited to, structures PK7088, PhiKan083, PhiKan5196, PhiKan7242, among others. Also preferred are alkylating agents with activated double bonds that are potential Michael acceptors forming a covalent bond with the thiol group of any cysteines at or near a targeted binding area or "pocket" on any suitable target substance, defined herein, including mutated p53 proteins. Useful disclosed examples include, but are not limited to, MIRA-1, curcumin, STIMA-1, methylene quinuclidinone, Piperlongumine, CP-31398, PRIMA-1 and APR-246, among others.

Also, Orgad, S., et al, FEBS Letters 579, 5609-5615 (2005), for ME1, a useful mouse single chain Fv 1 fragment (scFv) against the common epitope of mutant p53; Govorko, D., et al, J. Immunological Methods 258, 169-181(2001), for useful single-chain scFv antibody gene library using phage display to bind the epitope peptide FRHSVV which mimics the common epitope in p53 mutant protein molecules; and Parrales, A. et al, Front. Oncol. 5, 288 (2015), discloses useful compounds that, with suitable modification, are useful as ligands for binding mutant p53 in this invention. Yue, X., et al, J Mol Biol. 429, 1595-1606 (2017); discloses useful targets for useful ligands that can bind mutant p53 (mutp53) proteins in human cancers that fall within 6 "hotspots", including amino acid residues R175, G245, R248, R249, R273, and R282, among others.

Synnott, N C, et al, Cancer Letters 414, 99-106 (2018); discloses useful ligands that are 2-sulfonyl-pyrimidine compounds, PK11000, PK11007 and PK11010 that bind mutant p53 protein with structural mutation, Arg175His, and that PK11007 altered the conformation of the mutant p53 protein. Also a commercially available, mutant-specific p53 antibody, PAb240 (Abcam), is disclosed and referenced, that is useful as a targeting moiety in this invention. And Hwang, L-A, et al, Cell Reports 22, 299-312 (2018), disclose useful antibodies against mutant p53 (i.e. R175H, R248Q, and R273H hotspot mutants), as TMs useful in this invention including methods that utilized thioredoxin A (TrxA) protein with a protruding peptide loop, as a fusion partner in an *Escherichia coli* expression system, including references therein.

Also preferred targeting moieties are any suitable "chimeric antigen receptors" (CAR) used to generate engineered T cells and other engineered cells against cancer, wherein said receptor moieties are polypeptide sequences that can be suitably modified, such as through protein and/or genetic engineering, as needed for use as targeting moieties in this invention. For instance, said receptor sequences can be suitably incorporated into, or coupled to, the flexible carriers, peptide aptamers, and/or antibody-like scaffolds disclosed herein to provide targeting moieties with similar or identical binding affinities for this invention. Many useful receptors are disclosed in the art, including those by Sujita Sukumaran, S., et al, Cancer Discov. 8, 972-87, (2018), and Vonderheide, R. H., et al, Immunol. Rev. 257, 7-13 (2014), including supplementary information, all methods and references therein, which are included herein.

Drug Carrier Aptamers and Aptamer TM.

A preferred category of flexible drug carriers and/or targeting moieties and biorecognition molecules or moieties in this invention are any suitable types of aptamer. All said definitions for aptamers include disclosures and all references from previously filed App. 62/786,340. Also included in this invention, with suitable modification, are all disclosures, examples and methods disclosed by inventor Sarah Shigdar, US Patent App. Publication; US 2018/0037892 A1, Dated Feb. 8, 2018; "Epcam Aptamers and Conjugates Thereof" (hereinafter "Shigdar"); and by inventors John J. Rossi, et al, U.S. Pat. No. 9,388,418, Dated Jul. 12, 2016; "Aptamer-mRNA Conjugates For Targeted Protein Or Peptide Expression And Methods For Their Use" (hereinafter "Rossi"); the entire contents of both are hereby incorporated herein, including all references therein, except for any conflicting definitions, subject matter disclaimers of disavowals, and except to the extent that the incorporated material is inconsistent or in conflict with the express disclosures herein, in which case the language in this disclosure controls.

Wherein said aptamers can function both as a suitable flexible drug carrier and as a suitable targeting moiety (TM), defined herein and can include a suitable "bifunctional aptamer" of Shigdar. Aptamers are generally single-stranded oligonucleotides or peptides that fold into well-defined three-dimensional shapes (i.e. secondary or tertiary structure) allowing them to bind to their targets with high affinity and specificity.

Most preferred for use as a flexible carrier and/or targeting moiety (TM), is the sequence of nucleotides, nucleic acids and/or amino acids that comprise the "biorecognition element" of said aptamers. Said biorecognition element of said aptamer can be a single strand or sequence of nucleic acids and/or amino acids, defined herein. Said biorecognition element can also be coupled at either end to additional nucleic acids and/or amino acids, or to carrier substances defined herein.

Under suitable conditions, said biorecognition element of said aptamer can be in the form of a secondary structure known in the art such as one or more suitable "loops" or folds, defined in this invention collectively as a "targeting moiety loop" or "TM loop". Said TM loop of nucleic acids or amino acids can be in the form of a hairpin loop, an internal loop, a bulge loop, a stem loop or combinations of these. Said TM loop can be of any suitable number or sequence of nucleotides, nucleic acids and/or amino acids, defined herein. Said TM loop can also be coupled at either end or at both ends to additional nucleic acids and/or amino acids, or to carrier substances defined herein, to provide a suitable "scaffold" for said TM loop. Said scaffold can include any suitable substance, including but not limited to, hybridized nucleic acid strands that form a "stem" or stem-like structure. Or, said scaffold can include, but is not limited to, any suitable amino acid or peptide strands or polymer that forms any suitable structure including, but not limited to, a "stem" or stem-like structure, a beta sheet, coil or coiled coil. Preferred aptamers include, but are not limited to, any aptamers useful as active agents (i.e. therapeutic agents) under suitable conditions.

Nucleic Acid Aptamers, ONs, ODNs and Peptide Aptamers.

Preferred aptamers useful as flexible carriers and/or targeting moieties (TM), for this invention, (including examples herein), with suitable modification, are any types of sense or antisense nucleic acids, oligonucleotides (ONs) and oligodeoxynucleotides (ODNs), peptide aptamers and aptamers chemically modified (i.e. modified backbone), using synthesis methods known in the art. All said definitions for aptamers for this invention include disclosures and all references from previously filed App. 62/786,340.

Said aptamers and/or ONs and ODNs can be suitably substituted for each other as needed and are suitably modified as needed to perform their intended function, for incorporation into said flexible carriers of this invention through synthesis of said carrier and/or through subsequent conjugation to said carrier substance or "scaffold", defined herein.

Preferred ONs and ODNs include suitable modification of sequences employed in various hairpin "beacons", biosensor and/or hybridization detection devices such as localized surface plasmon resonance (LSPR) for detecting gene mutations, such as human mutated p53 gene for cancer, among others.

Preferred aptamer and/or ON and ODN sequences useful against cancer in this invention are disclosed by Zhou, G., et al., Oncotarget 7,13446 (2016), including all references therein.

Useful p53 Gene Targeting ON, ODN and/or Nucleic Acid Aptamer Sequences.

A preferred group of aptamer sequences for this this invention are those that specifically bind to mutated proteins, mutated RNAs, mutated DNAs and genes found in cancer cells, including forms of p53 proteins, mRNAs and p53 genes. For example, Duan, R. Q., et al, Neoplasma 59, 348 (2012), disclose a corresponding one-base mismatch in human p53 gene sequence G→A at codon 175;

(5'-GTTGTGAGGCACTGCCCCCACCATG-3') (Seq ID No:26), that can be suitably modified and incorporated for use as an aptamer in this invention. Other useful ODN's and aptamer sequences are disclosed by Zhou, Z., et al, Anal. Chem. 90, 6468-6476 (2018) in a barcode system, Esteban-Fernandez, B., et al, Anal. Chem. 87, 2290-2298 (2015) capture probes in electrochemical DNA sensors, Farjami, E., et al, Anal. Chem. 83, 1594-1602 (2011) using electronic DNA hairpin molecular beacons, with TP53 gene-based DNA sequences that target a DNA sequence containing a single mutation, SNP at codon 175; a "long" TP53 DNA beacon (33-base);

5'-GAG GTC ATG GTG GGG GCA GCG CCT CAC AAC CTC-3', (Seq ID No:28), and/or a truncated TP53 DNA hairpin beacon (20-base), 5'-GT TGT GCA GCG CCT CAC AAC-3' (Seq ID No: 27), had a 5'-end amine modification (a 5'-amino-$C_7$-modifier) (Glen Research, Sterling, VA) and a C6-disulfide ($HO(CH_2)_6SS$ $(CH_2)_6$—) modification at the 3'-end. All references listed are incorporated herein, including all methods and supporting information and references therein.

Preferred aptamer and/or ON and ODN sequences are also disclosed by Soon, J. O., et al, Nucleic Acids Res. 33, No. 10 e90 (2005) and Olivier, M., et al, "The IARC TP53 Database: new online mutation analysis and recommendations to users." Hum. Mutat. 19, 607-614 (2002). The following Table lists useful nucleotide sequences (capture probe sequences), for use as, or within, targeting moieties including (TM-A), (TM-B), (TM-C), (TM-D), ((TM)$_R$), etc., of examples in this invention, to target mutated p53.

| Probe Name | Nucleotide Sequence (5'-3') | |
|---|---|---|
| 175 | GTT GTG AGG CNC TGC CCC | wherein N = A, T, or C (Seq ID No: 29) |
| 215 | TTT CGA CAT ANT GTG GTG GTG | wherein N = A, T, or C (Seq ID No: 30) |
| 216 | T CGA CAT AGT NTG GTG GTG CC | wherein N = A, T, or C (Seq ID No: 31) |
| 239 | C ATG TGT NAC AGT TCC TGC A | wherein N = G, T, or C (Seq ID No: 32) |
| 248 | C ATG AAC NGG AGG CCC ATC | wherein N = A, T, or G (Seq ID No: 33) |
| 273 | TT GAG GTG CNT GTT TGT GC | wherein N = A, T, or C (Seq ID No: 34) |
| 282 | G AGA GAC NGG CGC ACA G | wherein N = A, T, or G (Seq ID No: 35) |

All preferred aptamers, ON's and ODN's and preparation methods disclosed can be suitably modified for this invention and include, but are not limited to, any suitable functional group (phosphoramidites, amines and thiols and suitable spacers of nucleic acids and/or peptides and/or carbon atoms). Said aptamers and/or ON's and ODN's include, but are not limited to, any types of nucleic acid aptamers (i.e. DNA or RNA), peptide aptamers, or peptide nucleic acid (PNA), bi-specific aptamers, and aptamer sequences and synthesis methods including, but are not limited to, those disclosed by; Afonin, K A, et al, ACSNano 9, 251-259 (2015), for suitable DNA, RNA and hybrid duplex nanoparticles; Au, JL-S., et al, Adv Drug Deliv Rev. (2016) 97:280-301; Becker, R. C., et al, Thromb Haemost. (2005), 93(6): 1014-20;

Chen, L, et al, PNAS 112, 10002-10007 (2015), for useful RNA aptamers that bind mutated p53 protein, R175H-Apt, including RNA sequence ATTAGCGCATTTTAACAT-AGGGTGC (Seg ID No: 36);

Also Kotler, E., et al, Molecular Cell 71, 178-190, (2018), for a useful TP53 gene library that can be targeted with suitable TMs and Cohen, J. D., et al, Science 10.1126/science.aar3247 (2018) (including all supplementary information), for a reference list of names of mutations identified in primary tumors (Table S2) from a blood test applied to circulating tumor DNA (ctDNA)). Said mutations can be targeted (i.e. Target Substances), through respective nucleic acid sequences (and/or their complementary sequences), which are useful for inclusion in suitable aptamers and/or as Targeting Moieties in this invention (including examples herein);

| Cohen Table S2. Names of Useful Target Mutations. |
|---|
| AKT1 p.E17K, c.49G>A |
| APC p.E1306*, c.3916G>T |
| APC p.E1309*, c.3925G>T |
| APC p.E1309fs, c.3927delAAAGA |
| APC p.I1304fs, c.3910delA |
| APC p.I1311fs, c.3931insA |
| APC p.K1308fs, c.3924insA |
| APC p.N1455fs, c.4364delA |
| APC p.R1450*, c.4348C>T |
| BRAF p.D594G, c.1781A>G |
| BRAF p.F595L, c.1785T>G |
| BRAF p.I592V, c.1774A>G |
| BRAF p.V600E, c.1799T>A |
| CDKN2A g.21971208C>G (Splice Site) |
| CDKN2A g.21971209T>A (Splice Site) |
| CDKN2A p.D84H, c.250G>C |
| CDKN2A p.D84V, c.251A>T |
| CDKN2A p.E88*, c.262G>T |
| CDKN2A p.H83Y, c.247C>T |
| CDKN2A p.M54fs, c.161insTG |

-continued

| Cohen Table S2. Names of Useful Target Mutations. |
|---|
| CDKN2A p.R80*, c.238C>T |
| CDKN2A p.T77fs, c.231delCT |
| CTNNB1 p.G34E, c.101G>A |
| CTNNB1 p.G34V, c.101G>T |
| CTNNB1 p.I35S, c.104T>G |
| CTNNB1 p.S33C, c.98C>G |
| CTNNB1 p.S33F, c.98C>T |
| CTNNB1 p.S37C, c.110C>G |
| CTNNB1 p.S37F, c.110C>T |
| CTNNB1 p.S45A, c.133T>G |
| CTNNB1 p.S45F, c.134C>T |
| CTNNB1 p.S45P, c.133T>C |
| CTNNB1 p.T41A, c.121A>G |
| EGFR p.L858R, c.2573T>G |
| FBXW7 p.E471fs, c.1412insA |
| FBXW7 p.R367*, c.1099C>T |
| FBXW7 p.R465C, c.1393C>T |
| FBXW7 p.R465H, c.1394G>A |
| FBXW7 p.R465L, c.1394G>T |
| FBXW7 p.R479Q, c.1436G>A |
| FBXW7 p.R505C, c.1513C>T |
| FBXW7 p.R505G, c.1513C>G |
| FGFR2 p.P253R, c.758C>G |
| GNAS p.R201C, c.601C>T |
| GNAS p.R201H, c.602G>A |
| HRAS p.G13R, c.37G>C |
| HRAS p.G13V, c.38G>T |
| KRAS p.A146T, c.436G>A |
| KRAS p.A146V, c.437C>T |
| KRAS p.A59E, c.176C>A |
| KRAS p.A59T, c.175G>A |
| KRAS p.G12A, c.35G>C |
| KRAS p.G12C, c.34G>T |
| KRAS p.G12D, c.35G>A |
| KRAS p.G12R, c.34G>C |
| KRAS p.G12S, c.34G>A |
| KRAS p.G12V, c.35G>T |
| KRAS p.G13C, c.37G>T |

-continued

-continued

Cohen Table S2. Names of Useful Target Mutations.

KRAS p.G13D, c.38G>A

KRAS p.G13V, c.38G>T

KRAS p.Q61H, c.183A>T

KRAS p.Q61K, c.181C>A

KRAS p.Q61R, c.182A>G

NRAS p.G12D, c.35G>A

NRAS p.G13V, c.38G>T

NRAS p.Q61K, c.181C>A

NRAS p.Q61L, c.182A>T

NRAS p.Q61R, c.182A>G

PIK3CA p.E542K, c.1624G>A

PIK3CA p.E545A, c.1634A>C

PIK3CA p.E545D, c.1635G>C

PIK3CA p.E545D, c.1635G>T

PIK3CA p.E545G, c.1634A>G

PIK3CA p.E545K, c.1633G>A

PIK3CA p.E545Q, c.1633G>C

PIK3CA p.E80K, c.238G>A

PIK3CA p.E81K, c.241G>A

PIK3CA p.G1049R, c.3145G>C

PIK3CA p.H1047L, c.3140A>T

PIK3CA p.H1047Q, c.3141T>G

PIK3CA p.H1047R, c.3140A>G

PIK3CA p.M1043I, c.3129G>A

PIK3CA p.M1043V, c.3127A>G

PIK3CA p.N1044K, c.3132T>A

PIK3CA p.N345K, c.1035T>A

PIK3CA p.Q546K, c.1636C>A

PIK3CA p.Q546P, c.1637A>C

PIK3CA p.Q546R, c.1637A>G

PIK3CA p.R88Q, c.263G>A

PPP2R1A p.R183Q, c.548G>A

PPP2R1A p.R183W, c.547C>T

PTEN p.A126S, c.376G>T

PTEN p.C136R, c.406T>C

PTEN p.D92A, c.275A>C

PTEN p.G132S, c.394G>A

PTEN p.P96L, c.287C>T

PTEN p.P96S, c.286C>T

Cohen Table S2. Names of Useful Target Mutations.

PTEN p.R130Q, c.389G>A

TP53 g.7576927C>A (Splice Site)

TP53 g.7576927delC (Splice Site)

TP53 g.7577018C>A (Splice Site)

TP53 g.7577156C>T (Splice Site)

TP53 g.7577156C>T (Splice Site)

TP53 g.7577498C>G (Splice Site)

TP53 g.7578176C>A (Splice Site)

TP53 g.7578176C>G (Splice Site)

TP53 g.7578176C>T (Splice Site)

TP53 g.7578290C>A (Splice Site)

TP53 g.7578291T>G (Splice Site)

TP53 g.7578555C>T (Splice Site)

TP53 g.7578556T>A (Splice Site)

TP53 g.7579310A>G (Splice Site)

TP53 g.7579310A>T (Splice Site)

TP53 g.7579311C>A (Splice Site)

TP53 p.A138V, c.413C>T

TP53 p.A159D, c.476C>A

TP53 p.A159P, c.475G>C

TP53.p.A161T, c.481G>A

TP53 p.A276G, c.827C>G

TP53 p.A39fs, c.117insA

TP53 p.A63V, c.188C>T

TP53 p.A88fs, c.263delCCCCTGCACCAGC
(Seq ID No: 42)

TP53 p.C124*, c.372C>A

TP53 p.C135*, c.405C>A

TP53 p.C135F, c.404G>T

TP53 p.C135R, c.403T>C

TP53 p.C135W, c.405C>G

TP53 p.C141Y, c.422G>A

TP53 p.C176F, c.527G>T

TP53 p.C176G, c.526T>G

TP53 p.C176R, c.526T>C

TP53 p.C176Y, c.527G>A

TP53 p.C238R, c.712T>C

TP53 p.C242Y, c.725G>A

TP53 p.C275F, c.824G>T

-continued

-continued

| Cohen Table S2. Names of Useful Target Mutations. |
| --- |

TP53 p.C275Y, c.824G>A

TP53 p.D208N, c.622G>A

TP53 p.D259V, c.776A>T

TP53 p.D281H, c.841G>C

TP53 p.E11Q, c.31G>C

TP53 p.E171fs, c.513delGACGGAG

TP53 p.E180fs, c.540delCGCTGCCCCCACCATGAG (Seq ID No: 37)

TP53 p.E204*, c.610G>T

TP53 p.E221*, c.661G>T

TP53 p.E224fs, c.670insG

TP53 p.E258*, c.772G>T

TP53 p.E258G, c.773A>G

TP53 p.E258K, c.772G>A

TP53 p.E285K, c.853G>A

TP53 p.E286*, c.856G>T

TP53 p.E286fs, c.857delA

TP53 p.E286G, c.857A>G

TP53 p.E287*, c.859G>T

TP53 p.E298*, c.892G>T

TP53 p.E339*, c.1015G>T

TP53 p.E343*, c.1027G>T

TP53 p.E346*, c.1036G>T

TP53 p.E51fs, c.151delG

TP53 p,E62*, c.184G>T

TP53 p.F109V, c.325T>G

TP53 p.F113S, c.338T>C

TP53 p.F113V, c.337T>G

TP53 p.F134fs, c.400delT

TP53 p.F338fs, c.1014delC

TP53 p.G105C, c.313G>T

TP53 p.G105V, c.314G>T

TP53 p.G117fs, c.350insGGAC

TP53 p.G154fs, c.460delG

TP53 p.G154V, c.461G>T

TP53 p.G199fs, c.597insA

TP53 p.G199V, c.596G>T

TP53 p.G226fs, c.677delG

| Cohen Table S2. Names of Useful Target Mutations. |
| --- |

TP53 p.G244A, c.731G>C

TP53 p.G244V, c.731G>T

TP53 p.G245A, c.734G>C

TP53 p.G245C, c.733G>T

TP53 p.G245D, c.734G>A

TP53 p.G245S, c.733G>A

TP53 p.G245V, c.734G>T

TP53 p.G262V, c.785G>T

TP53 p.G266*, c.796G>T

TP53 p.G266E, c.797G>A

TP53 p.G266R, c.796G>A

TP53 p.G266V, c.797G>T

TP53 p.G279E, c.836G>A

TP53 p.G334R, c.1000G>C

TP53 p.G334V, c.1001G>T

TP53 p.H115fs, c.345insTTCTGGGACAGCCAAG (Seq ID No: 43)

TP53 p.H168R, c.503A>G

TP53 p.H179L, c.536A>T

TP53 p.H179R, c.536A>G

TP53 p.H179Y, c.535C>T

TP53 p.H193P, c.578A>C

TP53 p.H193R, c.578A>G

TP53 p.H193Y, c.577C>T

TP53 p.H214R, c.641A>G

TP53 p.I195fs, c.583insATCCGAGTGGAAGG (Seq ID No: 44)

TP53 p.I195fs, c.585insCCGAGTGGAAGGAT (Seq ID No: 45)

TP53 p.I195N, c.584T>A

TP53 p.I195T, c.584T>C

TP53 p.I251fs, c.753delC

TP53 p.I251V, c.751A>G

TP53 p.I254fs, c.761delCAT

TP53 p.I255F, c.763A>T

TP53 p.I255S, c.764T>G

TP53 p.K120R, c.359A>G

TP53 p.K132*, c.394A>T

TP53 p.K132E, c.394A>G

TP53 p.K132N, c.396G>C

-continued

| Cohen Table S2. Names of Useful Target Mutations. |
|---|

TP53 p.K132N, c.396G>T

TP53 p.K132Q, c.394A>C

TP53 p.K132R, c.395A>G

TP53 p.K132T, c.395A>C

TP53 p.K372fs, c.1114delA

TP53 p.K381fs, c.1141delA

TP53 p.K381fs, c.1141insA

TP53 p.L114*, c.341T>A

TP53 p.L130F, c.388C>T

TP53 p.L130V, c.388C>G

TP53 p.L137fs, c.410insTGG

TP53 p.L188fs, c.564delG

TP53 p.L194H, c.581T>A

TP53 p.L194P, c.581T>C

TP53 p.L194R, c.581T>G

TP53 p.L252fs, c.754delTCC

TP53 p.L257P, c.770T>C

TP53 p.L264fs, c.791delT

TP53 p.L264fs, c.792delCTA

TP53 p.L348*, c.1043T>A

TP53 p.L43fs, c.129delTG

TP53 p.L45fs, c.133insCTGT

TP53 p.M133L, c.397A>T

TP53 p.M237I, c.711G>A

TP53 p.M237K, c.710T>A

TP53 p.M44fs, c.130delA

TP53 p.N131fs, c.392delCAA

TP53 p.N131I, c.392A>T

TP53 p.N239S, c.716A>G

TP53 p.N288fs, c.862delA

TP53 p.N288fs, c.864insT

TP53 p.N345fs, c.1035insT

TP53 p.P142fs, c.424del ATGTTTTGCC AACTGGCCAAGACCTGCC (Seq ID No: 38)

TP53 p.P151fs, c.451insC

TP53 p.P152fs, c.454insCCGCCCGGCA (Seq ID No: 39)

TP53 p.P152L, c.455C>T

TP53 p.P177fs, c.531ins CCACCATGAG CGCTGCTCAGATAGCGATG (Seq ID No: 46)

-continued

| Cohen Table S2. Names of Useful Target Mutations. |
|---|

TP53 p.P190fs, c.570delCCT

TP53 p.P250L, c.749C>T

TP53 p.P278L, c.833C>T

TP53 p.P278S, c.832C>T

TP53 p.Q100*, c.298C>T

TP53 p.Q104*, c.310C>T

TP53 p.Q167*, c.499C>T

TP53 p.Q192fs, c.574delC

TP53 p.Q192H, c.576G>T

TP53 p.Q331*, c.991C>T

TP53 p.Q331Q, c.993G>A (Exon End)

TP53 p.Q38*, c.112C>T

TP53 p.R156fs, c.467delG

TP53 p.R158H, c.473G>A

TP53 p.R158L, c.473G>T

TP53 p.R174W, c.520A>T

TP53 p.R175C, c.523C>T

TP53 p.R175H, c.524G>A

TP53 p.R181P, c.542G>C

TP53 p.R196*, c.586C>T

TP53 p.R196fs, c.587insT

TP53 p.R209fs, c.626delAG

TP53 p.R213*, c.637C>T

TP53 p.R213Q, c.638G>A

TP53 p.R248fs, c.742delC

TP53 p.R248L, c.743G>T

TP53 p.R248P, c.743G>C

TP53 p.R248Q, c.743G>A

TP53 p.R248W, c.742C>T

TP53 p.R249G, c.745A>G

TP53 p.R249M, c.746G>T

TP53 p.R249S, c.747G>T

TP53 p.R267P, c.800G>C

TP53 p.R267W, c.799C>T

TP53 p.R273C, c.817C>T

TP53 p.R273H, c.818G>A

TP53 p.R273L, c.818G>T

TP53 p.R273P, c.818G>C

-continued

Cohen Table S2. Names of Useful Target Mutations.

TP53 p.R273S, c.817C>A

TP53 p.R280G, c.838A>G

TP53 p.R280I, c.839G>T

TP53 p.R280T, c.839G>C

TP53 p.R282G, c.844C>G

TP53 p.R282W, c.844C>T

TP53 p.R290H, c.869G>A

TP53 p.R306*, c.916C>T

TP53 p.R337L, c.1010G>T

TP53 p.R342*, c.1024C>T

TP53 p.S127F, c.380C>T

TP53 p.S127P, c.379T>C

TP53 p.S183fs, c.549insA

TP53 p.S215fs, c.644insGTG

TP53 p.S215I, c.644G>T

TP53 p.S240C, c.718A>T

TP53 p.S241F, c.722C>T

TP53 p.S260fs, c.778del
CCATCATCACACTGGAAGACT (Seq ID
No: 40)

TP53 p.S260Y, c.779C>A

TP53 p.S33fs, c.98insC

TP53 p.S94*, c.281C>G

TP53 p.T125fs, c.375 GTCTGTGACT
TGCACG>LLUN (Exon End) (Seq ID No: 41)

TP53 p.T125M, c.374C>T

TP53 p.T125T, c.375G>A (Exon End)

TP53 p.T125T, c.375G>C (Exon End)

TP53 p.T125T, c.375G>T (Exon End)

TP53 p.T155fs, c.463insA

TP53 p.T211fs, c.633insT

TP53 p.T211I, c.632C>T

TP53 p.T253P, c.757A>C

TP53 p.T256fs, c.767insCACT

TP53 p.T304fs, c.910del
CTGCCCCCAGGGAGCA (Seq ID No: 47)

TP53 p.V122fs, c.364delTG

TP53 p.V157F, c.469G>T

TP53 p.V157G, c.470T>G

TP53 p.V172F, c.514G>T

TP53 p.V173G, c.518T>G

-continued

Cohen Table S2. Names of Useful Target Mutations.

TP53 p.V197G, c.590T>G

TP53 p.V203fs, c.609del ATTTGCGTGTG
(Seq ID No: 48)

TP53 p.V216L, c.646G>C

TP53 p.V216M, c.646G>A

TP53 p.V272E, c.815T>A

TP53 p.V272fs, c.816insG

TP53 p.V272L, c.814G>C

TP53 p.V272L, c.814G>T

TP53 p.V272M, c.814G>A

TP53 p.V274F, c.820G>T

TP53 p.V31I, c.91G>A

TP53 p.W53*, c.158G>A

TP53 p. W53*, c.159G>A

TP53 p.W91*, c.273G>A

TP53 p. W91fs, c.271del GGCCCCTGCA
CCAGCCCCCTCCT (Seq ID No: 49)

TP53 p.Y126*, c.378C>G

TP53 p.Y163C, c.488A>G

TP53 p.Y205C, c.614A>G

TP53 p.Y205H, c.613T>C

TP53 p.Y220C, c.659A>G

TP53 p.Y234*, c.702C>A

TP53 p.Y234C, c.701A>G

TP53 p.Y234H, c.700T>C

TP53 p.Y234N, c.700T>A

TP53 p.Y234S, c.701A>C

TP53 p.Y236C, c.707A>G

TP53 p.Y327fs, c.981delT

*Coordinates refer to the human reference genome hg19 release (Genome Reference Consortium GRCh37, February 2009).

Also useful nucleotide sequences and/or aptamers that are included are disclosed in references herein:

Darmostuk, D., et al, Biotech. Adv. 33, 1141-1161 (2015), for useful SELEX methods for preparing aptamers for this invention; Guida, E., et al, Cancer Res 68, 6550 (2008), for useful peptide aptamer sequences prepared using yeast two-hybrid screening, that bind mutated p53 protein; Held, D. M., et al, Front Biosci. 11, 89-112 (2006); Hori, S-I, et al, Cancers 10, 9 (2018), and references and/or sequences therein, for the preparation of useful anti-cancer aptamers, for this invention;

Jeong, S., et al, Oligonucleotides 20, 155-161 (2010), RNA aptamers that bind mutant KRAS (v12) protein, including Aptamer II: 5'-CCG GAG UUG AGG CGU AGA UGG UUC AGA UCC GAA CGA UGA AG-3' (Seq ID No:50);

Joshi, P. J., et al, Curr Drug Targets Infect Disord. (2003), 3(4):383-400; Kim, M., et al, Molecules 23, 830 (2018), for review of useful aptamer conjugates, linkers, chimeric nanoparticle carriers; Laptenko, O., et al, Molecular Cell 57, 1034-1046 (2015), for DNA that binds the C-terminal domain (CTD) of p53 protein; Li, X. et al, J Cont. Rel. 171 (2013) 152-162; Marimuthu, C., et al, Analyst 137, 1307 (2012), for the preparation of useful DNA aptamers; Wang, Z-W, et al, Molec. Medicine Rep. 10, 1481 (2014), for synthesis of ssDNA aptamers using SELEX to target proteins, and references and/or sequences therein;

Ma, Y., et al, Angew. Chem. Int. Ed., 55, 3304-3308 (2016), and supporting information, for DNA hairpins and/or molecular beacons coupled to AuNPs that target telomerase in cancer cells;

MAWS Open Source Aptamer Software. Website: 2015.igem.org, DNA aptamer BBa_K1614021 binds p53 protein: 5'-AAG GTG GG-3'; Ni, S. et al, Int. J. Mol. Sci. (2017), 18, 1683; Nimjee, S. M., et al, Annu Rev Med. (2005), 56:555-83; Orava, E W, et al, ACS Chem. Biol. 8 (1), pp 170-178 (2013), for DNA aptamer synthesis and VR11 that binds TNF alpha on cancer cells;

Pan, Q., et al, J. Infection 1-16 (2018) (Elsevier Ltd), and references and/or sequences therein, for the preparation of useful aptamers against infectious disease organisms, for this invention; Patil, S. D., et al, AAPS J. (2005), 7(1):E61-77; Petraccone, L., et al, Curr Med Chem Anti-Cancer Agents 5, 463-75 (2005);

Saito, T., et al, DNA Cell Biol. (2005) 24(10):624-33; Sun, H. et al, Mol. Therapy-Nucleic Acids (2014) 3, e182; Tal, P., et al, Oncotarget 7, 11817 (2016), for useful peptide aptamer amino acid sequences prepared using phage display that bind mutated p53 protein;

Sharma, T K, et al, Biotech. Adv. 35, 275-301(2017), and references and/or sequences therein, for the preparation of useful DNA aptamers, including the use of unnatural nucleotides that possess amino acid-like side chains, for this invention; Yu, Y. et al, Int. J. Mol. Sci. (2016), 17, 358;

Cheng, Y, et al, PLOS One DOI: 10.1371, 1-20 (2016); DNA aptamer AS1411 binds nucleolin (NCL); 5'-d (GGTGGTGGTGGTTGTGGTGGTGGTGG)-3' (Seq ID No:51); Cheng, Y. et al, Chem. Sci., 8, 4571 (2017), for useful peptide-conjugated flexible drug carriers for this invention suitably adapted to provide TMs in the examples of this invention as targeted peptides (cNGR; CNGRC (Seg ID No: 52) and RGD), a cell-penetrating peptide (CPP; RRRR (Seq ID No:53)) and a nuclear localization "signal" or sequence (NLS) (i.e. RRRRK (Seq ID No:54)), which can specifically bind to a cell surface and effectively enter into the nucleus. Suitably, the multi-functional peptide delivery system (TCNT (Seq ID No:55), CNGRC-RRRRG-(Pra)-GRRRRK-RGD-NH$_2$ (Seq ID No:56)) is used as a TM as defined in the compositions and/or examples of this invention. Also Zhou, G., et al, Theranostics 7, 3948 (2017); and including all references therein which are hereby incorporated herein, among others. All references listed therein are incorporated herein, including all methods and supporting information and references therein. Target Substances for Applying Nanomechanical™ or Nanoforce™.

The mechanical forces useful for this invention include those derived from the energy in the dynamic, hydrodynamic, moving environment that exists in living organisms, including tissues, fluids and cells. All said definitions of target substances include disclosures and all references from previously filed Provisional App. 62/786,340.

The application of said Nanoforce™ to the carrier compositions of this invention is based on specific binding of said composition to suitable targeted or "Target Substances" or "Targets" and/or objects that can move in relation to each other. Therefore, the energy of said relative movement is transferred to said carrier compositions when said specific binding occurs.

Some examples of molecular mechanical forces useful in this invention are the shear forces and/or pulling forces, including hydrodynamic forces, between, or in relation to, moving fluids and biological bodies or substances. Other useful mechanical forces are those generated between moving (i.e. relatively mobile) biological bodies or substances and relatively stationary bodily structural substances or anchoring substances. Said mechanical forces are applied when the carrier and/or active agent, and/or Active Agent-NCS compositions, defined herein, of this invention are suitably bound through their respective TMs to and/or between said target substances defined herein. Target substances useful in this invention, with suitable modification as needed, are disclosed by, but not limited to, Bar-Zeev, M., et al, Drug Resist. Updates 31, 15-30 (2017); Friedlander, et al, Immunology Letters 116, 126-140 (2008); Wu, et al, Nature Biotech. 23, 1137-1146 (2005) and Teicher, et al, Current Cancer Drug Targets 9, 982-1004 (2009), which are incorporated herein, including references therein.
Plasma and Cellular Proteins.

Preferred plasma protein target substances or targets, include any suitable forms of albumins such as human serum albumins (HSA), albumin derivatives (i.e. fractionated, pegylated, methylated, etc.), any HSA derivatized with cis-aconitic anhydride (Aco-HAS) such as disclosed by, but not limited to, J A Kamps, et al, Biochim Biophys Acta. (1996) 1278 (2): 183-90, including references therein, any synthetic albumins and albumins and HSA derived from recombinant protein methods. Preferred plasma protein target substances include serum or plasma proteins including fibrinogens, globulins (gamma globulins, thyroglobulins), haptoglobins and intrinsic factor including their derivatives such as their pegylated forms.

Preferred cellular protein target substances include titins and fractions thereof, tubulins, actins, cellular receptors, peptide hormones, enzymes, (especially cell surface enzymes such as neuraminidases) and their derivatives such as their pegylated forms. Preferred cellular protein flexible carrier substances include any suitably flexible histones (such as histones I, II, III and IV, including fragments, sulfates and other derivatives thereof) and histones disclosed by C. Peterson, et al, IN; Current Biology, 14(14); R546-R551 (2004), including references therein.
Relatively Stationary Structural Substances.

For this invention, relatively stationary structural substances or anchoring substances, are preferred target substances for targeting moieties (TM) or specific binding moieties, defined herein. For example, the mechanical forces generated by the flow of circulatory fluids that include blood, plasma and lymph fluid, moving around and/or through more stationary or relatively stationary structural substances can be applied to the flexible carriers of this invention that bind to said anchoring substances. Said relatively stationary anchoring substances are defined as substances and/or structures with sufficient mass to provide suitable inertia against nanomechanical forces, defined herein. Said anchoring substances can include any suitable nanoparticles, defined herein, or components of said structural pathways that include structural substances (i.e. walls), of the circulatory system, arteries veins, lymph vessels, organs, tissues and between tissues and cells. Also included targets are cell surfaces, disease biomarkers and other substances that make up vessel walls (i.e. veins and capillaries), and/or linings of specific tissues and cells (i.e. endothelial cells, plaques), and specific substances that make up the extracellular matrix (EM) and substrates. Said mechanical, forces are suitably applied when the carrier and/or active agent compositions of this invention are bound through their respective TMs to and/or between said anchoring (structural) substances.

Circulatory Bodies.

Biological circulatory fluids transport and move circulatory bodies that are preferred target substances for specific binding moieties. Said circulatory bodies are relatively mobile, and include white blood cells (WBC), red blood cells (RBC), platelets, proteins and many other bodies and substances through said structural pathways. Other preferred circulatory bodies for targeting include cells or cell fragments including those with disease biomarkers or disease antigens including those of cancer cells, as well as bacteria, viruses, protozoa, fungi and other pathogens. Said movement of said circulatory bodies generates many useful forces, including shear forces between said circulatory bodies and/or between said circulatory bodies and the more stationary or relatively stationary structural substances or components, defined herein, of said structural or circulatory pathways or substrates. Said mechanical forces are applied when the carrier and/or active agent compositions of this invention are bound through their respective TMs to and/or between said circulatory bodies or between circulatory bodies and said anchoring substances.

Active Release Through Binding Circulatory Bodies.

In some embodiments, said active release carrier composition contains one or more TMs or specific binding moieties (i.e. antibody or aptamer), at a strategic location on said carrier, that will bind to one of said circulatory bodies, defined herein. Also, strategically located on said active agent or said active agent-NCS, is one or more TMs that will bind to one of said more stationary components or said structural anchoring substances, defined herein.

After binding, the carrier and active agent are held between two moving objects (targets) or between a moving object and a more stationary substance. Therefore, the mechanical force (i.e. shearing or pulling), generated between said objects will be transferred to said carrier and said active agent. The compositions of this invention are designed so that said mechanical force will separate said carrier from said active agent. After separation said active agent can be released from said TM or specific binding moiety.

In other preferred embodiments, said carrier and active agent will each have one or more TMs that will bind separately to said circulatory bodies and/or said intracellular substances or bodies. Therefore, after binding occurs, said carrier and active agent, or Active Agent-NCS, are held between said circulatory moving objects and said relatively stationary substance, defined herein, or between a moving intracellular object and a relatively stationary intracellular object, or membrane as described herein.

Extracellular and Cell Surface Target Substances.

Also useful as preferred target substances for TMs or specific binding moieties, defined herein, are the substances involved in the shearing and/or pulling forces generated by the movements between any extracellular substances. Extracellular substances are defined as cell surface or membrane substances, or cell wall substances, including relatively stationary cell products (anchoring substances), such as lipids, proteins, collagens, etc., that can make up the extracellular matrix (EM) itself. Extracellular substance can also include extruded cell substances including any suitable vesicles (i.e. exosomes) and movable (i.e. relatively mobile) substances moving between said EM and the cells and their cell surfaces, and/or in contact with said EM.

Preferred target substances for TMs of this invention include those on primary and metastatic tumor cells specifically. Tumor-specific targeting can be accomplished by incorporating affinity ligand peptides, such as those disclosed by Ruoslahti, E., Adv Drug Deliv Rev.110-111: 3-12 (2017), incorporated herein, including references therein.

Peptide ligands included are RGD peptide, iRGD (CRGDK (Seg ID No: 57)/RGPD (Seq ID No: 58)/EC), NGR peptide, folate, transferrin, and/or antibodies or aptamers against human epidermal growth factor receptor 2, transferrin receptor (TfR), including incorporation of an anti-TfR single-chain variable fragment (TfRscFv) as a targeting ligand as part of said TM. Also, include are aptamers that specifically bind the prostate-specific membrane antigen and nucleolin, among others.

Also useful as preferred targets for specific binding moieties are the extracellular substances involved in the shearing and/or pulling forces generated by the voluntary or involuntary movements between any cells, tissues and extracellular substances in muscles, bone, joints and tendons.

Also useful as preferred targets for TMs are the extracellular substances that are relatively mobile, involved in cellular mechanical forces such as those generated by cellular movement such as with cilia, pseudopods or with the rotary movement of flagella, among others.

Most preferred extracellular target substances are any specific, or mutated or abnormal forms of said extracellular substances or bodies that are released from, expressed on, or otherwise attached to the surface of specific cells or disease organisms. Also preferred extracellular target substances are any specific disease organisms, including viruses, latent viruses, bacteria, fungi, protozoans, arthropods, parasites and vermin, and any specific substances they may shed, including metabolic materials.

Said target substances would be recognized by specific binding with a targeting moiety, defined herein. Said specific or mutated forms include abnormal, diseased or unusual chemical structure or conformations, (i.e. disease marker substances), including fused, denatured or otherwise abnormal DNA, RNA or protein or carbohydrate or lipid molecules, abnormal proteasomes, abnormal mitochondria, abnormal filaments, abnormal spindles, centrosomes, endosomes, lysosomes, nucleus, nucleolus, endoplasmic reticulum, Golgi apparatus, peroxisomes or any other abnormal organelles or fragments thereof, including their respective membranes. Said preferred mutated forms also include abnormal, diseased or unusual chemical forms of said substances, such as abnormal deletions or additions (i.e. adducts) of nucleotides, residues or other moieties including abnormally high or low phosphorylations, methylations, carboxylations, aminations and thiolations. Preferred examples of target substances include, but is not limited to, those disclosed by Au, J. L.-S., et al, "Delivery of cancer therapeutics to extracellular and intracellular targets: Determinants, barriers, challenges and opportunities." IN; Adv Drug Deliv Rev. 97, 280-301 (2016); and Qiao, Y., et al, WIREs Nanomed Nanobiotechnol. e1527 (2018), for anti-cancer targeting substances and strategies useful in this invention and including those from all references therein, which are incorporated herein.

Intracellular Target Substances.

Other useful preferred target substances for TMs, aptamer TMs, or specific binding moieties defined herein, are the relatively mobile and/or relatively stationary substances (anchoring substances), involved in the mechanical forces including hydrodynamic forces that are generated by intracellular movement between intracellular bodies and/or membranes and other structures within the cell.

Intracellular substances that are preferred targets for specific binding moieties are intracellular substances that include fibrils, filaments (i.e. actin), microtubules (i.e. tubulin), mitochondria, smooth and rough endoplasmic reticulum, microsomes, golgi apparatus and other organelles, the nucleus, any suitable vesicles, enzyme or other protein complexes, and other suitable intracellular structures.

Other useful mechanical forces are those generated by intracellular movement between any suitable intra-nuclear bodies. Substances that are preferred targets for specific binding moieties are intracellular substances that include nuclear filaments, histones, RNA, DNA and chromosomes, among others.

Most preferred targets are any specific, or mutated or abnormal forms of said intracellular substances or bodies that would be recognized by specific binding with a targeting moiety, (i.e. Target Mutations), defined herein. Said specific or mutated forms include abnormal, diseased or unusual chemical structure or conformations, (i.e. disease marker substances), including fused, denatured or otherwise abnormal DNA, RNA or protein or carbohydrate or lipid molecules, abnormal proteasomes, abnormal mitochondria, abnormal filaments, abnormal spindles, centrosomes, endosomes, lysosomes, nucleus, nucleolus, endoplasmic reticulum, Golgi apparatus, peroxisomes or any other abnormal organelles or fragments thereof, including their respective membranes. Said preferred mutated forms also include abnormal, diseased or unusual chemical forms of said substances, such as abnormal deletions or additions (i.e. adducts) of nucleotides, residues or other moieties including abnormally high or low phosphorylations, methylations, carboxylations, aminations and thiolations. Preferred target substances include any mutated nucleic acids, DNA or RNA, or mutated proteins including point mutations in enzymes (i.e. kinases), tumor driver proteins (driver mutations), tumor suppressor proteins such as p53 (i.e. p53R175H) including, but not limited to, those disclosed by Bouaoun, L., et al, Human Mutations 37, 865-876 (2016); FROM: The International Agency for Research on Cancer, 150 Cours Albert Thomas, 69372 Lyon Cedex 08, France (IARC) TP53 Database (Website: "p53.iarc.fr" including those from references therein, also useful targets are mutated p53 proteins (i.e. G245, R175, R248, R249, R273, R282) and codons, etc., disclosed by Freed-Pastor, W A, et al, Genes & Development 26, 1268-1286 (2012) including those from references therein and hotspot mutations disclosed by Chang, M T, et al, Cancer Discov. 8 (2); 1-10 (2017) (including supplemental material, and website cancerhotspots.org), and including those from references therein, all of which are incorporated herein, among others.

Preferred examples of target substances also include, but is not limited to, those disclosed by Au, J. L.-S., et al, Adv Drug Deliv Rev. 97, 280-301 (2016) and any mutated nucleic acids and mutated proteins found in cancer as disclosed by Vogelstein, B., et al, Science 339, 1546-1558 (2013), and any suitable mutations accumulated in The Cancer Genome Atlas, (TCGA) and the International Cancer Genome Consortium (ICGC) data repositories, including those from references therein, which are incorporated herein, including the Universal Protein Resource for TP53 (uniport.org); among others. Also most preferred target substances are mutated or abnormal chromosomes, whether abnormal in their chemistry, or shape (i.e. fused or cleaved) or number (i.e. aneuploidy).

Also preferred intracellular target substances are any specific disease organisms, including viruses, latent viruses, bacteria, fungi, protozoans, arthropods, parasites and vermin, and any specific substances they may shed, including metabolic materials. Other substances that are preferred targets for specific binding moieties are intracellular substances that include any of the various membranes surrounding organelles and vesicles within a cell. Said mechanical forces are applied when the carrier and/or active agent compositions of this invention are suitably bound through their respective TMs to and/or between said intracellular substances.

Key Components of the Carrier Compositions of this Invention.

This invention discloses "flexible" or "Force Responsive™" drug carrier compositions including aptamers, defined as being capable of undergoing a conformational change ("shape shift"), when subjected to a suitable molecular, mechanical force, or Nanoforce™. Said drug carrier compositions also contain suitably coupled active agents and "therapeutic" active agents ("Drugs"), defined herein. When said suitable molecular mechanical force is applied, such as a binding force, separating force, pulling force, stretching force, unfolding force, rotating force, bending force, and/or combinations thereof, the carrier changes shape defined herein as a conformational change, from a "closed" form to an "open" form or shape, defined herein. Said flexible drug carrier contains, as part of its structure, or "within" it, various moieties or substances designed to provide a type of molecular, Force Responsive™ composition that can include a ligand, a "Binding Domain" and/or "hairpin" or "zipper" or zipper-like structure (motif), defined herein, that also suitably contains one or more suitable active agents. Said active agent(s) is (are) suitably covalently coupled (i.e. by a cleavable linkage), or noncovalently coupled, as defined herein, to said flexible drug carrier. When said flexible carrier is in its closed form, said active agent (or said cleavable linkage), is suitably sequestered or sterically hindered from being released (or cleaved), from the carrier (i.e. "steric zipper").

Throughout the disclosures and examples for various embodiments of this invention, said flexible carrier and said binding domain, can include several useful forms and substances suitable to perform its intended function. In certain preferred embodiments, said Binding Domain is defined to also mean a "Ligand Binding Domain" (LBD) capable of binding specific chemical ligands ("bindable ligand"), that is comprised of, or are part of, a new type of biocleavable or cleavable linkage designated as a "Cleavable Ligand Linkage™" (CLL) or Ligand Protected Linkage™ (LPL), moiety, defined herein. In other preferred embodiments, said active agent can function as said ligand and is coupled through said CLL. Or, wherein said CLL is itself (i.e. also functions as), or includes as a moiety, a suitable, "bindable ligand", defined herein.

In another preferred embodiment of this invention said binding domain can suitably bind to any type of "Noncovalent Coupler Substance" (NCS), defined herein, or to any "Active Agent NCS", defined herein, including said "Intercalator Coupled Active Agent", defined herein. In said intercalator coupled active agent, the active agent is coupled through an intermediate intercalator to said "Binding Domain" or "Zipper" section of said carrier nucleic acid (Carrier NA), defined herein.

In other preferred embodiments, said Binding Domain is defined to also mean a "Hapten Binding Domain" (HBD), that functions as an antigenic binding site (i.e. epitope), of any antibody or Fab fraction, defined herein, capable of binding any suitable moiety (i.e. "bindable hapten" or paratope), defined herein.

In this invention said bindable ligand and said Ligand Binding Domain are coupled noncovalently to each other through well-known "host-guest" chemical forces. In another preferred embodiment with suitable conditions, Said CLL can be itself (i.e. also functions as), or includes as a moiety, any suitable, bindable hapten (i.e. paratope), defined herein as capable of being coupled with said HBD, defined herein.

Preferred flexible carrier embodiments also include two or more molecular sequence "strands" that are suitably held together reversibly by noncovalent forces to form said zipper or hairpin. Said forces are preferably due to well-known noncovalent molecular or intermolecular attractive forces in suitably aqueous media, including electrostatic interaction of ions or of ionic groups, hydrogen-bonding, attraction by a hydrophobic effect, and van der Walls forces, among other forces known in "host-guest" chemistry.

Said drug or other active agent is coupled in such a way that no significant amount of the drug can be released until said mechanical force causes a conformational change (i.e. strand separation or "unzipping"), within the flexible carrier.

Preferred substances within said flexible carrier that provide said zipper include, but are not limited to, strands of nucleic acids, amino acids, lipids, carbohydrates, any suitable polymers, and combinations thereof. For instance, suitable complementary sequences of nucleic acids can form a "closed" nucleic acid duplex carrier "zipper" capable of carrying one or more active agents, or intercalators, as defined herein.

Also, suitable sequence strands of amino acids can form useful zipper structures by intermolecular forces disclosed herein, including folding through the hydrophobic effect between sequence strands containing suitable hydrophobic amino acids (such as alanine, valine, leucine, isoleucine, phenylalanine, tryptophan and methionine). Said active agents are covalently or noncovalently coupled, as defined herein, to said zipper sequences so that they are suitably prevented from being released in their closed form.

A key component of this invention includes at least one drug or other active agent, defined herein, that is covalently coupled to, or noncovalently entrapped within, said flexible drug carrier and/or said Binding Domain, defined herein, in its closed form.

In a preferred embodiment, said active agent is covalently coupled through a cleavable linkage (CL), defined herein, within said carrier in its closed form. Said covalently coupled cleavable linkage of said active agent, is suitably sequestered and/or sterically hindered, within said carrier, from being exposed to any significant cleavage. Said covalently coupled cleavable linkage can be suitably coupled directly to said carrier, wherein said active agent is also directly coupled to said carrier. Or, said cleavable linkage can be covalently coupled indirectly through a "noncovalent coupler substance" (NCS), defined herein, wherein said active agent is also indirectly coupled to said carrier.

In either embodiment, the drug is prevented from being released from the carrier until said suitable molecular mechanical, or Nanomechanical™ force or Nanoforce™ is applied. Said coupling is designed so that the active agent cannot be released from the carrier in any significant amount until there occurs specific binding with one or more of the intended target substances, defined herein, by one or more said targeting moieties (TM), defined herein, that are coupled to said carrier and/or active agent.

Another preferred embodiment of this invention includes at least one covalently coupled targeting moiety (TM), which can be an integral part of said flexible carrier (i.e. aptamer) and/or Binding Domain, defined herein, and includes targeting molecules, biorecognition molecules, antibodies and specific binding moieties and ligands, defined herein, that are capable of binding to ("targeting") a specific target substance, defined herein, including antigens, viruses, disease microorganisms, disease biomarkers including cancer biomarkers and mutated proteins and nucleic acids, defined herein. Said disease biomarkers include any suitable biomarkers including those disclosed by Hudson, et al, in Nature Med. 9, 129-134 (2003), Rabbitts, et al, Nature Med. 9, 383-386 (2003) and the contents and references therein which are incorporated herein. Examples of said TM include any suitable antibodies, Complementarity-Determining Regions (CDR loops), anticalins, enzymes, TALENs, zinc finger proteins, clustered regularly-interspaced short palindromic repeats (CRISPR) mechanisms, receptor binding proteins, nucleic acids and aptamers, defined herein.

Specifically for embodiments of this invention that employ active release, said active agent also has coupled to it (directly or indirectly, as defined herein), at least one targeting moiety (TM), defined herein. In the compositions of this invention, said coupling is designed so that said active agent, or the linkage used for coupling said agent to said TM, is wholly or partially sequestered (or sterically hindered) by said carrier in its closed shape or form.

For all embodiments of this invention, the composition is designed so that the force used to cause said change in conformation of said flexible carrier from closed to open, defined herein, is suitably less than that of the binding forces between any said TM (i.e. aptamer), and their specific targets. For any embodiments in this invention containing more than one aptamer or TM coupled to said carrier or to said active agent, said nanomechanical or Nanoforce™ or unzipping force used for opening said carrier, is designed to be suitable (i.e. less than) compared to the combined binding forces of said multiple TMs.

Flexible Force Responsive Carrier Compositions.

In a suitable in vivo or in vitro environment, said "flexible" drug carrier composition is capable of binding to one or more specific target substances. Said binding triggers the application of a suitable Nanoforce™, defined herein, such as an allosteric binding force or a pulling force, causing the carrier to change shape from a closed form to an open form. Said change in shape causes the eventual release of the active agent from the flexible carrier.

The arts of synthesizing nanoparticles, polymers, nucleic acids, antibodies and/or other protein and peptides have known methods for designing molecules with the desired physical, chemical and flexible properties of this invention. For synthesizing the compositions of this invention, the carrier substances, binding moieties and other substances with the desired properties of binding affinities, molecular mass, energies needed for conformational change, flexibility, etc., can be selected from existing substances and incorporated into the compositions of this invention, or they can be designed and synthesized de novo, using well known skills in the art and made suitable to perform their intended function.

In certain preferred embodiments, said drug carrier and one or more targeting moieties can be suitably synthesized by well-known chemical methods. The flexible carrier can be any suitable molecular substance such as a peptide, protein, nucleic acid or polymer. The carrier can also include any suitable macromolecular substance, such as a liposome, micelle, nanoparticle, molecular aggregate or dendrimer.

Conformational changes are well known in the art of peptides, proteins, nucleic acids and polymers that can be useful in the compositions and for the applications of this invention.

The drug carrier substances of this invention are divided into categories of suitable substances that include nucleic acids, peptides, proteins, carbohydrates, polymers, grafted polymers, foldamers, nanoparticles and amphiphilic molecules as disclosed herein. The carrier composition can include a biodegradable, or biocleavable, or cleavable linkage between the active agents and the carrier substance and can include an intermediate substance, defined herein, between said carrier and said active agents. Also, one or several moieties are coupled to the carrier that include targeting molecules, active agents and transduction vectors disclosed herein to provide other desirable properties. Any suitable synthesis method used for preparing polymers conjugated to various moieties, with suitable modification, is useful for synthesizing the compositions of this invention.

For use as drug carriers, any suitable nanoparticles and any copolymers and grafted polymers such as dextran, poly lactides, poly (dl-lactide/glycolide) polymers, N-(2-hydroxypropyl) methacrylamide (HPMA) or polyethylene glycol (PEG) are commercially available with suitable molecular weight (MW), and/or can be suitably modified for this invention. Based on their molecular size, they are arbitrarily classified into low molecular weight (MW<20,000) and high molecular weight (MW>20,000). Preferred polymers are of a molecular weight suitable for use in a closed form and capable of being changed to an open form through Nanomechanical™ force as described herein. A carrier MW of 20,000 or greater is preferred when the purpose is to prevent rapid elimination of the carrier due to renal clearance. The carrier-active agent compositions in this invention overcome many limitations for delivering active agents in the prior art and thereby provides new properties and unexpected advantages.

The flexible, force responsive drug carrier substances or compositions of this invention are suitably nano-sized, macromolecular or molecular sized carrier compositions that are defined for this invention as "flexible" in that they are capable of a force-induced physical change in shape, form or size as defined herein. The carrier substances also include at least one specific binding moiety, targeting moiety or biorecognition molecule or ligand, as defined herein, covalently coupled to the carrier and capable of binding to its intended target substance, or biomarker, defined herein.

Closed Form Versus Open Form of the Drug Carrier Composition.

For the purposes of all embodiments of this invention, said flexible, Force Responsive™ carrier composition is defined here as a "closed" carrier composition, (i.e. sterically closed shape), when all or part of said moieties (ligands, Binding Domains, "hairpins" or "zippers" or zipper-like structures (motifs), defined herein) within said carrier are suitably bound or coupled to provide protection from release of said active agent. When said moieties within said carrier are so bound, said closed composition provides a sterically hindered environment for any coupled active agent and/or any cleavable linkage (CL), between said active agent and said carrier. Therefore, due to the size, shape, motif or molecular conformation of the carrier, an active agent suitably coupled to said closed carrier cannot suitably or significantly, be released or said cleavable linkage, suitably cleaved from the composition.

Conversely, said carrier composition is defined here as an "open" carrier composition (i.e. sterically open shape) when, due to a change in the size, shape, motif or molecular conformation of the carrier, said active agent or CL, coupled to said carrier is thereby exposed (no longer sterically hindered) and can be released from the composition.

Said release of said active agent is due to the separation or unbinding of said moieties within said carrier to allow opening of said carrier, induced or initiated by specific binding of the carrier and/or said active agent through their respective targeting moieties to their intended target substances. Said specific binding induces or initiates suitable allosteric, nanomechanical forces, or Nanoforce™, causing the separation of said moieties within said carrier to allow release of said active agent, defined as a physical change or shift in the carrier's shape, size or conformation from a closed form to an open form, as defined herein. Depending on the type of linkage as defined herein, said cleavage can then occur through several suitable chemical methods including reduction, hydrolysis or enzymatic action, including proteolysis.

Coupling Active Agents to the Flexible Drug Carriers.

Flexible Drug Carriers with Covalently Coupled Active Agents.

In all said preferred embodiments of this invention of flexible carrier nucleic acid, including aptamer nucleic acid and peptide aptamer compositions, the flexible carrier substance contains in its composition (or is covalently coupled to), at least one, specific targeting moiety, TM, as defined herein.

In preferred embodiments of the invention, said active agents and "therapeutic" active agents ("Drugs"), are covalently coupled to said flexible drug carrier compositions. Under suitable conditions, said coupling can include a suitable intermediate substance between said carrier and said active agents, that provides multiple sites for said coupling. Said intermediate substance can include any suitable polymers, protein, peptide, nucleic acids and/or combinations of these, defined herein. Said active agent coupling is through a covalent linkage or bond that is a chemically cleavable (i.e. biocleavable) linkage (CL), as defined herein. And wherein, said cleavable linkage between the active agent and said carrier is suitably protected from chemical cleavage (i.e. sterically hindered), by physical and/or steric conditions due to the closed form of the carrier. For the purposes of this invention, said suitably protected linkage can be the result of the linkage (and suitably the active agent), being sequestered, or sterically protected from cleavage within the closed form of the carrier.

In said covalently coupled compositions, after the carrier has been allosterically and/or nanomechanically forced to shift from a closed form or shape to an open form or shape, said cleavable linkage will be exposed. With the carrier forced into its open form, suitable chemical reactions (i.e. cleavage of linkages) may then proceed to release said active agent.

Flexible Carriers with Noncovalently Coupled Active Agents.

Other preferred carrier compositions of this invention have the active agent ("Drug"), noncovalently coupled, as defined herein, directly or indirectly, as defined herein, to the flexible carriers of this invention. Said noncovalently coupled active agents and/or NCS, are defined as coupled or contained by forces that can include any combination of physical entrapment, steric hindrance and/or other noncovalent coupling forces, including hydrophobic forces, defined herein.

Intercalator Active Agent

A preferred type of said noncovalently coupled active agent in this invention is any active agent that can noncovalently bind to said flexible carrier, including any said intercalator and/or major groove or minor groove binding moiety, defined herein, that is also the active agent. In said "Intercalator Active Agent", the active agent is coupled through any suitable intercalation or "Ligand Binding Domain" or "Binding Domain" or "Zipper" section of said carrier nucleic acid (Carrier NA), defined herein, such as a carrier aptamer, defined herein. Said Carrier NA or peptide aptamer can be suitably folded upon itself to form a suitable binding domain "zipper", or can be composed of two complementary strands that form said zipper-like form. The noncovalently coupled active agent is closely bound to, or entrapped within, the closed carrier of this invention.

Active Agent-TM Composition.

In another preferred type of carrier composition, the flexible carrier substance contains (i.e. has covalently coupled to it), at least one, and preferably more than one, specific targeting moiety, or aptamer targeting moiety (TM), as defined herein.

Also, said composition includes a suitable noncovalently coupled active agent, that can noncovalently bind to said flexible carrier, including said "Intercalator Active Agent", defined herein. And wherein said active agent is suitably covalently coupled through a suitable cleavable linkage, as defined herein, to at least one specific TM or biorecognition molecule or ligand, as defined herein, and is designated an "Active Agent-TM Composition" or "Active Agent TM". And, preferably, said TM can bind to a target substance or biomarker of different or similar specificity than said TM coupled to said carrier. Said Active Agent-TM is noncovalently coupled to, or entrapped, or sterically hindered within, the closed carrier of this invention.

Therefore, said Nanomechanical™ forces, defined herein, can be applied to both said flexible carrier substance and to said Active Agent-TM, through their respective specific targeting moiety, targeting moiety or biorecognition molecule or ligand, as defined herein, to induce a conformational change from closed to open, as defined herein. Preferably, said conformational change includes the pulling apart of said Active Agent-TM from said flexible carrier.

Active Agent-Noncovalent Coupler Substance (Active Agent-NCS).

In some preferred embodiments of this invention, said active agent ("Drug"), is not in itself, suitable for noncovalent coupling to a flexible carrier. In this embodiment, any suitable active agent can be suitably noncovalently coupled indirectly to said flexible carrier through a suitable "noncovalent coupler substance" (NCS), that includes any suitable intercalators, defined herein, to provide an "active agent coupled NCS" (Active Agent-NCS), defined herein. Preferably, said coupling between said active agent and said NCS is a cleavable linkage (i.e. self immolative), as defined herein. Suitably, for the carrier nucleic acids and aptamers of this invention, said NCS is any suitable intercalator, defined herein.

Another preferred embodiment of this invention is any type of Active Agent-NCS wherein said NCS moiety is a suitable intercalator to provide an "Intercalator Coupled Active Agent". In said intercalator coupled active agent, embodiment, the active agent is coupled through an intermediate intercalator to a carrier nucleic acid (Carrier NA), such as a carrier aptamer, that contains two hybridized strands or a single strand suitably folded upon itself to form a suitable binding domain "zipper" for said intercalation.

Said intercalator with coupled active agent suitably and specifically can bind noncovalently to double stranded nucleic acid in certain hybridized sequences (i.e. double stranded DNA, duplex DNA) used in the Carrier NA or carrier aptamer.

In any case, said Active Agent-NCS is sufficiently strongly bound to said flexible carrier through suitable noncovalent forces, defined herein, wherein said NCS functions as an intermediate binding substance to noncovalently couple said active agent to said closed flexible carrier. In addition, while said Active Agent-NCS is suitably intercalated, or bound to a "Binding Domain" or "Zipper" section of said flexible carrier (i.e. carrier is closed), said cleavable linkage between said active agent and said NCS is sterically hindered and not subject to any significant cleavage. Said NCS can be coupled to more than one active agent, and can be any suitable substance, including, but not limited to, ligands, proteins, peptides, polypeptides, nucleic acids, any intercalators, major or minor groove binding substances, carbohydrates, lipids, adamantanes and amphiphilic substances, and their derivatives, as defined herein.

Upon release of said Active Agent-NCS from said flexible carrier (i.e. carrier is open), said cleavable linkage between said active agent and said NCS is no longer sterically hindered and can be cleaved through various known methods, defined herein, to release the original or unmodified active agent.

Flexible Carriers with Active Agent-NCS-TM Composition.

Another preferred embodiment of this invention is a flexible carrier composition, that contains in its structure, or is suitably coupled to, one or more specific targeting moieties (TM), defined herein, capable of binding to their intended target substances. And wherein said carrier also contains an active agent ("Drug") composition, that is composed of three moieties. Said active agent composition contains a suitable active agent (moiety 1), suitably coupled to a NCS, defined herein (moiety 2), by a suitable cleavable linkage, as defined herein, to provide an Active Agent-NCS, defined herein.

Also, in this embodiment, said NCS (moiety 2) of said Active Agent-NCS is also suitably coupled (independently from said active agent), by a suitable covalent linkage, (with or without spacer, as defined herein), to at least one specific targeting moiety (TM), (moiety 3), as defined herein, capable of binding to its intended target substance, or biomarker.

Therefore, said NCS moiety 2, is suitably coupled independently to two other moieties: (1) said active agent and (3) said specific targeting moiety (TM), to provide an Active Agent-NCS-TM composition, and wherein each moiety can perform its intended function. Said coupling of said NCS moiety to said carrier is by noncovalent coupling to a "Binding Domain" or "Zipper" section of said carrier, such as by intercalation, or is entrapped within, or sterically hindered within, the closed carrier of this invention. Preferably, said Active Agent-NCS-TM can include more than one active agent coupled to said NCS moiety. Also, preferably, any said TM coupled to said NCS can bind to a target substance of different or similar specificity than any said TM coupled to said carrier and at strategic sites on said carrier or said NCS, there can be one or more TMs.

In said carrier composition, said Nanomechanical™ forces, defined herein, can be applied to both the flexible carrier substance and to said Active Agent-NCS-TM, through specific binding of their respective TMs, as defined herein, to induce a conformational change from closed to open, as defined herein.

Useful Intercalators.

Intercalators specific for double stranded DNA and other nucleic acids, that are useful for this invention after suitable modification, are defined herein and disclosed in application SN #878,175, filed Jun. 28, 2004. The following references are also incorporated herein, including references therein: Blank, et al, (2003) PNAS, 100, 11356; Rief, M., et al, (1999) Nat. Struct. Biol. 6, 346-349; Essevaz-Roulet, B., et al, (1997) Proc. Natl. Acad. Sci. USA 94, 11935-11940; Bockelmann, U., et al, (1997) Phys. Rev. Lett. 79, 4489-4492. Strunz, T., et al, (1999) Proc. Natl. Acad. Sci. USA 96, 11277-11282; Clausen-Schaumann, H., et al, (2000) Biophys. J. 78, 1997-2007; Williams, M. C., et al, (2001) Biophys. J. 80, 1932-1939.

Flexible Carrier Substances and Compositions.

The present invention is a composition comprised of one or more active agents covalently or noncovalently coupled to a flexible carrier substance or "flexible carrier". Preferably the flexible carrier substance also provides or contributes to a biocompatible framework, scaffold or "backbone" to which are coupled various moieties. For the purposes of this invention, a flexible carrier substance is defined as a flexible, molecular, macromolecular or nano sized substance suitable for pharmaceutical or diagnostic use that is one of the materials used to synthesize the new flexible carrier compositions of this invention.

This does not include certain adjuvants or so called pharmaceutical "carriers" or "drug vehicles" defined as pharmaceutical mixtures of solvents, dispersing agents, surfactants, excipients, or their combinations, that comprise a usually aqueous formulation for containing a drug or agent. However, a flexible carrier composition of this invention may include a chemically modified form of a specific substance that has been used in such pharmaceutical mixtures. Also, a flexible carrier composition of this invention may be a useful additive to certain pharmaceutical mixes.

Other embodiments of the carrier compositions of this invention include the use of specific enzymes and other proteins generally used in the art of gene editing that includes TALENs, zinc finger proteins and any suitable "clustered regularly-interspaced short palindromic repeats" (CRISPR) proteins. Said proteins are disclosed by: Adli, M. Nature Comm. 9, 1911, DOI: 10.1038; s41467-018-04252-2 (2018), Aparicio, T., et al, DNA Repair 19, 169-175 (2014), Baliou, S., et al, Internat. J. Oncology 53, 443-468 (2018), Ferry, Q R V, et al, Nature Communications 8:14633, DOI: 10.1038; ncomms14633 (2017), Nowak, C M, et al, Nucleic Acids Research, Vol. 44, 9555-9564 (2016), Jubair, L., et al, Molecular Therapy: Nucleic Acids 8, 56 (2017), Liu, J., et al, PLOS ONE 9 (1), e85755; doi:10.1371 (2014), Pawelczak, K S, et al, ACS Chem. Biol. 13, 389-396 (2018), Shao, S., et al, Nucleic Acids Research, Vol. 44, No. 9 e86 (2016), Teng, F., et al, Genome Biology 20, 15 (2019) doi.org; 10.1186 s13059-019-1620-8; including all methods and references therein.

The flexible carrier substances of this invention are limited by category to a variety of suitable substances including proteins, nucleic acids, carbohydrates, grafted polymers and surfactants disclosed herein. The flexible carrier substance can also include combinations of these suitable substances.

Flexible Carrier Aptamers.

For this invention, all examples and references to specific aptamers and other scaffolds are meant to include the nucleic acid and/or the amino acid sequences that provide the specific binding properties (i.e. targeting moiety, TM), suitable carrier properties and/or allosteric properties of said aptamer or scaffold and may or may not include other sequences disclosed in said examples when suitably incorporated and/or modified for use in this invention. The design and synthesis of aptamers is well known in the art. Said aptamer can be in any suitable shape including the form of a strand, a fold, and/or a stem and/or a loop of nucleic acids or amino acids that can be in the form of a hairpin loop, an internal loop, a bulge loop, a stem loop or combinations of these. All said definitions for aptamers include disclosures and all references from previously filed App. 62/786,340.

Preferred flexible carrier aptamers in this invention also provide a targeting moiety and include any suitable peptide aptamers or nucleic acid aptamers, as defined herein. Preferred nucleic acid flexible carrier aptamers in this invention include any suitable DNA or RNA aptamers, including, but not limited to, Derivatized Nucleic Acid Aptamers; Mixed Backbone Nucleic Acid Aptamers; Capped Nucleic Acid Aptamers; Hybrid Nucleic Acid Aptamers and Chimera Nucleic Acid Aptamers; as defined herein.

Aptamers with Protamines.

Under suitable conditions, protein substances that can be used with the aptamers of this invention include any suitable protamines including human, fish (i.e. salmines and clupeines), bovine or other animal or plant protamines including fragments, sulfates and other derivatives thereof (i.e. fractionated, pegylated, methylated, etc.), any synthetic protamines and protamines derived from recombinant protein methods. Also included are low MW protamines including any from enzymatic digestion as disclosed by Y. Byun, et al, IN; Thromb. Res. 94; 53-61 (1999), protamine-like proteins disclosed by J. D. Lewis, et al, IN; Biochem. Cell Biol., 80(3); 353-61 (2002), protamines disclosed by J. D. Lewis, et al, IN; Chromosoma, 111 (8); 473-82 (2003) and by K. W. Park IN; Int. Anesthesiol. Clin., 42(3); 135-45 (2004), including references therein. Also preferred is any suitable protamine that is suitably derivatized to provide a carboxylated flexible carrier substance by reacting it with acetic (or succinic) anhydride in anhydrous solvent.

Aptamers with Noncovalent Coupling Proteins, Other Structural Domains and Zinc Fingers.

Under suitable conditions, protein substances that can be used with the aptamers of this invention include noncovalent coupling proteins which include avidins, NeutrAvidins, streptavidins, staphylococcal protein A, protein G, protein N and their fragments and derivatives including pegylated forms. Avidins and streptavidins are preferred for noncovalent coupling to any suitable biotinylated substance including active agents and active agents through avidin-biotin linkage. Under suitable conditions, other protein substances that can be used with the aptamers of this invention include, but are not limited to any suitably modified protein structural domains listed or referenced herein.

Also included are ZnF GATA domain-containing proteins or peptides that can bind to the DNA sequence [T]GATA[A] (Seq ID No:59); [T]GATA[G] (Seq ID No:60); [A]GATA [A] (Seg ID No: 61); [A]GATA[G] (Seq ID No:62); of promoters. Zinc fingers are small protein structural motifs that can coordinate one or more zinc ions to help stabilize their folds. They are classified into several structural families and can function as interaction modules that bind DNA, RNA, proteins or small molecules.

Flexible Antibody-Like Scaffolds, Carrier Peptide and Polypeptide Substances.

Under suitable conditions, antibody-like scaffolds are defined as proteins, peptides, polypeptides, hydrocarbon-stapled α-helical peptides and protein substances that can be used as flexible carriers, Ligand Binding Domains (LBDs) and with the aptamers of this invention. They include any suitable di-, tri-, poly-peptides and proteins including dilysines, trilysines, transduction vectors, peptide foldamers, lasso peptides including suitably modified microcins, capistruins and domains thereof and receptor binding peptides defined herein. In certain preferred examples, the active agents and/or intercalators of this invention are coupled to the amphipathic peptide KALA (Seq ID No:63) as disclosed by T. B. Wyman, et al, Biochem. 36, 3008-3017 (1997), and may include derivatives and added moieties as disclosed herein.

Under suitable conditions, antibody-like scaffolds, carrier proteins, LBDs and polypeptide substances that can be used with the aptamers of this invention include, but are not limited to, any suitable polypeptides or proteins and derivatives and domains or "motifs" thereof (i.e. drug binding domains), that have a suitable flexible conformation for changing shape, as defined herein, such as the alpha helix, which is the most common form of regular secondary structure in proteins. Under suitable conditions, carrier antibody-like scaffolds, polypeptide and protein substances that can be used with the aptamers of this invention include any suitable alpha helix, beta strand or beta sheet (also beta-pleated sheet) which generally consists of beta strands of peptides (i.e. amino acid residues) connected laterally by five or more hydrogen bonds, forming a generally twisted, pleated sheet. A suitable beta strand is a sequence of amino acids typically 5-10 amino acids long whose peptide backbones are capable of being almost fully extended.

Also preferred are any suitably flexible antibody-like scaffolds, carrier peptide, polypeptide or protein secondary structures including LBDs, Binding Domains and derivatives thereof, that form flexible dimers, trimers or interdomain "sandwich" forms, helical forms, zipper forms, including, but not limited to, suitable "nucleotide binding sites" (NBS), in Fab fragments, as disclosed by Mustafaoglu, N., et al, Langmuir 31, 9728-9736 (2015), and references included therein, and combinations thereof. Said "nucleotide binding sites" for this invention are also defined as "nucleotide binding domains" and "Binding Domains". Said flexible secondary structures can be held together by well-known "Host-Guest" chemical forces that include hydrogen bonds, ionic bonds, salt bridges, van der Waals forces and lipophilic forces including leucine zippers, phenylalanine stacking and "steric zippers".

Aptamers Coupled with Carrier Grafted Polymers.

A grafted polymer is a category of carrier substances and suitable intermediate substances defined as a polymeric substance suitable for pharmaceutical, diagnostic or agricultural use including copolymers and block polymers such as diblock or triblock copolymers prepared from a variety of monomers that are suitably coupled to produce a flexible carrier substance as defined in the present invention. Grafted polymers and copolymers can introduce other desirable properties such as a positive or negative net charge and hydrophobic properties.

Said grafted polymers can be appropriately end capped as is known in the prior art and also may be derivatized with other moieties that do not adversely affect the functionality for its intended purpose. Also wherein said grafted polymer has a molecular weight range from 500 to 200,000 Daltons, preferably from 1,000 to 50,000 Daltons. Preferred grafted polymers include cationic grafted polymers, cationic polymers, amphiphilic grafted polymers, amphiphilic molecules and any polymers disclosed by Pike, D. B., et al, Adv. Drug Delivery Rev. 62, 167-183, (2010) including peptides, York, A. W., et al, Biomacromolecules 11 (2): 505 (2010) for N-(2-hydroxypropyl) methacrylamide-s-N-(3-aminopropyl) methacrylamide (HPMA-s-APMA) copolymer, Wu, Y., et al, J Gene Med. 19: e2969 (2017) for functionalized N-(1, 3-dihydroxy propan-2-yl) methacrylamide (DHPMA) and N-(3-aminopropyl) methacrylamide (APMA), Fan, W., et al, Mol. Pharm. 14, 1405-1417 (2017) and include "responsive polymers" disclosed by Hu, et al, in Macromolecules (2010) 43, 8315-8330.

Aptamers Coupled with Amphiphilic Grafted Polymers.

Amphiphilic grafted polymers are a preferred category of flexible carrier substances that contain amphiphilic molecules. Amphiphilic molecules are defined as moieties suitable for pharmaceutical or diagnostic use that contain at least one hydrophilic (polar) moiety and at least one lipophilic (hydrophobic or nonpolar) moiety (i.e. surfactant). In certain embodiments of this invention, amphiphilic molecules including amphiphilic block polymers or copolymers are prepared for use as the flexible carrier substance or as grafted polymers on the flexible carrier substance.

In one embodiment, the desired aptamer is coupled to one or more available sites on the flexible forms of hydrophilic moieties of an amphiphilic molecule ("anchor substance" or "anchor lipid", i.e. cholesterol). Then, said coupled amphiphilic molecule is incorporated or "anchored" into a suitable nanoparticle including a micelle (or a liposome) containing a suitable active agent. The active agents are thereby noncovalently coupled through the micelle composition of the instant invention.

Most preferred are flexible forms of amphiphilic diblock or triblock copolymers prepared from a variety of monomers to provide at least one hydrophilic and one hydrophobic moiety. Amphiphilic cyclodextrin dimers, trimers and polymers as well as amphiphilic block copolymers containing CD dimers, trimers and polymers are included. Preferred amphiphilic grafted polymers include any micelle-forming polymers or copolymers including PEG, PEG derivatives, PLGA, PLGA derivatives and poly (D,L-lactide)-block-methoxypolyethylene glycol (diblock), PEO, PEO derivatives or copolymers, PPO and PPO derivatives. Also preferred are any micelle-forming triblock copolymers (poloxamers) that contain PEG, PEO or PPO, such as PEO-block-PPO-block-PEO in various ratios. Specific examples are poloxamer compounds (i.e. TranzFect of CytRx Corp., USA); the F, L or P series of any Pluronic™ including F-68, F-108, F-127, L-61, L-121, P-85, and any suitable derivatives.

Aptamers Coupled with Cationic Grafted Polymers.

Cationic grafted polymers are a preferred category of carrier substances defined as moieties suitable for pharmaceutical or diagnostic use that contain a net positive charge. In certain embodiments of this invention, flexible forms of cationic grafted polymers including cationic block polymers or copolymers are prepared for use as the flexible carrier substance or as grafted polymers on the flexible carrier substance. Preferred cationic grafted polymers include, but are not limited to, hexadimethrine bromide (polybrene), polyethylenimine (PEI), polyamidoamines (PAMAM), poly-L-lysine (PLL), poly-L-histidines (PLH), poly ornithines and poly arginines, among others.

Aptamers Coupled with Surfactant Substances.

Preferred surfactant substances include suitable flexible carrier forms of fatty acid derivatives, cholesterol derivatives including cholesterol hemisuccinate morpholine salts (CHEMS), gangliosides, phospholipids, pegylated phospholipids, dioleoylphosphatidyl choline (DOPC), dioleoylphosphatidyl ethanolamine (DOPE), any cationic lipids including 1, 2-dioleoyl-3-trmethyl ammonium propane (DOTAP), 1, 2-dioleyloxypropyl-3-trmethyl ammonium chloride (DOTMA), 1, 2-dimyristyloxypropyl-3-dimethyl-hydroxy-ethyl ammonium bromide (DMRIE) 1,2-Dioleoyl-3-phos-phatidylethanolamine (DOPE), 3 beta-[N—[(N',N'-dimeth-ylamino) ethane] carbamoyl]cholesterol (DCchol) and other suitable surfactants.

Aptamers Coupled with Liposome Particles.

A liposome or vesicle is defined for this invention as a water soluble or colloidal structure known in the art as composed of amphiphilic molecules assembled into a bilayer membrane with a generally hydrophobic interior and hydrophilic exterior, that has formed into a generally spherical or rod-like object.

Under suitable conditions, carrier substances that can be used with the aptamers of this invention include liposomes as defined herein, including flexible forms of proteolipo-somes, immuno-liposomes and pegylated (i.e. Stealth) lipo-somes that contain the amphiphilic molecules as well as the protein, carbohydrate and polymer flexible carrier particles defined herein. Said liposomes can have the desired active agents, intercalators, TMs, grafted polymers and other moi-eties coupled to the liposome through suitable covalent coupling to components (i.e. amphiphilic molecule) of said liposome that can include cleavable linkages defined herein. For instance, an aptamer, or other moiety is covalently coupled to a suitable anchor lipid substance (i.e. choles-terol), and/or to a flexible amphiphilic molecule or deriva-tive, that is inserted into the liposome membrane containing an active agent, during or after liposome synthesis.

Liposomes are prepared from suitable amphiphilic mol-ecules and the proteins, carbohydrates and grafted polymers of this invention using well known methods. For instance, suitable methods are disclosed by Kamps, J A, et al, Biochim Biophys Acta. (1996) 1278 (2): 183-90; Willis, M C, et al, Bioconj. Chem. 9, 573-582 (1998) and Wheeler, J J, et al, in Gene Therapy 6, 271-281 (1999).

For instance, aptamers of this invention are suitably coupled to the flexible forms of HSA of Kamps, et al, which is covalently coupled to conventional liposomes, consisting of phosphatidylcholine, cholesterol and maleimido-4-(p-phenylbutyryl) phosphatidylethanolamine, using the hetero-bifunctional reagent N-succinimidyl-S-acetylthioacetate (SATA). Also, a PEG derivative of phosphatidyletha-nolamine (PEG-PE) can be included in the liposomes. Another method employs detergent dialysis wherein the aptamer-lipid, TM-lipid conjugate of the present invention and an active agent is suitably incorporated into any suitable mixture of amphiphilic molecules and suitable detergent. The detergent is then removed by dialysis to produce lipid vesicles containing the coupled active agent. In either case, the amphiphilic molecules can be suitably polymerized or cross linked, including the use of cleavable linkages.

Aptamers Coupled with Carrier Micelles and Carrier Nan-oparticles.

Nanoparticles are known in the art to include a very broad range of organic, and/or inorganic, and/or suitable combi-nations, of particulate materials that can be spherical, rod-like or plate-like. For this invention, nanoparticles are arbi-trarily distinguished from liposomes and micelles. Preferred nanoparticles include any substances used in the art of drug delivery, such as those made from metals including silver (AgNP), gold (AuNP), silicon, carbon, minerals and include nanospheres, nanorods, nanotubes, microdots, dendrimers, polymeric nanoparticles, protein nanoparticles and macro-molecules, as defined herein.

Preferred nanoparticles, liposomes and micelles include, but are not limited to, those described and referenced by; Bar-Zeev, M., et al, Drug Resist. Updates 31, 15-30 (2017); Xin, Y., et al, Cancer Biol. Med. 14, 228-241 (2017); Cheng, R., et al, Biomaterials 34, 3647 e3657 (2013), Roemeling, C. von, et al, Trends in Biotechnol. 35, 159 (2017), Livney, Y. D. et al, Advanced Drug Delivery Rev. 65, 1716-1730 (2013), which are incorporated herein, including references therein.

A preferred flexible carrier micelle for this invention is defined as a water soluble or colloidal structure or aggregate (i.e. nanosphere or dendrimer) known in the art, composed of one or more amphiphilic molecules and may include grafted polymers defined herein. Preferred micelles gener-ally have a single, central and primarily hydrophobic zone or "core" surrounded by a hydrophilic layer or "shell". Pre-ferred micelles and nanoparticles may also be prepared by aggregation and/or condensation by self-attraction of oppo-site charge as between nucleic acid and a cationic substance.

Also preferred are carrier nanoparticles composed of flexible forms of macromolecules including "cascade poly-mers" such as dendrimers. Preferred dendrimers include polyamidoamines as disclosed by J. Haensler, et al, in Bioconj. Chem. 4, 372-379 (1993) and references therein.

Preferred micelles and nanoparticles for this invention range in size from 5 to about 2000 nanometers, preferably from 5 to 400 nm. Micelles are distinguished from lipo-somes which are composed of bilayers. The micelles of this invention can be composed of either a single flexible form of monomolecular, amphiphilic polymer or an aggregate mixture containing many amphiphilic (i.e. surfactant) mol-ecules formed at or above the critical micelle concentration (CMC), in a polar (i.e. aqueous) solution.

Under suitable conditions, substances that can be used with the aptamers of this invention include the micelles, nanoparticles and dendrimers defined herein, including their pegylated forms and those that contain the flexible forms of amphiphilic molecules defined herein, as well as the lipids, proteins, carbohydrates and grafted polymers defined herein. Also included are micelles and nanoparticles containing flexible forms of poly(ethylene glycol) (PEG), or poly (ethylene oxide) (PEO), or poly(propylene oxide) (PPO) such as those disclosed by S-F. Chang, et al, in Human Gene Therapy 15, 481-493 (2004) and Hu, et al, Molec. Pharma-ceutics 7, 914-920 (2010), and references therein. Preferred micelles include the cleavable micelles including prepara-tion methods disclosed in U.S. Pat. No. 6,835,718 B2 and references. therein, which are hereby incorporated into this invention. Said micelles and nanoparticles have the desired active agents, intercalators, targeting molecules, grafted polymers and other moieties coupled to them through suit-able covalent coupling that can include cleavable linkages defined herein.

For instance, any suitable flexible carrier with active agent, or targeting moiety, defined herein, is covalently coupled to a suitable anchor lipid substance (i.e. choles-terol), and/or to a flexible form of an amphiphilic molecule or derivative, which is inserted into said micelle or lipo-some, which may contain an active agent, during or after synthesis.

Micelles are prepared from block copolymers using well known methods. For instance, a suitable method is disclosed by P. L. Soo, et al, in Langmuir 18, 9996-10004 (2002) for polycaprolactone-block-poly(ethylene oxide). A suitable mixture of active agent-coupled lipid, active agent and the desired block copolymer are prepared in a suitable solvent such as DMF. Micellation is achieved by slowly adding water, with constant stirring, until the desired water content is about 80-99%. The product is purified by dialysis against water. The forgoing reference and references therein are hereby incorporated into this invention.

Cleavable Ligand Linkage™ or Ligand Protected Linkage™ Compositions.

A cleavable ligand linkage composition (CLL Composition or interchangeably called a Ligand Protected Linkage™ (LPL)), is a new embodiment of this invention, that is a flexible carrier composition containing at least one active agent and at least two CLL Composition Parts that are bound together to form said CLL carrier composition in a closed conformation, defined herein. Said Parts of said carrier are a cleavable ligand linkage part (CLL Part), and a noncovalent, ligand binding domain part (LBD Part).

In this invention, all said definitions, examples and disclosures for cleavable ligand linkage compositions, including Cleavable Ligand Linkage (CLL Part) and Ligand Binding Domain (LBD Part), all Duplex CLL Carrier Compositions and all Folded CLL Carrier Compositions are hereby included with all disclosures, examples and all references therein from previously filed Provisional App. 62/786,340.

Cleavable Ligand Linkage™ or Ligand Protected Linkage™ Composition Examples.

In all the examples and diagrams herein of said CLL (or LPL), Composition, said CLL Part (or CL) can include an ester linkage, acid labile linkage, cleavable peptide linkages including suitable branched linkages disclosed herein, disulfide linkage, protected disulfide linkage and/or azo linkage, and can include self immolative moieties such as diazeniumdiolates and PABC, as defined or referenced herein (i.e. Anami, Y. et al., Org. Biomol. Chem. 15, 5635-5642 (2017) for enzymatic methods using branched linkers). Said ligand moiety of said CLL Part can include any suitable substance or compound including a suitable active agent, amino acids, nucleic acids, lipids, steroids, 2,4-Dinitrophenols, biotins, carbohydrates, any suitable aliphatic compounds and aromatic compounds that can function as a hapten or a ligand.

In a preferred embodiment, said CLL Part is a cleavable peptide linkage that has a suitable amino acid moiety that also functions as a ligand or hapten such as citrulline or a citrulline derivative.

Wherein said $(TM-A)_N$ and $(TM-B)_N$ represent any suitable targeting moieties, defined herein. And preferably said $(TM-A)_N$ and/or $(TM-B)_N$ can be one or more suitable antibodies (i.e. PAb240), defined herein, specific for mutated protein including mutated p53.

Wherein said open plus ✠ symbol represents noncovalent binding between said {Ab1} and said Cit moiety (amino acid residue).

And wherein said {Ab1} is an antibody, defined herein, that functions as a LBD, defined herein, and specifically binds noncovalently to the citrulline moiety, Cit, of said cleavable linkage.

Wherein said "Carrier" represents any suitable flexible carrier substance of this invention, including from the group of ODs, ODNs, nucleic acids, aptamers, proteins, antibodies, antibody fragments, engineered antibodies, antibody-like scaffolds, nanoparticles, nanostructures, polymers, defined herein and includes suitable modification of said CLL Composition to provide a medical Device Coating Composition, Defined Herein.

Wherein said Citrulline amino acid residue, "Cit" also functions alone or, suitably in combination with adjacent residues, as a ligand or hapten that can be suitably bound to a Ligand Binding Domain (Ab1), that provides protection from cleavage when so bound in a "closed" configuration, defined herein.

Wherein said "Drug" represents any suitable active agent, defined herein, and said "PABC" represents a suitable self-immolative coupling group such as a p-aminobenzyloxycarbonyl group.

Wherein said $\{X\}_N$ or $\{Z\}_N$ represent any suitably coupled moieties including amino acid residues, nucleic acids, spacers and polymers, and also wherein subscript "N" is an optional number from 1 to 10 to indicate the suitable number of said moieties, or if 0 indicating no moiety.

And wherein said $\{Z\}_N$ can optionally include a suitable branched intermediate substance, defined herein, that provides suitable covalent coupling of multiple said "Drug" moieties.

And wherein said brackets, { } around certain moieties represent suitable substances or compositions and/or synthesis methods needed to provide the intended function of said moiety.

In another preferred embodiment, said peptide linkage "Val-Cit-Gly" is substituted with any suitable linkage from the group of cleavable linkages, preferably any suitable linkage or amino acid sequence, (i.e. G-F-L-G, (Seq ID No:24) or disulfide, etc.), defined herein.

In any embodiment of this invention, said specific binding peptide sequence is suitably synthesized using well known methods including phage display screening, including methods disclosed and referenced by Krishnamurthy, A., et al, Pharmacol. Therapeutics 185, 122-134 (2018); Krah, S., et al, New Biotechnology 39, 167-173 (2017) and Leung, I., et al, J Mol Biol 429, 115-127 (2017), among others.

Examples of peptide sequences and ligand moieties that would be useful in this invention with suitable modification (i.e. antibody and/or via immunoaffinity methods) are well known in the art, such as in "tags" used for protein purification. For instance, the disclosures and references given by Wood, D W, Current Opinion Structural Biol. 26:54-61 (2014), Young, C L, et al, Biotechnol. J. 7, 620-634 (2012), and Fritze, C E, et al, Meth. in Enzymology 327, 3-16 (2000), provide peptide/epitope structures including "FLAG", c-Myc, GM-CSF and Twin Strep II. Other useful ligands and/or sequences with Binding Domains are folded protein domains with highly specific affinities for small molecule ligands that include "Folded Domain Tags" that include MBP, GST, Starch, Fluoroapetite, Diatomite and Beta-GRP.

Specific examples useful with suitable modification for this invention, include: peptide EQKLISEEDL (Seq ID No:64) which is highly specific for the anti-c-Myc antibody 9E10, and wherein a suitable Ab fragment of 9E10 can be used; similarly, the FLAG octapeptide DYKDDDDK (Seq ID No:65) can be used with the complementary antibody M1, or a suitable Ab M1 fragment; also the 1D4 epitope sequence TETSQVAPA (Seq ID No:66) (from bovine rhodopsin), used with complementary, high affinity rho-1D4 monoclonal antibody (flintbox.com). In each example, one or more active agents would be suitably covalently coupled using suitable peptide sequences.

One preferred embodiment, several useful moieties for this invention are suitably located in the same synthetic structure, or strand, defined herein. And wherein said strand includes suitable functional groups, spacers, linkages, active agents, targeting moieties and a hinge-like region to allow folding upon itself, forming a "hairpin-like" "closed conformation" composition. For instance, said synthetic structure can include a continuous nucleic acid or amino acid sequence, or strand, an aptamer, defined herein, and/or is part of a recombinant antibody structure, as defined herein.

In certain examples provided, said moiety can be a bispecific or multispecific aptamer (Apt) or antibody, defined herein, wherein at least one binding domain (i.e. nucleic acid sequence or amino acid sequence) of said aptamer, is specific for all or part of said target substance, defined herein.

Antibodies useful in this invention, with suitable modification as needed, can be bispecific antibodies, chimeric antibodies, scFv dimers (i.e. diabodies), minibodies, triabodies, tetrabodies, single domain antibodies, antibody fragments and antibody-like scaffolds, among others disclosed in references herein.

Targeting Moieties, TM or $(TM)_R$ in Compositions of this Invention.

In all compositions of this invention, at least one targeting moiety (TM, plural TMs), defined herein, is preferably specific for any suitable target substance, defined herein.

In all the examples provided herein, TM or $(TM)_R$ is a moiety selected from the group of targeting moieties as described herein and is suitably incorporated into, or is covalently coupled to said flexible carrier substance through a covalent linkage, as defined herein. Said TM is preferably part of the same synthetic structure, such as a continuous nucleic acid or amino acid sequence, or strand in a flexible carrier aptamer, defined herein. Or is part of a recombinant antibody structure, as defined herein. Said TM is located and/or coupled at any suitable position, including at or near the end of said flexible carrier substance.

Carrier Aptamers and Other Flexible Carrier Composition Examples.

Descriptions for all Symbols and Letters Used in all Example Diagrams Herein, when Applicable.

It is understood by those skilled in the art of nucleic acids and amino acids that all example diagrams disclosed herein are representative, wherein the specific positioning of certain moieties and certain sequences, are meant to be suitable and/or optional for the intended purpose of said compositions and can be suitably modified to perform the intended purpose.

Where applicable, Apt-A, Apt-B, Apt-C, Apt-D, etc., represent any suitable aptamers, defined herein. Said aptamers have at least one moiety that suitably functions as, or is coupled to, said TM, defined herein. Said aptamers can be suitably derivatized to provide a functional group (i.e. sulfhydryl, amino or carboxyl), for covalently coupling through a suitable linkage to said targeting moiety or other suitable moieties.

Where applicable, CLL represents any suitable covalent, Cleavable Ligand Linkage™, defined herein and CL represents a covalent, Cleavable Linkage, defined herein, and LBD represents any suitable Ligand Binding Domain, defined herein.

Heavy (Filled) Block or Filled Dash or Filled Arrow Symbols; ▮ or ▬ or ⌙ represent suitable covalent coupling between adjacent moieties and can also include one or more spacer units (i.e. carbon atoms, alkanes); $(CH_2)_R$ when suitable.

Said $(CH_2)_R$ represents said spacer units wherein R is an integer for the number of said units that can be 0 (meaning no spacer), or an integer between 1 and 30, preferably between 1 and 10. Said $(CH_2)_R$ can also be any suitable spacer moiety, including nucleic acids, amino acids, ligands, functional groups, hydroxyls, amino groups or carbonyl groups, or combinations of these.;

Open Dash ▭; open Plus ⊕; or open Arrows

⤷ symbols represent noncovalent coupling, defined herein, between any suitable moieties including a Cleavable Ligand Linkage (CLL), and any oligonucleotide "sticky ends". Said noncovalent coupling can include suitable intercalation with suitable nucleic acid strands.

Brackets { } represent any suitable substance or moiety needed to provide the intended structure and/or properties represented, as defined herein.

Optionally, said compositions can have structurally incorporated within, or covalently coupled at any suitable position on them, one or more additional targeting moieties $(TM)_R$ wherein R is an integer for the number of said moieties that can be between 1 and 30, preferably between 1 and 5.

In all the examples provided herein, all iterations of said TM, including TM-A, TM-B, TM-C, $(TM)_R$, $(TM-A)_R$, $(TM-B)_R$, $(TM-C)_R$, etc., is a targeting moiety or an optional substance, including intracellular targeting and/or facilitates intracellular trafficking, as defined herein.

Said composition, defined herein, preferably contains nucleic acids and/or amino acids (i.e. aptamer), a protein, peptide motif, antibody fragment or antibody scaffold, with suitable noncovalent binding affinity for the corresponding (complementary) sequence, defined herein.

And wherein said composition provides said CL-Drug with protection from cleavage when said composition is in a closed conformation.

"Drug-A" or "Drug-B", or "CL-Drug", etc., are any suitable active agents that are covalently coupled through a cleavable linkage, CL, as defined herein, to their respective flexible carrier substance (i.e. aptamer), as defined herein.

Branched Linkage as an Intermediate Substance.

A branched linkage moiety (modified from Anami, Y. et al., Org. Biomol. Chem. 15, 5635-5642 (2017)), is shown that provides coupling between a suitable flexible carrier substance, and active agents or drugs.

Branched Linkage

Said branched linkage have suitably coupled two or more, (i.e. multiple) therapeutic active agents, and can be suitably substituted in place of any coupled active agent or "drug" disclosed herein, including in any examples herein.

For synthesis, said branched linkage with available azide groups are suitably coupled to suitable additional moieties or cleavable linkages that contain available alkyne functional groups (i.e. copper-catalyzed), resulting in suitable di-substituted triazoles. Alternatively, said azides can be suitably reduced to provide primary amines, or derivatized to thiols, for subsequent coupling to the desired moieties. Alternatively, other branching strategies and/or moieties can be substituted, such as suitable poly-L-lysines or polyethylenimines, or suitable dendrimers disclosed herein.

Said aptamers A and B each have at least one moiety that functions as a targeting moiety, defined herein, and another moiety that functions as an LBD and can include suitable spacers, defined herein.

Said CL moieties, defined herein, may be identical or can be of different structure, or contain different amino acids.

Any suitable polymers, nucleic acids and/or amino acid residues can be derivatized, substituted, added or subtracted in these compositions to provide the desired functional groups, or other moieties at any suitable position on said respective aptamer, and can include suitable spacer groups (i.e. nucleic and/or amino acids).

The Symbol; "DRUG" represents any suitable active agent within the composition comprising said CL, defined herein, covalently coupled to a suitable nucleic acid or phosphoramidite, defined herein, in a suitable "stem" or "loop" or "bulge" section as desired.

Brackets { } represent any suitable substances or sequences to provide the represented moiety and/or properties needed.

The Loop symbol; LOOP is a suitable nonbinding NA or peptide strand that can contain suitable nucleic acids or amino acids (i.e. proline), to provide said structural loop or bulge without specific binding. Said Loop region can also include any suitable secondary structure such as more than one hybridized stem region, additional loops and/or partial hybridizations and/or sections of noncomplimentarity of the nucleic acid strand that can produce "bulges" or "hairpin bulges" in said stem regions.

Alternatively, said nonbinding Loop also contains any suitable functional group and/or phosphoramidite suitably derivatized to provide a functional group (i.e. sulfhydryl, amino or carboxyl), at a suitable location for covalently coupling to an active agent through a suitable cleavable linkage, defined herein.

Conversion to a Nanoparticle Flexible Carrier Composition.

With suitable modifications as needed, the examples provided can also function as Nanoparticle Flexible Carrier Compositions, defined herein. All said definitions for nanoparticle compositions hereby include disclosures and all references from previously filed App. 62/786,340.

For instance, any representative Flexible Carrier Aptamer is suitably modified and coupled using a covalent linkage to any suitable nanoparticle, micelle or liposome, defined herein.

The resulting substance or component coupled to said nanoparticle can then function as said NanoParticle Composition (NP Composition), defined herein.

Optionally, the substance (i.e. Apt-A and/or B), with a covalently coupled active agent can be suitably modified or derivatized as needed, wherein any suitable block polymers, lipids or amino acid residues can be derivatized, substituted, added or subtracted in this composition to provide the desired structure, properties, functional groups and/or binding affinities needed for said NP Composition.

Also in the examples, with suitable modification, said nanoparticle can be any suitable carrier substance such as an AuNP, micelle, liposome, stealth liposome, nanosphere, microdot, nanorod, dendrimer, polymeric nanoparticle or protein nanoparticle or macromolecule, as defined herein.

Nanoparticle Flexible Carrier Composition Examples.

In examples provided, said Nanoparticle Flexible Carrier Compositions are comprised of two components, an Active Agent Component (AA Component) and a NanoParticle Component (NP Component). Either component can be suitably modified or derivatized as needed, wherein any suitable block polymers, lipids, nucleic acids or amino acid residues can be derivatized, substituted, added or subtracted in this composition to provide the desired structure, properties, functional groups and/or binding affinities between said components.

Also in the examples, with suitable modification, said nanoparticle can be any suitable carrier substance such as a micelle, liposome, stealth liposome, nanosphere, nanorod, nanotube, microdot, AuNP, dendrimer, polymeric nanoparticle or protein nanoparticle or macromolecule, as defined herein.

Said NP Component comprises any suitable carrier substance (i.e. amphiphilic) that provides or forms the nanoparticle or micelle, as defined herein. Said NP Component can include a surfactant, amphiphilic grafted polymer, amphiphilic peptide or protein, amphiphilic grafted polymer and/or amphiphilic block polymer, as defined herein.

Said NP Component also includes a suitable noncovalent coupling site or NP Binding Domain (i.e. NP Lipid), defined herein, for coupling and/or anchoring any suitable Anchoring Substance (i.e. Anchor Lipid) on said AA component.

The AA Component comprises any suitable targeting moiety, defined herein, covalently coupled to any suitable Anchor Substance (i.e. Anchor Lipid). Said AA Component also has at least one active agent, defined herein, represented as "Drug", covalently coupled at any suitable position on it.

Said covalent coupling between said AA component and said active agent is through a cleavable linkage, CL, as defined herein. In the examples, said CL is preferably a self immolative linkage, defined herein and can include a suitable spacer group $(CH_2)_R$, defined herein.

Example Diagram VI-A. Nanoparticle and Aptamer Carrier Composition

Aptamer A (Apt-A), is suitably coupled to said nanoparticle and includes Targeting Moiety A $(TM-A)_R$. Active Agent (Drug-A) is covalently coupled to said aptamer through a CL linkage.

Said nanoparticle includes other optional moieties such as $\{PEG\}-(TM)_R$ and $\{Apt-B\}-(TM-B)_R$ that are suitably coupled to said nanoparticle.

Heavy (Filled) Dash Symbols; ▬ or ▮ represent suitable covalent coupling between adjacent moieties.

Open Plus Symbol; ⊹ represents suitable noncovalent coupling between moieties.

Double Bar Symbol; ▦ represents any suitable coupling substance and/or coupling method that provides either covalent or noncovalent coupling of the indicated moiety to the particular nanoparticle, micelle or liposome used in the example.

Brackets { } represent any suitable substances to provide the represented moiety and/or properties needed.

In said Nanoparticle Composition Example, the nanoparticle carrier composition is comprised of several parts and moieties. They are:

A Nanoparticle Part (NP).

A CL coupled Active Agent that can be suitably substituted with said branched linkage, defined herein, with suitably coupled, multiple therapeutic active agents.

An Apt-A containing CL coupled Active Agent and $(TM-A)_R$ that is preferably specific for binding any suitable intracellular target substance, cell surface receptor, or disease organism, defined herein.

An optional Apt-B containing Aptamer B with $(TM-B)_R$ that is preferably specific for binding a cell surface receptor, or is a transduction vector, defined herein, that facilitates internalization and/or intracellular trafficking of said Nanoparticle Composition.

A PEG moiety containing any suitable polymer such as polyethylene glycol, hyaluronic acid, etc.

Said NanoParticle (NP) represents any suitable carrier substance useful with suitable modification for this invention, that includes nanoparticles, nanocarriers, RNA, DNA, Holliday junctions, DNA G-quadruplexes, DNA origami structures such as disclosed by Douglas, S M, et al, Nucleic Acids Res. 37, 5001-5006 (2009) and Han, D., et al., Science 358, eaao2648 DOI: 10.1126 (2017); cruciform DNA, albumins, nanospheres, nanotubes, microdots, nano-dots, dendrimers, micelles, liposomes and any suitable Biomaterials for Drug Delivery (Fenton, O S, et al, Adv. Mater. 1705328, 1-29 (2018)) including references therein. Also preferred and useful with suitable modification for this invention, are any self-assembly materials and objects, including:

Responsive DNA G-quadruplex micelles (Cozzoli, L, et al, Chem. Commun., 54, 260 (2018)), RNA-based or DNA-based oligonucleotide structures such as semirigid Holliday junctions (Li, Z., et al, Angew. Chem. Int. Ed. 54, 11706-11710 (2015)), Aptamer-Based Riboswitches (Lee, CH, Nucleic Acid Therap. 26, 44-50 (2016)), stimuli-responsive polymers (Taghizadeh, B, et al, Drug Del. 22:2, 145-155 (2015)), cruciform DNA constructs; 4-arm Holliday junction DNA nanoconstructs (Tung, J, et al, Nature: Scientific Reports 7:793 (2017)) and Aptamer-Based Three-Way Junction Pocket DNA Nanostructures (Taghdisi, S M, et al, Mol. Pharmaceutics 15, 1972-1978 (2018)), including references therein.

Said NP can be composed of any suitable material, any suitable size and any suitable shape known or referenced in the art of in vivo drug delivery. Said NP can include any suitable polymer, surfactant, grafted polymer, peptide or protein, amphiphilic grafted polymer and/or amphiphilic block polymer, any suitable lipid, surfactant, lipophilic grafted polymer, lipophilic peptide or protein and/or lipophilic block polymer, any metals, or combinations of these, as defined or referenced herein. Said NP can have covalently coupled at any suitable position on it, one or more of the moieties included in said composition, including said Apt-A, Apt-B and PEG, defined herein, in any suitable combination. Said NP can have covalently coupled at any suitable position on it, one or more targeting moieties (TM) R and/or PEG moieties, defined herein.

Said aptamer containing an Active Agent has at least one active agent, defined herein, represented as "Drug", covalently coupled at any suitable position on it. Said active agent is covalently coupled to said aptamer through said CL (cleavable linkage), as defined herein.

When applicable, CL is any suitable covalent linkage, defined herein and wherein said covalently coupled NP Lipid and PEG can include a suitable spacer group $(CH_2)_R$, defined herein.

In all the Examples, Aptamer represents any suitable flexible carrier aptamer that includes a specific targeting moiety, and can function as a flexible carrier substance, as defined herein. Said aptamer is preferably specific for any suitable target substance such as disease biomarkers and cell receptors, as defined herein. Said aptamer can include recombinant structures and can have covalently coupled at any suitable position on it, one or more additional targeting moieties $(TM)_R$ wherein R is an integer 0 (meaning no TM), or an integer between 1 and 30, preferably between 1 and 5.

In all the Examples in this invention, said {PEG} symbol represents as an option, any suitable polymer that preferably provides low- or non-immunogenic properties such as so-called "stealth" liposomes, when exposed to an in vivo environment. Also included are suitable grafted polymers, (i.e. HPMA), responsive polymers, amphiphilic grafted polymers and/or block polymers, defined herein. Said {PEG} can have covalently coupled at any suitable position on it, one or more targeting moieties $(TM)_R$ wherein R is an integer 0 (meaning no TM), or an integer between 1 and 30, preferably between 1 and 5. When applicable, said $(TM)_R$ is preferably specific for binding a cell surface receptor, or is a transduction vector, defined herein, that facilitates internalization of said Nanoparticle CLL Composition. Alternatively, said $(TM)_R$ is preferably specific for binding an intracellular target substance, (i.e. NLS) and/or facilitates intracellular trafficking, defined herein.

In all examples shown, said $\{(CH_2)_R\}$ represents said spacer units wherein R is an integer 0 (meaning no spacer), or an integer between 1 and 30, preferably between 2 and 10. Said $\{(CH_2)_R\}$ can include any suitable spacer moiety, that includes carbon atoms, nucleic acids, amino acids, and any suitable substances defined as {PEG}, herein. Said $\{(CH_2)_R\}$ can also include suitable functional groups, including hydroxyls, amino groups, sulfhydryls or carbonyl groups, or combinations of these.

In a preferred embodiment of this invention, said NP is a gold NP (AuNP), and is based on suitable modification of the disclosures and references made by Ma, Y., et al, Angew. Chem. Int. Ed., 55, 3304-3308 (2016), and supporting information, for DNA hairpins and/or molecular beacons coupled to AuNPs that target telomerase in cancer cells. For example, any suitable aptamers of this invention are suitably thiolated, such as at their 3' ends, to provide coupling to suitable AuNps.

Also useful in this invention, for anti-microbial NPs, disclosures and references by Baptista, P V, et al, Front. Microbiol. 9:1441 (2018), employ metallic NPs including silver NPs (AgNP), and include delivery of various antibiotics and Antimicrobial Peptides (AMPs). Also useful in this invention, for functionalizing any suitable NP materials and any suitable medical device materials or implants, for subsequent coupling to the compositions of this invention, with suitable modification, are the methods disclosed by Francolini, I., et al, APMIS 125:392-417 (2017), and Liu, C-Y, et al, Langmuir 32, 5019-5028 (2016), that include using polydopamine (pDA), and various other methods. All of the references disclosed herein are hereby incorporated and include additional references and supporting information therein.

Conversion of Nanoparticle Compositions to a Device Coating Composition.

With suitable modifications as needed, any Nanoparticle Composition examples, including covalent or noncovalent coupling compositions provided herein, can also be used to prepare Device Coating Compositions, that can be applied to any suitable medical device including any medical implants, drug eluting implants, intubations, shunts, stents including drug eluting stents, catheters, including balloon catheters and any resorbable stents, catheters or other resorbable implants and devices. Said Device Coating Composition will provide a drug releasing coating that is useful for controlled drug release from said devices and implants. All said definitions and examples for device coating compositions hereby include all disclosures, examples and all references from previously filed Provisional App. 62/786,340.

Derivatized Nucleic Acid Aptamers.

When nucleic acids are used as carrier nucleic acids and/or as aptamers in this invention, preferred aptamers and nucleic acids include suitably derivatized molecular beacons and nucleic acids defined herein, and include any pharmaceutical nucleic acids, defined herein to mean useful or potentially useful in therapeutic or prophylactic applications in humans, or any other vertebrate animals and in plants. The most preferred nucleic acid aptamers defined as pharmaceutical are nucleic acids against (i.e. target), vermin, insects, parasites, viral diseases, bacterial diseases, fungal diseases, and other microbial diseases. Most preferred nucleic acids are useful against cancers, heart diseases, autoimmune diseases, genetic and other diseases or disorders in humans and other vertebrates. Also included are nucleic acids useful against vermin, insects, parasites, viral diseases, bacterial diseases, fungal diseases, and other microbial diseases in plants. They also include specific DNA sequences used for gene therapy.

For this invention, all examples and references to specific "preferred aptamers" are meant to include the nucleic acid sequences or amino acid sequences that provide the specific binding properties and/or allosteric properties of said aptamer and may or may not include other sequences disclosed in said examples when suitably incorporated and/or modified for use in this invention.

Preferred examples of derivatized nucleic acids useful as aptamers include any suitably derivatized nucleic acids disclosed and/or categorized herein, including, but are not limited to; any antisense nucleic acids that include phosphodiester antisense oligonucleotides (ON) and antisense oligodeoxynucleotides (ODN); any "backbone derivatized" oligonucleotides or oligodeoxynucleotides (sense and/or antisense), where the sugar-phosphate "backbone" has been derivatized or replaced with "backbone analogues"; any "mixed backbone derivatized" oligonucleotides or oligodeoxynucleotides (sense and/or antisense); any capped nucleic others, with suitable modification. References listed herein, and references therein, are incorporated herein by reference.

Preferred aptamers include, but are not limited to, those disclosed in the following references, including aptamer sequences referenced therein, with suitable modification: Abeydeera, N D, et al, Nucleic Acids Res. 44, 8052-8064 (2016) (RNA), Alevtina A. Goulko, A A, et al, Trends Anal. Chem. 28, 878 (2009) (Beacons), and M. Citartan et al. Biosensors Bioelectronics 34, 1-11 (2012), Liew, F F., et al. Bioorg. Med. Chem. 19, 5771-5775 (2011). Liew, et al disclose combinations of RNA and peptide, such as RNP (ribonucleopeptide), that are useful for this invention with suitable modification.-
Useful Nucleic Acid Aptamers for this Invention.

Preferred aptamers for this invention include, but are not limited to, those disclosed in all applicable references, including all aptamer sequences referenced therein: Bates, P J, et al, Exp Mol Pathol. 86 (3): 151-164 (2009); disclose nucleolin binding, G rich aptamers useful for this invention. It includes aptamer AS1411 (formerly AGRO100) wherein the 5'-terminus "tail" (5'-TTT) of GRO29A may be suitably coupled to other moieties or truncated to provide the truncated 26-mer aptamer sequence, 5'-GGTGGTGGT-GGTTGTGGTGGTGGTGG (Seq ID No:69), also known as AGRO100 (Aptamera company) and as AS1411 (Antisoma company, 2005).

Cerchia, L., et al, Trends in Biotech. 28, 517-525, (2010); disclose aptamer sequence development methods SELEX, Cell-SELEX and Differential Cell-SELEX, useful for this invention with suitable modification. Cha, T-G, et al, ACS Nano 5, 4236-4244, (2011); disclose an insulin-binding aptamer useful for this invention; IBA: 5'-GGT GGT GGG GGG GGT TGG TAG GGT GTC TTC-3' (Seg ID No: 70).

Dausse, E., et al, Curr. Opin. Pharma., 9, 602-607, (2009); disclose a Table of Useful Aptamers that are useful in this invention with suitable modification. The listings are in order of aptamer name (company), target, oligo type and application.

| Useful Extracellular or Membrane DNA Aptamers and Their Targets. | | | |
|---|---|---|---|
| NU172 (Archemix/Nuvelo) | Thrombin | NX21909 | NE |
| ARC127 or E10030 (Archemix) | PDGF-B | AS1411 (Antisoma/ Archemix) | Nucleolin |
| Useful Extracellular or Membrane RNA Aptamers and Their Targets. | | | |
| ARC1779 (Archemix) | von Willebrand fact. | NOX-E36 (Noxxon) | MCP-1 L-RNA |
| ARC1905 (Archemix) | complement C5 2'F-RNA | 11-1.41 | Angiopoietin 2, 2'-F-RNA |
| RB006 (Regado Biosci.) | Factor IXa 2'F-RNA | A10 | PSMA 2'-F-RNA |
| NOX-B11 (Noxxon.) | Ghrelin L-RNA | D4 | RET 2'-F-RNA |
| Useful Intracellular RNA Aptamers and Their Targets. | | | |
| R06 | TAR element (HIV) | R20 | NS5B protein (HCV) |
| SE RNA | NS3 protein (HCV) | iaRNA | B52 protein (*Drosophila*) |
| G9 | NS3 protein (HCV) | | | acids; any nucleic acid hybrids (i.e. RNA-DNA hybrids); any nucleic acid chimeras (i.e. RNA-DNA chimeras); any synthetic nucleic acid polymers including peptide nucleic acids (PNA); any nucleotide mimics or co-oligomers like phosphoric acid ester nucleic acids (PHONA); any triplex-forming nucleic acids and mutagenic triplex-forming nucleic acids. Also included are any suitable combinations of said derivatized nucleic acids.

Preferred aptamers include any suitable aptamer derivatives or conjugates, including PEG conjugates, that include, but are not limited to, disclosures by OC Farokhzad, et al, Cancer Res. 64, 7668-72 (2004) and S R Watson, et al, Antisense Nucleic Acid Drug Dev. 10, 63-75 (2000), among Also, Famulok, M., J. Med. Chem., 52, 6951-6957, (2009); discloses useful structures and chemical modifications that can be introduced into aptamers including allosteric ribozymes and intracellular aptamers or intramers, with suitable modification for this invention. Famulok, M., et al, Chemical Reviews, 107, 3715-3743, (2007); have reviewed and disclosed and/or referenced useful aptamers as capture ligands, as therapeutic agents, anti-viral aptamers, aptazymes and aptamers that will function in vivo that can be useful for this invention. Also disclosed are methods and references for modifying aptamers by attaching various substances including cholesterol, D-desthiobiotins, biotins, streptavidin, NeutrAvidin, or polyethylene-glycol groups or by anchoring an aptamer to liposomes. Guthrie, J W et al, Methods 38, 324-330 (2006); have reviewed and disclosed and/or referenced useful aptamers for this invention.

Proximity Binding

As is disclosed by Yang, J. et al, Anal. Chem. 89, 5138-5143 (2017) and references therein, are methods and substances that can be suitably modified for this invention. The methods require pairs of specific affinity probes or aptamers, to bind to the same target substance (i.e. protein) and also become sequence-specifically anchored in close proximity. This highly stringent requirement of dual binding and proximate recognition makes this design of targeting highly selective and useful for targeting in this invention.

Juskowiak, B., Anal Bioanal Chem 399, 3157-3176, (2011); have reviewed and disclosed and/or referenced useful methods for conjugating substances to aptamers. The sodium quadruplex formed by the human telomeric DNA sequence, d[AG3(T2AG3)3], has an antiparallel strand orientation with the basket-type structure, whereas the potassium complex has a variety of G-quadruplex structures ranging from antiparallel basket- or chair-type structures to parallel and hybrid conformations. In contrast, the thrombin-binding DNA aptamer (5'-d(GGTTGGTGTGGTTGG)-3') (Seq ID No:71) forms only one G4 structure, a chair-type quadruplex, for this invention. Nimjee, S M, et al, Annu. Rev. Med. 56, 555-83, (2005); have reviewed and disclosed and/or referenced a wide range of useful therapeutic aptamers that can be used in this invention with suitable modification. Nutiu R., et al, Methods 37, 16-25, (2005); have disclosed and/or referenced useful structure switching aptamers that can be used in this invention with suitable modification, such as removal and/or substitution of biotins or fluorescent labels with active agents and with targeting moieties.

Useful aptamers with their names and their sequences are as follows:

```
ATP1.1:
                                     (Seq ID No: 72)
5'-CCTGCCACGCTCCGCACTTCGGAGGAGTTCTGCAGCGATC-

TTGATCGGGGACGGGGGAGAAAGGTTTTAAGCTTGGCACCCGCATCGT-3'

BDNA:
                                     (Seq ID No: 73)
5'-TACCGCAAAAAAAAACAAGAATCGCTGCAG-3'

FDNA1:
                                     (Seq ID No: 74)
5'-GCGGAGCGTGGCAGG-3'

FDNA2:
                                     (Seq ID No: 75)
5'-CTCTCCTCTTACCAGATTCG-3'

GTP1.2:
                                     (Seq ID No: 76)
5'-CGAATCTGGTAAGAGGAGAGGGGTGGTTTCCGCAGCGATTCTT-

GATCGCGGAAGTCGGTGGGGAGGGTTAAGCTTGGCACCCGCATCGT-3'

L1:
                                     (Seq ID No: 77)
5'-CCTGCCACGCTCCGCAAGCTTN₁₀TGCAGCGATTCTTGATCG N₂₀-

TAAGCTTGGCACCCGCATCGT-3'

MAP:
                                     (Seq ID No: 78)
5'-CCTGCCACGCTCCGCTCACTGACCTGGGGGAGTATTGCGGAGGAA

GGT-3'
```

-continued

```
P1:
                                     (Seq ID No: 79)
5'-GCGGAGCGTGGCAGG-3'

P2:
                                     (Seq ID No: 80)
5'-ACGATGCGGGTGCCAAGCTTAr-3'

P:
                                     (Seq ID No: 81)
5'-GCCTCGCACCGTCC-3'

QDNA1:
                                     (Seq ID No: 82)
5'-CCCAGGTCAGTG-3'

QDNA2:
                                     (SEQ ID No: 83)
5'-TACCGCAAAAAAAAACAAGAATCGCTGCAG-3'
```

Ozalp, V C, et al, Pharmaceuticals 4, 1137-1157 (2011). They have disclosed and/or referenced useful structure switching aptamers that can be used in this invention with suitable modification. For instance, the pore-blocking or capping function of said aptamers can be applied to this invention for sterically protecting the cleavable linkages between an active agent and a carrier substance of this invention. Useful aptamers and their sequences are as follows:

Leukemia Cell Lines (Acute Human Lymphomas T-Cells). The protein target for this aptamer is Protein Tyrosine Kinase-like 7 (PTK7). The aptamer name is Sgc8c:

```
                                     (Seq ID No: 84)
ATC TAA CTG CTG CGC CGC CGG GAA AAT ACT GTA CGG

TTA GA

Specific for T-Cells, KH1C12:
                                     (Seq ID No: 85)
ATCCAGAGTGACGCAGCATGCCCTAGTTACTACTACTCTTTTTAGCAAA

C,

Specific for Ramos Cells, TD05:
                                     (Seq ID No: 86)
AAC ACC GGG AGG ATA GTT CGG TGG CTG TTC AGG GTC

TCC TCC CGG TG.

Prostate Specific Membrane Antigen, A10:
                                     (Seq ID No: 87)
GGGAGGACGAUGCGGAUCAGCCAUGUUUACGUCACUCCUUGUCAAUCCU

CAUCGGC

Epidermal Growth Factor Receptor, J10:
                                     (Seq ID No: 90)
GGCGCUCCGACCUUAGUCUC

UGCAAGAUAAACCGUGCUAU UGACCACCCUCAACACACU

UAUUUAAUGUAUUGAACGGACCUACGAACCGUGUAGCACAGCAGA

Transferrin receptor (extracellular domain of
mouse transferrin), FB4:
                                     (Seq ID No: 88)
TGAGGGCGGAAGAACTAATTTGGGACGGATTGCGGCCGTTGTCTGTGG

C,
```

Nucleolin, AS1411: TTGGTGGTGGTGGTTGTGGTGGTGGTGG (Seq ID No:89),

Phillips, J A, et al, Bioconjugate Chem. 22, 282-288 (2011). They have disclosed and/or referenced useful aptamer sequences and conjugation methods that can be used in this invention with suitable modification. For instance, D-threoninol can be used as the linker to a suitable carboxylated compound for coupling to suitable phosphoramidites using synthesis routes similar to published protocols, including disclosures in their Supporting Information. Sequences of useful aptamers include Sgc8c, and conjugated Sgc8c, wherein the azobenzene moieties can suitably be substituted for certain cleavable linkages to suitable active agents in this invention. Sassolas, A., et al, Analyst, 136, 257-274 (2011); disclose, review and reference many aptamers useful for this invention with suitable modification, such as from analytical methods to various drug delivery methods disclosed herein.

Sefah, K., et al, PLOS ONE 5, e14269, pages 1-14 (2010); disclose, review and reference many aptamers for targeting cancer biomarkers useful for this invention with suitable modification, such as from analytical methods to various drug delivery methods disclosed herein. Soontornworajit, B, et al, Biomacromolecules 11, 2724-2730 (2010); disclose nucleic acid aptamers that are useful for this invention with suitable modification. Tok, J, et al, Talanta 81, 732-736 (2010); disclose aptamers useful for this invention with suitable modification, including the following sequence for MRCK M6MAB: 5'/FAM/CCTACTAATGATAAAC-CACTGGTGAATCGCTCAAGTCAGTAGTAGG (Seq ID No:91)

Zhou, J., et al, Methods 54, 284-294 (2011); They disclose and reference aptamers, including chimera aptamers for targeting HIV virus useful for this invention with suitable modification, such as for the various drug delivery methods disclosed herein.

```
A-1 aptamer (81 nt):
                                 (Seq ID No: 92)
5'-GGG AGG ACG AUG CGG AAU UGA GGG ACC ACG CGC UGC

UUG UUG UGA UAA GCA GUU UGU CGU GAU GGC AGA CGA

CUC GCC CGA-3'.

Ba' pRNA-aptamer chimera (pRNA-A-1 D3) (152 nt):
                                 (Seq ID No: 93)
5'-GGU UGA UUG UCC GUC AAU CAU GGC GGG AGG ACG AUG

CGG AAU UGA GGG ACC ACG CGC UGC UUG UUG UGA UAA

GCA GUU UGU CGU GAU GGC AGA CGA CUC GCC CGU CAU

GUG UAU GUU GGG GAU UAA CGC CUG AUU GAG UUC AGC

CCA CAU AC-3'.

Ba' pRNA-aptamer chimera (pRNA-A-1 D4) (198 nt):
                                 (Seq ID No: 94)
5'-GGG AGG ACG AUG CGG AAU UGA GGG ACC ACG CGC UGC

UUG UUG UGA UAA GCA GUU UGU CGU GAU GGC AGA CGA

CUC GCC CGA GGA AUG GUA CGG UAC UUC CAU UGU CAU

GUG UAU GUU GGG GAU UAA CGC CUG AUU GAG UUC AGC

CCA CAU ACU UUG UUG AUU GUC CGU CAA UCA UGG CAA

AAG UGC ACG CUA CUU UCC-3'.
```

Allosteric Response Carrier Ribozymes.

For construction of allosteric ribozymes for this invention, a short RNA motif termed a communication module, connects a ribozyme module and an allosteric ligand-binding module is suitably introduced to effectively transduce the structural change associated with the ligand-binding to a flexible carrier of this invention using a similar mechanism used for said ribozyme module. Tung, C—H, et al, Bioconj. Chem. 11, 605-618 (2000), disclose different preparation methods useful in this invention, for peptide-oligonucleotide conjugates (POC), as well as peptide sequences that are useful for this invention with suitable modification, disclosed in Table 1, and references therein.

Peptide Aptamers and TM.

Preferred peptide aptamers and peptide targeting moieties (TM) are suitably incorporated into any flexible carrier composition disclosed herein, and include, with suitable modification, said biorecognition elements or sequences from any type of peptides and peptide aptamers including, but not limited to, those disclosed or referenced by the following references. In certain examples, the amino acid sequences for peptide aptamers are shown with scaffold protein thioredoxin (TRX). Depending on the desired application for this invention, scaffold sequences may be included, or eliminated, or suitably replaced with other suitable sequences or other suitable substances, disclosed herein. Preferred references include:

Bahr, C, et al, Growth Factors. 2005, 23 (1): 1-14; Borghouts, C, et al, Expert Opin Biol Ther. 2005, 5(6):783-97; Brown, C J, et al, J. Mol. Biol. (2010) 395, 871-883; Bueger, C, et al, J Cancer Res Clin Oncol. 2003, 129(12): 669-75; Butz, K, et al, Oncogene. 2001, 20(45):6579-86; Garrido, C, et al, Cell Cycle 5:22, 2592-2601(2006); Guida, E., et al, Cancer Res. 68, 6550-6558 (2008). They disclose mutant p53-binding aptamers that are useful for this invention with suitable modification.

Hoppe-Seyler, F., et al, Curr. Mol. Med., 4, 529-538, (2004) and Hoppe-Seyler, F, et al, J Steroid Biochem Mol Biol. 78(2):105-11 (2001). They disclose methods and references for developing useful peptide aptamers for this invention with suitable modification.

Kaiser, N, et al, J Virology, 83, (2009), 11902-11913. Useful antiviral peptide aptamers for this invention, with suitable modification, against Human Cytomegalovirus that specifically bind with high affinity to the unconventional pUL84 NLS under intracellular conditions.

```
A4
                                 (Seq ID No: 95)
TRX - SSCNMGWDTPACCVWFPYWV - TRX

A8
                                 (Seq ID No: 96)
TRX - MAVGLVLCDWW LGEYLLELA - TRX

A56
                                 (Seq ID No: 97)
TRX - PVLQPALSLSCG PEP LLL SC - TRX

A110
                                 (SEQ ID NO: 98)
TRX - IEVTFVNRRGDGAELWYLSA - TRX
```

Kau, T R, et al, Drug Discovery Today 8, 78-85, (2003), disclose peptide aptamers that bind to CDK2, E2F, and the human papillomavirus E6 oncoprotein. These aptamers are active in vivo and useful for this invention with suitable modification. Kunz, C, et al, Mol Cancer Res 4, 983-998 (2006), disclose aptamers that bind the intracellular domain of the ErbB2 receptor of breast cancer. The following aptamers are also useful for this invention with suitable modification.

```
AI-1
                                        (Seq ID No: 99)
ALIMGCYVLVGTPRVVRFRS

AII-7
                                        (Seq ID No: 100)
LNFYRHGFLPNAVMASMLEVGPWFELLGLCGLAGHPLSSLRI

Ag-11
                                        (SEQ ID NO: 101)
GLAHGVAIYTELPLTRMARGG
```

Martel, V., et al, Oncogene 25, 7343-7353 (2006). They disclose a useful peptide aptamer for binding to protein kinase CK2 (casein kinase II); P1: GKMNGVLPLAWPS-LYLRLP (Seq ID No:102).

Nagel-Wolfrum, K, et al, Mol Cancer Res. 2004, 2 (3): 170-82; Proske, D, et al, Chembiochem. 2002, 3 (8): 717-25; Rerole, et al, Cancer Res; 71 (2) January 15, (2011). They disclose useful peptide aptamers A8 and A17 that are specific for inducible HSP70 and bind to distinct HSP70 domains, apparently without the need of scaffolds. The amino-acid sequences of the variable regions of the selected peptide aptamers follow. A8: SPWPRPTY (Seq ID No:103); A17: YCAYYSPRHKTTF (Seq ID No:104).

Schmidt, S., et al, FEBS Letters 523, 35-42 (2002). They disclose a peptide aptamer Rho-GEF inhibitor, TRIPK, is useful for this invention with suitable modification. It specifically targets the second Rho-GEF domain of the multifunctional protein Trio.

TRIPK: ASEGADGAICGYNLATLVMLGP-SERVFCPLCEPCSSDIYELM (Seg ID No: 105)

See, H. Y., et al, J. Mol. Biol. (2010) 404, 819-831. They describe a novel scaffold protein that is useful for this invention with suitable modification. It bypasses the conventional requirement for scaffolds to have known rigid structures and yet successfully presents several peptides that need to adopt a wide range of conformations for binding to their target protein. For this invention, an unstructured protein, 4EBP1, may work as scaffold, and use various aptamers such as binding aptamers for three different target proteins: Mdm2, proliferating cell nuclear antigen, and cyclin A.

Peptide aptamer Trx-eIF4G-ala., and a modified Trx-SGeIF4G aptamer with additional serine and glycine residues inserted (amino acid sequence SG-KKRYDREFLLGF (Seq ID No:106)) are useful for this invention with suitable modification. And includes other sequences in supplementary information of this reference.

Seigneuric, R., et al, Oncotarget 2, 557-561 (2011). They disclose, review and reference many aptamers for targeting cancer biomarkers useful for this invention with suitable modification, such as for the various drug delivery methods disclosed herein. Preferred peptide aptamers also include, with suitable modification, any types of peptide aptamers including peptide aptamers expressed from plasmid DNA. Receptor TM.

For this invention, a receptor is useful as a type of targeting moiety or molecule defined as a specific binding body or "partner" or "ligator" that can be larger than the ligand it can bind to. For the purposes of this invention, it is a specific substance or material or chemical or "reactant"

that is capable of selective affinity binding with a specific ligand, as disclosed in provisional Pat. App. No. 61/401,443, Aug. 13, 2010.
Transduction Vector TM.

Transduction vectors are known in the prior art under a wide variety of names. For this invention a transduction vector can be used as a targeting moiety (TM), and/or suitably incorporated into any suitable aptamer, and is defined as usually a peptide substance suitable for pharmaceutical use that promotes cellular uptake across the cell membrane and may include intracellular transport or trafficking, such as into the cell nucleus or mitochondria. Preferred transduction vectors or "fusion vectors" or "fusion moieties" or "membrane transduction" moieties are certain membrane translocation or membrane transfer peptides that can also include carbohydrates, lipids and polymers and combinations of these substances. Preferred transduction vectors are peptides ("fusion peptides" or "peptide vectors") including those with "transduction domains" in their amino acid sequence, as disclosed in provisional Patent Application No. 61/401,443, filed Aug. 13, 2010.

Some preferred transduction vectors for this invention include, but are not limited to, any derived sequences or extracts of any signal peptides (i.e. NLS) or any fusogenic peptides including: TAT (i.e. from HIV virus), herpes simplex virus VP-22, hepatitis B virus PreS2 translocation motif (TLM) and antennapedia homeoproteins (i.e. penetratins). Preferred transduction vectors also include poly arginines (i.e. containing 5 or more, preferably from 6 to 12 arginines and with or without one or more terminal cysteines), poly histidines, poly lysines, poly ornithines and combinations of these amino acids with or without one or more terminal cysteines.

With suitable modification, preferred carriers, nanocomplexes, nanoparticles and other scaffolds, including suitable synthesis methods, for preparing, carrying and intracellular delivery of the flexible aptamer compositions of this invention are disclosed by Li, X. et al, J. Cont. Rel. 171, 152-162 (2013), Kim, M., et al, Molecules 23, 830 (2018) for cancer targeting, Li, D., et al, Nat. Scientific Reports 8:10196 (2018) for use of a multifunctional DNAzyme "nano-scorpion" nanostructure that cleaves specific mRNA.

Also, Soliman, M., et al, Mol. Pharmaceutics 9, 1-13 (2012) for DNA delivery vectors based on coated nanoparticles with a polyanionic peptide core and a viral-mimetic core-shell architecture.

Shi, B., et al, Biomacromolecules 18, 2231-2246 (2017) for a multifunctional DNA delivery vector with a cRGD peptide moiety and a hydrophobic cholesteryl moiety on the α- and ω-ends of PEG-PAsp (DET) block copolymers (cRGD-PEG-PAs(DET)-chol), Also included are the peptide vectors disclosed by P. M. Fischer, et al, in Reviews Bioconj. Chem 12, 825-841 (2001) and references therein. Preferred examples of transduction vectors in this invention are peptide vectors which have been employed for transport of active agents including nucleic acids into cells. Preferred examples include conjugates of a carrier substance with penetratins or signal peptides to increased uptake rates due to the membrane translocation properties of these peptides. Table I. is a list of some peptides that are preferred transduction vectors in this invention.

TABLE I

Transduction Vector TMs

| TRANSDUCTION VECTOR SEQUENCE | NAME (origin of sequence) |
|---|---|
| RQIKIWFQNRRMKWKK (Seq ID No: 107) | pAntp(43-58); Penetratin |
| KKWKMRRNQFWVKVQR (Seq ID No: 108) | retro-inverso pAntp(43-58) |
| RRWRRWWRRWWRRWRR (Seq ID No: 109) | W/R Penetratin |
| RQIKIWFQNRRMKWKKEN 24 (Seq ID No: 110) | antennapedia peptide |
| RRMKWKK (Seq ID No: 111) | pAntp(52-58) |
| GRKKRRQRRRPPQ (Seq ID No: 112) | HIV TAT |
| YGRKKRRQRRR (Seq ID No: 113) | HIV TAT |
| PTSQSRGDPTGPKE (Seq ID No: 114) | HIV TAT C-terminus peptide |
| AVGAIGALFLGFLGAAG (Seq ID No: 115) | viral fusion peptide |
| GALFLGWLGAAGSTMGA (Seq ID No: 116) | gp41 fusion sequence |
| GALFLGFLGAAGSTMGAWSQPKSKRKV MPG(Seq ID No: 117) | (gp41 fusion sequence SV40 NLS) |
| DRVIEVVQGAYRAIRNIPRRIRQG (Seq ID No: 118) | CR-gp41 fusion peptide |
| MGLGLHLLVLAAALQGA (Seq ID No: 119) | C. crocodylus Ig(v) light chain |
| MGLGLHLLVLAAALQGAWSQPKKKRKV (Seq ID No: 120) | C. crocodylus Ig(v) light chain-SV40 NLS |
| PLSSIFSRIGDP (Seq ID No: 121) | PreS2-TLM |
| GWTLNSAGYLLGKINLKALAALAKKIL (Seq ID No: 122) | Transportan |
| RGGRLSYSRRRFSTSTGR (Seq ID No: 123) | SynB1 |
| AAVALLPAVLLALLAP (Seq ID No: 124) | MPS (kaposi FGF signal sequence) |
| AAVLLPVLLAAP (SEQ ID No: 125) | MPS (kaposi FGF signal sequence) |
| VTVLALGALAGVGVG (Seq ID No: 126) | MPS (human integrin beta3 signal seq) |
| VAYISRGGVSTYYSDTVKGRFTRQKYNKRA (Seq ID No: 127) | P3 |
| KLALKLALKALKAALKLA (Seq ID No: 128) | Model amphiphilic peptide |
| WEAKLAKALAKALAKHLAKALAKALKACEA (Seq ID No: 129) | KALA |
| GLFEAIAGFIENGWEGMIDGGGYC (Seq ID No: 130) | hemagglutinin envelope fusion peptide |
| RRRRRRR (Seq ID No: 131) | R7 |
| AAVALLPAVLLALLAPVQRKRQKLMP (Seq ID No: 132) | engineered |
| MGLGLHLLVLAAALQGAKKKRKV (Seq ID No: 133) | engineered |

Cell Receptor Binding Peptide TM.

Preferred targeting moieties are cell receptor binding peptides (i.e. peptide aptamers and ligands), that bind to distinct receptors, which upon binding, may also mediate endocytosis of a peptide-ODN complex. Also included are peptides which bind to integrins and to the EGF receptor family. In U.S. patent application Ser. No. 10/923,112, Table II. is a list of some receptor binding peptides that are preferred in this invention.

TABLE II

Receptor Binding Peptide TMs

| RECEPTOR BINDING PEPTIDE SEQUENCE | NAME (function) |
|---|---|
| TQPREEQYNSTFRV (Seq ID No: 134) | Fc receptor binding peptide |
| D-GCSKAPKLPAALC (Seq ID No: 135) | antagonist to IGF-1 receptor |
| YGGFLRRG (Seq ID No: 136) | beta-endorphin receptor ligand |

TABLE II-continued

| Receptor Binding Peptide TMs | |
| --- | --- |
| RECEPTOR BINDING PEPTIDE SEQUENCE | NAME (function) |
| YEE(ah-GalNAc)3 | hepatocyte specific delivery |
| Z-D-Phe-L-Phe-Gly | cell fusion and hemolysis inhibitor |

Other preferred receptor binding peptides include other; Fc receptor binding peptides, antagonists to IGF-1 receptors, beta-endorphin receptor ligands, hepatocyte specific delivery peptides, tuftsin (Thr-Lys-Pro-Arg), and cell fusion and hemolysis inhibitor peptides.

FORMULAS AND EXAMPLES

In some embodiments the drug is coupled noncovalently, as defined herein, to the carrier. In this example, the drug is suitably sequestered or entrapped noncovalently within the closed form of the carrier so that it cannot be released. Such entrapment can be further accomplished through opposite charges between the drug and carrier, or by hydrophobic forces. When mechanical force is applied to open the carrier, the drug is released by allowing it to diffuse away (i.e. passive release).

In an active release embodiment, defined herein, the active agent or drug includes coupling to a suitable, specific targeting moiety (TM), defined herein, through a covalent, cleavable linkage. However, the linkage is sequestered or protected within the carrier's closed molecular structure (i.e. embedded or sterically hindered) and may include a hydrophobic environment. When mechanical force is applied, the carrier changes shape to an open form or shape, which exposes the linkage to allow cleavage from external forces. The cleavage and release of the drug can then occur through various suitable means such as hydrolysis of an ester bond or Schiff's base, reduction of a disulfide bond, oxidation of vicinal hydroxyls or by enzymatic cleavage (i.e. cathepsin B, L, V, etc.), of specific peptide linkages.

Said TM may be one or more TMs, as disclosed herein and said definitions include all disclosures and all references therein from previously filed Provisional App. 62/786,340, with the same or different specificities suitable for the instant invention. In some preferred embodiments, said TM can include any suitable antibody, including engineered Ab or Ab fraction or Ab scaffold, defined herein.

In some preferred embodiments, said TM can include any suitable nucleic acid such as DNA, RNA, oligonucleotides, peptide nucleic acids (PNAS) and nucleic acid aptamers, defined herein.

In some preferred embodiments, the TM can include any suitable peptide, peptide aptamer, peptide ligand or protein, including enzymes or enzyme fragments, engineered enzymes, receptor proteins, zinc finger proteins, engineered zinc finger proteins and their fragments, defined herein.

In the following examples, the flexible carrier can be any suitable carrier described herein. And wherein the force required to change conformation of the carrier from closed to open (i.e. to separate active agent from carrier), is less than the binding forces between the TMs and their target substance.

Where antibody is used to represent the specific binding moiety, the antibody can be suitably substituted for other TMs, described herein. Also, the drug used in the following examples can be any suitable active agent described herein.

Flexible Carrier with Anti-Motor Protein Aptamer.

There are useful, flexible, molecular "motor proteins", as target substances that capable of moving other proteins and organelle "cargo" through their interactions with the actin and microtubule networks using changes in conformation. The cellular motor protein kinesin-2 is required for the normal movement of late endosomes or lysosomes.

Also useful is the cytoplasmic motor protein dynein, which moves endosomes and lysosomes toward the minus ends of microtubules and the motor protein kinesin-1, which moves them toward the plus ends. These three motor proteins are complexes composed of 'heavy chains' and several other subunits, including 'light chains' and 'intermediate chains' in the case of the dynein, that regulate their motor activity and cargo attachment.

In this embodiment of this invention, these and other motor proteins can be employed as target substances for exerting physical force (i.e. Nanoforces™), such as pulling, stretching, rotating and/or bending a flexible carrier of this invention, to change its conformation from closed to open and thereby release a drug. Suitable motor proteins useful in this invention, with suitable modification as needed, are disclosed by Roberts, et al, Phil. Trans. Royal Soc. B. (2004), 359, 1931-1944; and Ito, et al, J. Biol. Chem 282, 19534-19545 (2007), and references therein which are incorporated herein.

In one preferred embodiment, the composition is a flexible drug carrier aptamer carefully designed and synthesized with a specific mass and shape so that it can suitably contain an active agent covalently coupled through a cleavable linkage, as defined herein. Said flexible carrier can be any suitably shaped aptamer, protein, peptide or peptide nucleic acid, defined herein, (i.e. alpha helix, opposing beta sheets, beta barrel, hairpin, looped, zipper), or suitably coiled or stacked polymers and grafted polymers, defined herein (i.e. HPMA), including any suitable nucleic acid (i.e. DNA, RNA, locked nucleic acid, backbone derivatized nucleic acid, etc.), described herein.

Included in the composition of said flexible carrier aptamer, is at least two corresponding aptamer TMs, designated as TM-A and TM-B, each one suitably located at, or near, each end of a single aptamer carrier strand or sequence (i.e. bifunctional). Alternatively, at strategic sites, said TMs are covalently coupled.

In either case, said TM-A can be specific for any suitable intracellular target substance that can be relatively mobile or stationary, (i.e. anchoring substance), as defined herein. Said target substance can be a microbe, virus or any suitable intracellular substance, or biomarker such as any suitable mutant protein including multidrug resistant protein (MRP), or mutant p53 protein, defined herein.

Suitably, said TM-A is specific for any suitable disease marker such as a mutated or fusion protein involved in cancer, or other diseases. Alternatively, said TM-A can be specific for a disease organism such as a virus, bacterium or parasite, or specific for suitable antigenic markers from these organisms. Preferably, said TM-A is specific for a target substance that has suitably mass to provide a certain amount of inertia, and/or is a ligand suitably anchored to an organelle or intracellular matrix to resist movement.

Said TM-B is specific for any suitable motor protein, defined herein, with the requirement that when TM-B binds to said motor protein, the motor protein can continue to function (i.e. is not inhibitory).

Said flexible carrier aptamer also contains any suitable active agent covalently coupled through a cleavable linkage, (i.e. self immolative), as defined herein, to said carrier.

Alternatively, said active agent can be suitably coupled by a cleavable linkage, defined herein, to a suitable noncovalent coupler substance (NCS), defined herein, to provide an active agent-NCS, defined herein. In this case, said carrier is noncovalently coupled to said NCS moiety of said active agent-NCS.

In any case, said carrier composition contains a suitable active agent (drug) covalently coupled or entrapped in the carrier in its "closed" form (i.e. protected from release). Suitably, said cleavable linkage between said active agent and said carrier is suitably protected sterically from cleavage, as defined herein.

The resulting composition is a motor protein bindable carrier composition, capable of binding a target substance (i.e. disease antigen) through TM-A and a functional motor protein through TM-B. With suitable modification, either said TM-A or TM-B can represent more than one TM.

Without being limited to any specific theory or mode of action, one of the expected courses of action (or scenarios) would be as follows. Upon entering a cancer cell containing suitable biomarkers for disease (through various well known cell penetrating strategies), said TM-B will bind specifically to a suitable motor protein, and the entire carrier composition will be pulled along by the motor protein in the cell. However, if said carrier is inside a diseased cell, such as a cancer cell with mutant p53, or a virus infected cell, said TM-A will also have a target to bind.

The intended result will be the added mass of said carrier due to the specifically bound target substances at opposing ends or sides of the carrier composition. The additional molecular mass, in combination with the movement of said motor protein, is designed to provide inertia and/or pulling force in opposing directions on the carrier composition.

The resulting pulling force will exert a suitable mechanical force upon said carrier, causing a conformational change to the "open" form, wherein said cleavable linkage to said active agent is no longer protected or sequestered. Said cleavable linkage between said active agent and said carrier is thereby exposed to suitable conditions, defined herein, to cause cleavage and release of said active agent.

The carrier composition is so designed to be "Force Responsive" so that if only one of said TMs are specifically bound, then the carrier will remain closed until the corresponding TM, is also specifically bound. The purpose is that there is little or no chance for non-specific release of active agent.

In another preferred embodiment of this invention, said TM-B is replaced with a suitable TM that is specific for an intracellular organelle such as a mitochondrium, centromere, microsome or golgi apparatus among others. In this embodiment, said organelle will provide a suitable pulling force through normal intracellular circulation and other movement.

Flexible Carrier for Extracellular Binding.

In another preferred embodiment of this invention, said carrier is suitable for extracellular applications. In this embodiment, said TM-A is specific for any suitable cell surface disease biomarker, and/or an over expressed receptor such as a protein or ligand associated with a specific disease.

And, said TM-B is specific for a suitable cell surface protein or receptor such as multidrug resistant proteins, adherins, clathrins, lipid raft, etc., or is specific for a suitable part of the extracellular matrix (EM), including collagens and metalloproteinase, among others.

Aptamer Drug Carrier Compositions.

In the examples provided herein, a flexible drug carrier aptamer composition is carefully designed and synthesized with a specific mass and shape described previously. Said composition can be comprised of two (2) aptamers wherein some of the sequences are complementary with each other at suitable locations to allow formation of a hybridized composition (i.e. "zipper"), or duplex carrier, defined herein.

For all exemplary compositions of this invention, suitable Aptamers and Targeting Moieties represented as TM-A, TM-B, TM-C, etc., are suitably prepared from any useful aptamers, peptide aptamers, capture probe sequences and/or ON and ODN sequences disclosed herein, and by Farjami, E., et al, Anal. Chem. 83, 1594-1602 (2011); Soon, J. O., et al, Nucleic Acids Res. 33, No. 10 e90 (2005) and Olivier, M., et al, Hum. Mutat. 19, 607-614 (2002).

Said drug carrier aptamers and/or ON's and ODN's include, but are not limited to, aptamers that target mutated DNA or RNA, any mutated proteins including p53 proteins, disclosed herein, and any types of nucleic acid aptamers (i.e. DNA or RNA) or peptide aptamers or peptide nucleic acid (PNA), and bi-specific (bifunctional), aptamers.

Aptamers are prepared using any suitable synthesis methods in the art, including, but are not limited to, the use of any modified nucleic acids, phosphoramidites and methods disclosed by; Afonin, K A, et al, ACSNano 9, 251-259 (2015), for suitable DNA, RNA and hybrid duplex nanoparticles; Au, JL-S., et al, Adv Drug Deliv Rev. (2016) 97:280-301; Becker, R. C., et al, Thromb Haemost. (2005), 93 (6): 1014-20; Chen, L, et al, PNAS 112, 10002-10007 (2015), for useful RNA aptamers that bind mutated p53 protein, R175H, including RNA sequence called p53R175H-APT; ATTAGCGCATTTTAACATAGGGTGC (Seq ID No: 137) among others; Cohen, J. D., et al., Science 10.1126/science.aar 3247 (2018) and including all methods, sequences, references and supplementary information therein.

Said TMs can be suitably covalently coupled to said aptamer or synthesized as a continued sequence of nucleotides or peptides to become part of the composition. Said TMs can suitably include any antibodies, Fab fragments and antibody scaffolds, disclosed herein and most preferred are antibodies that target mutated p53 proteins, disclosed herein.

In another preferred embodiment, said composition can be comprised of a single aptamer "strand" wherein some of the sequences are complementary with each other at suitable locations to allow formation of a folded, or "zipper", self-hybridized composition. Said folded compositions are well known and can form stems, zippers, and/or loop structures useful in this invention. Any of said aptamers can include amino acids, nucleic acids (or respective strands), that can include ON, ODN, mixed backbone ON or mixed backbone ODN, or chimeric nucleic acids wherein some of the sequences are complementary.

Said aptamers also include one or more targeting moieties (TMs) within their sequence structure. Alternatively, at strategic sites, said TMs are covalently coupled. In all the examples provided herein, where applicable, all iterations of said TM, including TM-A, TM-B, TM-C, $(TM)_R$, $(TM-A)_R$, $(TM-B)_R$, $(TM-C)_R$, etc., is a suitably selected targeting moiety including for cell receptors, intracellular targeting and/or facilitates intracellular trafficking, as defined herein.

In addition to being said targeting moiety, TM may also be a member independently selected from the group consisting of hydrogen (H), hydroxyl (OH), halogen, transduction vectors (TV), nuclear location sequences (NLS), amphiphilic molecules, grafted polymer and capping moieties.

Also with the proviso wherein said flexible carrier substance can contain a suitable combination of active agents (with cleavable linkages), functional groups, halogens, targeting moieties, cell transduction vectors, amphiphilic molecules and grafted polymers, as defined herein, that are coupled on the same flexible carrier substance and/or are within the same flexible carrier substance composition.

Said coupling between said active agent or active agent-NCS, and said carrier aptamer is designed so that said agent, and/or cleavable linkage, is wholly or partially sequestered (or sterically hindered) while said composition is in its closed shape or form, as defined herein.

Without imposing limitations on the scope of this invention, the mechanism for preventing cleavage of said cleavable linkages when the flexible carrier is in its closed form is through steric hindrance and/or physical or molecular obstruction that prevents cleavage of the linkage.

Said steric interference is suitably caused by the design and/or nucleic acid sequences of said carrier, as disclosed herein, that provide a suitable structure or shape when in said closed form that interferes with cleavage of said cleavable linkages. Also, said steric interference can be suitably caused through the incorporation (i.e. added by suitable derivatization) of sterically interfering molecules, or bulky moiety, as disclosed herein, into said carrier, resulting in suitable steric interference of said linkages when said carrier is in said closed form.

Drug Carrier Aptamers with Stem-Loop for Noncovalently Coupled Active Agents.

Drug carrier aptamers that are useful in this invention, with suitable modification as needed, are disclosed by references herein. The following Diagrams include exemplary sequences of nucleic acids that form a "stem" or "stem-loop" or "zipper" defined herein.

Said sequences are shown within brackets { } to mean that said sequences can be partially or wholly complementary, as needed, and can be suitably modified by changes in their order, number and/or chemical composition. Said stem sequences can include any suitable secondary structure such as more than one hybridized stem region, additional loops and/or partial hybridizations and/or sections of noncomplementarity of the nucleic acid strand that can produce "bulges" or "hairpin bulges" in said stem regions.

The Diagrams Represent Drug Carrier Aptamers with Alternatively Coupled Active Agents.

In some embodiments of this invention, one flexible DNA aptamer strand is used in a flexible carrier composition that has suitably complementary NA (base) sequence regions at or near each end to produce a "stem-loop" nucleic acid aptamer when folded and partially hybridized upon itself.

Alternatively, any suitable complementary base sequences can be substituted, added or subtracted in this strand to provide the desired melting temperature and the desired binding affinity between said stem regions. Also, any nucleic acid bases in said aptamer can be suitably substituted with backbone derivatized bases, defined herein, or with phosphoramidites, or with RNA, or with LNA, or with PNA, defined herein, or combinations of these.

Where applicable, the Symbol; [↕⊃ DRUG] represents noncovalent coupling of said active agent. Said noncovalent coupling can be through intercalation with the hybridized nucleic acid strands in the "stem" section of the aptamer, at any suitable location on said stem.

The Symbol; [↕⊃ NCS - CL - DRUG] represents a "noncovalent coupler substance" (NCS), that includes a therapeutic active agent coupled to said NCS (active agent-NCS), with a cleavable linkage (CL), defined herein.

Said NCS is intercalated with the hybridized nucleic acid strands in the "stem" section of the aptamer at any suitable location on said stem.

Any open Dash ⊏⊐; or open Plus ⊕; or open Arrows ↕⊃ symbols represent noncovalent coupling, defined herein, between any suitable moieties including a Cleavable Ligand Linkage (CLL), and any oligonucleotide "sticky ends", and Ligand Binding Domain (LBD), or suitable antibody.

Said noncovalent coupling can include suitable intercalation with suitable nucleic acid strands. The TM-Loop symbol, (TM)↩ represents a nucleic acid or amino acid sequence forming the "targeting moiety loop" or TM-loop region of said aptamer that also functions as a TM, defined herein. The TM-loop region of said aptamer can be any suitable sequence or strand, of nucleic acids, or amino acids, defined herein, designed to specifically bind with the desired target substance and can be suitably modified by changes in their order, number and/or chemical composition. Said TM-loop region can also include any suitable secondary structure such as more than one hybridized stem region, additional loops and/or partial hybridizations and/or sections of noncomplementarity of the strand that can produce "bulges" or "hairpin bulges" in said stem regions.

"DRUG", is any suitable therapeutic active agent, defined herein, suitably coupled to provide the desired function for the example it is presented in. Said DRUG can be covalently coupled or can be noncovalently coupled, such as by intercalation or through a "noncovalent coupler substance" (NCS), that includes an "active agent-NCS", defined herein, intercalated to said nucleic acid stem at any suitable position along the length of said stem. Said noncovalent coupling can be through major or minor groove binding, as defined herein.

Said $(TM\text{-}A)_R$ or $(TM\text{-}B)_R$ is any suitable targeting moiety, defined herein. Alternatively said $(TM\text{-}A)_R$ or $(TM\text{-}B)_R$ is any suitable optional substance, that said carrier may or may not be further coupled to, as defined herein.

P is any suitable amino acid, nucleic acid, amino acid, nucleotide, phosphoramidite, LNA or PNA, as disclosed herein, located at any suitable position, including at or near the end of said nucleic acid strand. P may be suitably derivatized to provide a functional group (i.e. sulfhydryl, amino or carboxyl), for covalently coupling through said linkage (L) to optional substance X.

$(AAA)_R$ is any suitable group or alternate sequence of amino acids, nucleic acids or nucleotides, that function as spacers wherein R is an integer between 1 and 30, preferably between 2 and 10.

When applicable, L is any suitable covalent linkage, defined herein, between said nucleic acid strand (flexible carrier) and any suitable substance. Said covalent linkage (L) between said nucleic acid strand and said suitable substance, can also include one or more carbon atom spacer units; $(CH_2)_R$ described herein.

$(CH_2)_R$ represents said spacer units, defined herein, wherein R is an integer 0 (meaning no spacer), or an integer between 1 and 30, preferably between 2 and 10.

Said $(CH_2)_R$ can be any suitable spacer moiety, that includes hydroxyls, amino groups or carbonyl groups, or combinations of these.

Drug Carrier Aptamers with Covalently Coupled Active Agents.

The active agent is covalently coupled to a suitable "stem-loop" carrier aptamer.

The exemplary Diagrams include exemplary sequences of any nucleic acids or peptides, defined herein, that form a "stem" or "zipper" defined herein. Said sequences are shown within brackets { } to mean that said sequences can be partially or wholly complementary, as needed, and can be suitably modified by changes in their order, number and/or chemical composition.

Said stem or zipper sequences can also include any suitable secondary structure such as more than one hybridized stem region, additional loops and/or partial hybridizations and/or sections of noncomplementarity of the nucleic acid strand that can produce "bulges" or "hairpin bulges" in said stem regions.

Said bulges in said stem region can suitably contain one or more suitably modified or functionalized amino acid, nucleic acids (i.e. phosphoramidite), (P or suitably X), defined herein, that provides covalent coupling to said "CL-Drug". And it is understood that wherein certain moieties are symbolized and/or described in one diagram, they are suitably applicable, when present, in other sample diagrams of this invention.

In some examples of this invention, one flexible DNA aptamer strand is used in a flexible carrier composition that has suitably complementary NA (base) sequence regions at or near each end to produce a "stem-loop" DNA aptamer when folded and partially hybridized upon itself.

Alternatively, any suitable complementary base sequences can be substituted, added or subtracted in this strand to provide the desired melting temperature and the desired binding affinity between said stem regions. Also, any nucleic acid bases or peptides in said aptamer and/or composition can be suitably substituted with any modified NA, backbone derivatized NA, and/or with RNA, with LNA, with PNA, defined herein, or combinations of these.

The following Diagrams represent Drug Carrier Aptamers with alternatively coupled active agents.

Wherein said "TM LOOP" is suitably incorporated Aptamer sequence p53175H-APT.

In other embodiments, said $(TM-A)_R$ or $(TM-B)_R$ is a suitable RNA moiety such as a crRNA or sgRNA, defined herein. And in other optional embodiments said crRNA or sgRNA is bound within any suitable protein including any suitable CRISPR Cas9 protein or Cas12a protein, referenced and/or defined herein. And in other preferred embodiments said $(TM-A)_R$ or $(TM-B)_R$ is suitably Aptamer sequence p53175H-APT.

And in other preferred embodiments said Aptamer sequence p53175H-APT is substituted for any suitable aptamer in any suitable nanoparticle examples, disclosed herein.

The Symbol; $\boxed{\textbf{CL - DRUG}}$ or "DRUG-CL" represents a composition comprising said CL, defined herein, and a covalently coupled, therapeutic active agent (CL-DRUG), defined herein, covalently coupled to a suitable nucleic acid or phosphoramidite, defined herein, in a suitable "stem" or "loop" or "bulge" section of said aptamer.

The TM-Loop symbol, represents a nucleic acid sequence forming the "targeting moiety loop" or TM-loop region of said aptamer that also functions as a targeting moiety (TM), defined herein.

The nucleic acid sequence forming the TM-loop region of said aptamer can be any suitable sequence of nucleic acids, defined herein, designed to specifically bind with the desired target substance (i.e. biomarker). Said TM-loop region can also include any suitable secondary structure such as more than one hybridized stem region, additional loops and/or partial hybridizations and/or sections of noncomplimentarity of the nucleic acid strand that can produce "bulges" or "hairpin bulges" in said stem regions.

Alternatively, said TM-Loop is replaced with a suitable nonbinding that contains suitable nucleic acids or amino acids (i.e. proline), to provide said structural loop or bulge without specific TM binding. Alternatively, said nonbinding loop also contains any suitable functional group and/or phosphoramidite suitably derivatized to provide a functional group (i.e. sulfhydryl, amino or carboxyl), at a suitable location for covalently coupling to an active agent through a suitable cleavable linkage, defined herein.

In all the examples disclosed, said "CL-DRUG", is a composition comprising at least two components.

"DRUG", is any suitable therapeutic active agent that is covalently coupled through a cleavable linkage, represented by "CL", (including peptides), as defined herein.

Said CL is suitably coupled through a suitable functional group provided on said P (or suitably X), defined herein, and can also include one or more spacer units; $(CH_2)_R$ described herein.

Symbol P (or suitably X), is any suitable amino acid, nucleic acid, nucleotide, phosphoramidite, LNA or PNA, as disclosed herein, located at any suitable position, including at or near the end of said strand of ON and/or ODN, RNA, DNA or peptide strand.

P or X may be suitably derivatized to provide a functional group (i.e. sulfhydryl, amino or carboxyl), for covalently coupling through said linkage (L) or (CL). Said $(TM-A)_R$ or $(TM-B)_R$ is any suitable targeting moiety, including for cell receptors, intracellular targeting and/or facilitates intracellular trafficking, as defined herein. Alternatively said (TM-A) R or (TM-B) R is any suitable optional substance coupled to said carrier, as defined herein.

$(AAA)_R$ is any suitable group or alternate sequence of amino acids, nucleic acids or nucleotides, that function as spacers wherein R is an integer between 1 and 30, preferably between 2 and 10.

L is any suitable covalent linkage, defined herein, between said nucleic acid strand (flexible carrier) and any suitable substance.

Said covalent linkage (L) between said nucleic acid strand and said suitable substance, can also include one or more carbon atom spacer units; $(CH_2)_R$ described herein.

$(CH_2)_R$ represents said spacer units wherein R is an integer 0 (meaning no spacer), or an integer between 1 and 30, preferably between 2 and 10. Said $(CH_2)_R$ can be any suitable spacer moiety, that includes hydroxyls, amino groups or carbonyl groups, or combinations of these.

Without imposing limitations on the scope of this invention, the mechanism for release occurs during or after said binding, when the aptamer and/or carrier undergoes a sufficient physical change in shape, size or position (i.e. conformation change) due to physical, molecular or macromolecular mechanical forces as a result of, or made possible by or induced by, the specific binding.

Said conformational change is designed to include suitable separation or "unzipping" of previously hybridized sequences in the stem portion of a suitable carrier nucleic acid aptamer, that subsequently releases the active agent.

Preferably, suitable mechanical force or binding force, defined herein, can be applied to open said flexible carrier composition to allow release of said active agent from said carrier.

The mechanical force, measured in piconewtons (pN), is suitably in the range between 2 and 10,000 pN, and will also take into account the rate at which said force is applied.

Conversion to a Nanoparticle Flexible Carrier Composition.

With suitable modifications as needed, any of the composition examples provided can also function as Nanoparticle Flexible Carrier Compositions, defined herein. For instance, where shown, said representative substance (TM-A)$_R$ or (TM-B)$_R$, etc., is suitably any suitable nanoparticle or micelle, defined herein.

The resulting substance or component coupled to said nanoparticle can then function as said NanoParticle Component (NP Part), defined herein. And, the substance or component with coupled active agent can function as the Active Agent Component (AA Component), defined herein.

Any said components can be suitably modified or derivatized as needed, wherein any suitable block polymers, lipids or amino acid residues can be derivatized, substituted, added or subtracted in the compositions to provide the desired structure, properties, functional groups and/or binding affinities between said components.

Said representative NanoParticle Part (NP) represents any suitable carrier substance or structure, useful with suitable modification for this invention, that includes nanoparticles, nanostructures, nanocarriers, proteins, peptides, PNA, nucleic acids (NA), RNA, DNA, L-RNA, L-DNA, LNA, and modified NA. Most preferred is the suitable use of modified peptides and modified NA to reduce or prevent undesired cleavage or degradation of said compositions and/or provide functional groups for subsequent coupling to other moieties, defined herein.

Also in the examples, with suitable modification, useful structures and/or nanostructures include NA Holliday junctions, cruciform NA, NA G-quadruplexes, NA Tetrahedrons, albumins, nanospheres, nanotubes, microdots, nano-dots, dendrimers, micelles, liposomes, polymeric nanoparticle or protein nanoparticle or macromolecule, and any suitable Biomaterials for drug delivery as defined herein.

For instance, said representative substances (TM-A, B, C, D, E, F)$_R$, etc., is suitably coupled to any suitable nanoparticle or micelle, defined herein. The resulting substance or component coupled to said nanoparticle can then function as said NanoParticle Component (NP Component), defined herein.

Double Bar Symbol; ▬ represents any suitable coupling substance and/or coupling method that provides either covalent or noncovalent coupling of the indicated moiety to the particular nanoparticle, micelle or liposome used in the example. And, wherein the substance or component with coupled active agent can function as the Active Agent Component (AA Component), defined herein.

Either component can be suitably modified or derivatized as needed, wherein any suitable block polymers, lipids or amino acid residues can be derivatized, substituted, added or subtracted in this composition to provide the desired structure, properties, functional groups and/or binding affinities between said components.

Also in the examples, with suitable modification, said nanoparticle or micelle can be any suitable carrier substance such as a liposome, stealth liposome, nanosphere, microdot, dendrimer, polymeric nanoparticle or protein nanoparticle or macromolecule, as defined herein.

Holliday Carrier NanoParticle with Zipper Motifs and Suitable TMs.

In a preferred example, a suitably modified Holliday junction is employed as a "Holliday NP" carrier structure to synthesize a flexible, force responsive composition of this invention.

The composition is based on modifications of the cross-like nanostructures disclosed by Tung, et al, in Nature: Scientific Reports 7, 793 (2017) and Li, Z. Y. et al, Angew. Chem. Int. Edit 54, 11706-11710 (2015), and Wikipedia.org, among others, and is generally comprised of 4 nucleotide, or nucleobase "strands" that are suitably complementary to form a 4-Armed nanostructure wherein each arm is double stranded for a sufficient distance from the center.

And wherein any said arms can also function as zipper-like or hairpin-like structures that can include suitable phosphoramidites (P or X), for covalent coupling of active agents, defined herein.

Said Holliday NP is suitably modified to provide the required stability against undesired strand migration and can have any suitable aptamers attached and/or incorporated, such as aptamer (AS1411) suitably modified to allow annealing with one of the arms via a sequence specific 'sticky' end. Any of the 5' ends and/or the 3' ends of said strands can be suitably modified to provide functional groups including amine groups and/or thiol groups for suitable conjugation, or capping, etc. The remaining three arms are comprised of overhanging sequences for suitable attachment of targeting moieties (TM), with the desired properties of specific binding, disease targeting and/or intracellular trafficking. Said attachment can be through covalent conjugation and/or annealing, and/or synthetic extensions of one or more strands with suitable nucleotides to provide the desired sequences and properties.

Said Holliday NP Example shown has a zipper-like motif that includes covalent coupling of active agent ("DRUG") through a Cleavable Linkage (CL) to a suitable functional group provided by any suitably modified nucleotide or phosphoramidite. In addition, said CL is suitably sequestered within any suitable Arm with said zipper-like form, which can include a suitable structural "bulge" to provide space for said CL and said active agent. Said Holliday NP Example shown has suitably coupled Targeting Moieties: (TM-A, B, C, D, E, F)$_R$ that can be the same or different specificity, as needed and can target any suitable 30° disease substance, as defined herein.

Said Holliday NP Example shown also has aptamers: (Apt-A, B, C, D, E)$_R$ that can be the same or different, as needed and of any suitable sequence, as defined herein.

Alternatively, any suitable complementary base sequences can be substituted, added or subtracted in the strands to provide the desired melting temperature and the desired binding affinity between said stem and/or zipper regions. Also, any nucleic acid bases or peptides in said aptamer and/or composition can be suitably substituted with any modified NA, backbone derivatized NA, with RNA, with LNA, with PNA, defined herein, or combinations of these.

Example Diagram XIII. Carrier Aptamer Quadruplex Composition with Zipper Extensions The structure labeled "{APTAMER}" is exemplary for suitably modified aptamer AS1411, or AGRO100, which comprises two nucleotide strands of AGRO100 folded in antiparallel orientation to form a bimolecular quadruplex nanostructure containing eight G-quartets, which can be suitably stabilized as needed by intercalation and/or covalent crosslinking. And wherein said aptamer has suitable nucleotide extensions that provide suitable "zippers" through complementarity of the sequences used.

Also provided are optional Targeting Moieties (TMs), suitably covalently coupled at or near the 5' ends of said zippers. Said (TM-A), (TM-B) or (TM-C) is any suitable TM, including for cell receptors, intracellular targeting and/or facilitates intracellular trafficking, as defined herein. Alternatively, said (TM-C) is any suitable optional substance coupled to said carrier, as defined herein.

Also for said aptamer quadruplex, suitably included within said zippers are moieties designated as "X", which represent one or several (i.e. 2, 3, or more) suitable nucleotides, or phosphoramidites or other moieties that provide functional groups and/or cleavable covalent linkages, defined herein, for covalent coupling and is suitably coupled to provide the desired function for the example it is presented in.

And wherein said "X" moieties can also provide a suitable space, or bulge within said zipper structures that provide suitable steric hindrance or protection for said linkage from cleavage while said zipper is in a closed conformation, defined herein.

In all the Examples in this invention, said {PEG} symbol, optionally represents, any suitable polymer that preferably provides low- or non-immunogenic properties. Included are suitable grafted polymers, (i.e. HPMA), responsive polymers, amphiphilic grafted polymers and/or block polymers, defined herein.

Carrier Aptamer Tetrahedron Composition with Zipper Motifs.

Example Diagram XIV. Carrier Aptamer Tetrahedron Composition with Zipper Motifs Said example Carrier Aptamer Tetrahedron of this invention is inspired with suitable modifications for this invention from the prior art, including disclosures by Charoenphol, C., et al, Mol. Pharmaceutics 11, 1721-1725 (2014) and Lee, H., et al, Nat. Nanotechnol. 7, 389-93 (2012), among others.

Said aptamer tetrahedron is suitably composed of any suitable ON and/or ODN strands that are combined and thermally annealed to self-assemble into a pyramid cage nanostructure with four triangular faces and six double-stranded edges.

Said sequence design is suitably modified to have suitably complementary strands of 30 bp on each side of the tetrahedral nanoparticle along with, at the 3' end, an optional, or a suitable X moiety, defined herein, and/or said X moiety is a suitable overhang or a functional group (i.e. —SH) at the 3' end defined herein, or optionally, an X moiety is optionally at the 5' end or is not provided at certain ends and those ends are suitably ligated as disclosed in the art.

And wherein said suitable complementary strands provide optional zipper motifs or structures that optionally contain additional X moieties within said zipper motifs, designated here as "Zipper X" moieties. Said Zipper X moieties represent one or several (i.e. 2, 3, or more) suitable nucleotides, or phosphoramidites or other moieties that provide functional groups and/or cleavable covalent linkages, defined herein, for covalent coupling and is suitably coupled to provide the desired function for the example it is presented in.

And wherein said Zipper X moieties can also provide a suitable space, or bulge within said zipper structures that provide suitable steric hindrance or protection for said linkage from cleavage while said zipper is in a closed conformation, defined herein.

Subsequences or strands are designated as S1, S2, S3, S4, S5, and S6 and correspond to the edges of the tetrahedron and wherein "-A-" represents at least one nucleotide or suitable moiety that is found at each corner of said tetrahedron. And wherein said sequences are identified by the following color coding of said strands to indicate regions of complementarity, and are labeled at each 3' end with optional TMs.

Alternatively, each 5' end, instead of each 3' end of said strand is suitably coupled with said optional or interchangeable TMs and/or, a suitable combination of both is used.

```
S1:
                              (Seq ID No: 150)
      5'-GTCTGAGGCAGTTGAG-A-

(Seq ID No: 151)
      GATCTCGAACATTCC-X-(TM-A)_R 3'

S2:
                              (Seq ID No: 152)
      5'-TAAGTCTGAAGATCC-A-

(Seq ID No: 153)
      TTTATCACCAGCTGCTGCACGCCATAGTAG-A-

(Seq ID No: 154)
      CGTATCACCTGTCC-X-(TM-B)_R 3'

S3:
                              (Seq ID No: 155)
      5'-AGCTACTTGCTACACG-A-

(Seq ID No: 156)
      GGATCTTCAGACTTAGGAATGTTCGAGATC-A-

(Seq ID No: 157)
      CATGCGAGGACTCGGTCCAATACCGTACTA-A-

(Seq ID No: 158)
      CGATTACAGATCAA-X-(TM-C)_R 3'

S4:
                              (Seq ID No: 159)
      5'-CAGCTGGTGATAAA-A-

(Seq ID No: 160)
      CGTGTAGCAAGTAGCTTTGATCTGTAATCG-A-

(Seq ID No: 161)
      CTCTACGGGAAGAGC-X-(TM-D)_R 3'
```

-continued

S5:
(Seq ID No: 162)
5'-ATGCCCATCCGGCTC-A-

(Seq ID No: 163)
CTACTATGGCGTGCAG-X-(TM-E)$_R$ 3'

S6:
(Seq ID No: 164)
5'-CGAGTCCTCGCATG-A-

(Seq ID No: 165)
CTCAACTGCCTCAGACGGACAGGTGATACG-A-

(Seq ID No: 166)
GAGCCGGATGGGCATGCTCTTCCCGTAGAG-A-

(Seq ID No: 167)
CGGTATTGGACATGAT-X-(TM-F)$_R$ 3'

With suitable modifications known in the art, other suitable sequences and/or NA nanostructures and methods can be substituted to provide functional zipper motifs with CL-coupled drugs, targeting moieties, functional groups, extensions and any other moieties disclosed herein to provide a force-responsive nanostructure of this invention.

Other suitable nanostructures that can be modified for the purposes of this invention are disclosed by Abi, A., et al, ACS Appl. Mater. Interfaces 6, 8928-8931 (2014) for suitable tetrahedrons with aptamers incorporated into their "edges" that can contain CL-coupled drugs that can be released with a change in conformation.

Also, Dong, S., et al, ACS Appl. Mater. Interfaces 7, 8834-8842 (2015) for suitable nanostructures capable of virus detection with the following optional thiol groups and optional 5'-3' sequences of strands that can be suitably modified as needed:

S1:
(Seq ID No: 168)
CCCGCAGATGACTAATTTTTTTTTTACATTCCTAAGTCTGAAACATTACA

GCTTGCTACACGAGAAGAGCCGCCATAGTA

S2:
(Seq ID No: 169)
SH-C6-TATCACCAGGCAGTTGACAGTGTAGCAAGCTGTAATAGATGCGA

GGGTCCAATAC

S3:
(Seq ID No: 170)
SH-C6-TCAACTGCCTGGTGATAAAACGACACTACGTGGGAATCTACTAT

GGCGGCTCTTC

S4:
(Seq ID No: 171)
SH-C6-TTCAGACTTAGGAATGTGCTTCCCACGTAGTGTCGTTTGTATTG

GACCCTCGCAT

Also, Feng, Q-M., et al, Biosensors and Bioelectronics 90, 251-257 (2017) for tetrahedron nanostructures and synthesis methods that include thiol groups that are useful in this invention with suitable modification; Ge, Z., et al, Anal. Chem. 86, 2124-2130 (2014); Shiu, S. C-C., et al, Molecules 23, 1695 (2018) for useful aptamers for binding plasmodium sp., and useful methods to prepare NA tetrahedrons, squares, pentagon-based pyramids, and prisms that can be suitably modified for synthesizing force-responsive carriers of this invention and Wen, Y., et al, Anal. Chem. 83, 7418-7423 (2011).

And wherein it is applicable, sequences can be suitably modified and thiol functional groups can be used for coupling to any suitable moieties defined in this invention and wherein all references, including supporting information referenced in the disclosures of this invention are hereby incorporated herein by reference.

Conversion of Nanoparticle Compositions to a Device Coating Composition.

With suitable modifications as needed, any Nanoparticle Composition examples, including covalent or noncovalent coupling compositions provided herein, can also be used to prepare Device Coating Compositions, that can be applied to any suitable medical device including any medical implants, drug eluting implants, intubations, shunts, stents including drug eluting stents, catheters, including balloon catheters and any resorbable stents, catheters or other resorbable implants and devices.

Said Device Coating Composition will provide a drug releasing coating that is useful for controlled drug release from said devices and implants. Suitable active agents useful in said Device Coating Compositions include any antibiotics and/or drugs to prevent restenosis such as paclitaxel and other taxanes.

Suitable Targeting Moieties useful in said Device Coating Compositions include those that selectively bind to any suitable cells, including any in the immune system, involved in producing device rejection, wherein binding to said cells provide suitable Nanoforce™ to produce a conformational change and allow release of said drugs.

For instance, any said representative NanoParticle is substituted for any suitable surface (i.e. polymeric), of a medical device, implant device or catheter. The resulting composition or component coupled to said surface can then function as a modified Device Coating Component, modified for surface drug delivery. And, wherein the composition, substance or component with coupled active agent can function as a modified Active Agent Component.

Either component can be suitably modified or derivatized as needed, wherein any suitable block polymers, lipids or amino acid residues can be derivatized, substituted, added or subtracted in said compositions to provide the desired structure, properties, functional groups and/or binding affinities between said components.

Double Bar Symbol; ▬ represents any suitable coupling substance and/or coupling method that provides either covalent or noncovalent coupling of the indicated moiety to the intended device.

And, the substance or component with coupled active agent can function as the Active Agent Component (AA Component), defined herein. As defined herein, the symbol; "CL-DRUG" represents a composition comprising said CL, defined herein, and a biocleavably coupled active agent (CL-DRUG), defined herein, covalently coupled to a suitable nucleic acid or phosphoramidite, defined herein, in a suitable "stem" or "loop" or "bulge" section of the aptamer, defined herein.

The TM-Loop symbol, ⌿TM represents a nucleic acid sequence forming the "targeting moiety loop" or TM-loop region of said aptamer that also functions as a targeting moiety (TM), defined herein.

The nucleic acid sequence forming the TM-loop region of said aptamer can be any suitable sequence of nucleic acids, defined herein, designed to specifically bind with the desired target substance (i.e. biomarker). Said TM-loop region can also include any suitable secondary structure such as more than one hybridized stem region, additional loops and/or partial hybridizations and/or sections of noncomplimentarity of the nucleic acid strand that can produce "bulges" or "hairpin bulges" in said stem regions.

Alternatively, said TM-Loop is replaced with a suitable nonbinding LOOP that contains suitable nucleic acids (i.e. proline), to provide said structural loop or bulge without specific TM binding.

Alternatively, said nonbinding loop also contains any suitable functional group and/or phosphoramidite suitably derivatized to provide a functional group (i.e. sulfhydryl, amino or carboxyl), at a suitable location for covalently coupling to an active agent through a suitable cleavable linkage, defined herein.

When subjected to a suitable Nanomechanical™ force, the complementary nucleic acid strands will be pulled apart (unzipped), producing the open, single stranded (partially or fully), form of the nucleic acid flexible carrier, as defined herein. Said nucleic acid includes any suitable nucleic acid, as defined herein, including DNA, RNA, any suitable derivatized nucleic acid derivatives and PNAS, as defined herein.

Said zipper, or hairpin nucleic acid strand is oriented so that when hybridized to itself, the 5' end of the strand opposes or, is closest to, the 3' end of the strand.

Targeting Moieties.

In addition, said hairpin nucleic acid strand has one or more targeting moieties, (TMs), defined herein, independently and covalently coupled to it.

In one embodiment, the nucleic acid strand has one or more TMs, defined herein, covalently coupled to its corresponding 5' end (i.e. through suitable derivatization), and has one or more TMs, defined herein, covalently coupled to its corresponding 3' end (i.e. through suitable derivatization). In the open (not hybridized) configuration of the flexible carrier, said TMs of the strand are at opposite ends of the strand.

In the hybridized, closed configuration of the flexible carrier, said TMs at said 5' and 3' ends of the strand are at the same end of the self-hybridized hairpin duplex.

Alternatively, in another embodiment, the nucleic acid strand has one or more TMs, defined herein, covalently coupled to its corresponding 5' end or, covalently coupled at some other suitable point along the length of the nucleic acid strand between the 5' end and said centralized loop or hinge section (i.e. through suitable derivatization). In addition, the nucleic acid strand has one or more TMs, defined herein, covalently coupled to its corresponding 3' end or, covalently coupled at some other suitable point along the length of the nucleic acid strand between the 3' end and said centralized loop or hinge section (i.e. through suitable derivatization).

In addition, said cleavable linkage or bond between each active agent and said nucleic acid strand is only cleavable when said nucleic acid strand is not in a duplex (i.e. unzipped, open form), as defined herein. There is also the proviso that said cleavable linkage or bond between each active agent and nucleic acid strand cannot be cleaved when said nucleic acid strand is in a self-hybridized duplex (i.e. zipped, closed form), as defined herein.

Without imposing limitations on the scope of this invention, the mechanism for preventing cleavage of said cleavable linkages when the flexible carrier is in its closed form is through steric hindrance and/or physical or molecular obstruction that prevents cleavage of the linkage. Said steric interference is suitably caused by the design and/or nucleic acid sequences of the nucleic acid strands, as disclosed herein, that provide a suitable structure or shape when in said hybridized forms that interferes with cleavage of said cleavable linkages. Also, said steric interference can be suitably caused through the incorporation (i.e. added by suitable derivatization) of sterically interfering molecules, as disclosed herein, into the nucleic acid strand, resulting in suitable steric interference of said linkages when said strand is in said hairpin form.

However, when the hairpin flexible carrier in its closed form is subjected to a suitable Nanoforce™, as defined herein, the complementary nucleic acid sections will be pulled apart (unzipped), producing the single stranded, open form of the flexible carrier, as defined herein. Consequently, said cleavable linkage between covalently coupled active agent and intercalator will be exposed to chemical or biochemical (i.e. enzymes) in the environment that are capable of cleaving the linkage. Subsequently, the linkage will be cleaved and the active agent will be released after or during said unzipping of said nucleic acid zipper.

Polypeptide Aptamer Synthesis.

Peptide aptamers for this invention can be suitably synthesized by manual N-tertbutyloxycarbonyl (t-Boc) chemistry as disclosed by Schnolzer, M.; et al, Int. J. Pept. Protein Res. 40, 180-193 (1992) and references that are incorporated herein.

For t-Boc chemistry, standard in situ neutralization protocols are employed, with hydroxybenzatriazole tetramethyluronium hexafluorophosphate (HBTU, Novabiochem, San Diego, CA) as coupling reagent. Peptides can also be suitably synthesized by automated 9-fluorenylmethoxy-carbonyl (Fmoc) chemistry.

For instance, Fmoc synthesis can be done using commercially available instrumentation such as an Advanced ChemTech 348 Omega synthesizer (AACEP, Louisville, KY) using diisopropylcarbodiimide and hydroxybenzatriazole as coupling activation reagents and following manufacturer's protocols.

Protected amino acids and peptide synthesis reagents are available from Advanced ChemTech (Louisville, KY) and Novabiochem. The cleaved, polypeptide products are suitably purified by RP-HPLC using linear gradients of water and acetonitrile (0.1% TFA)

Coupling Active Agent to the Peptide Aptamers.

In preferred embodiments, the mostly centrally located residue position in one or more of the segments or sequences is meant to designate the amino acid residue C (cysteine or Cys), to provide a free thiol under suitable conditions for covalent coupling with an active agent. The position in the opposite sequence can be filled with a suitable lipophilic residue such as L or I, among others. Alternatively, a suitable "bulge" or "stem loop" is incorporated in either sequence to allow space for coupling of said active agent. Coupling of an active agent (or drug) to the polypeptide is suitably through a dithiol (S—S) linkage, or through a suitable cleavable amino acid sequence, defined herein.

Coupling Antibody to the Polypeptide.

At or near the N terminal position of each peptide segment is a K (lysine) residue designed to allow covalent coupling to a suitable antibody (Ab). For example, antibody1 (or Ab1) and antibody2 (or Ab2) can be specific for the same antigen or different antigens. The coupling can include any suitable covalent linkage known in the art for coupling peptides or amino acids through an amino functional group to the aptamer. For example, the methods disclosed by Kida, et al, (Chem. Pharm. Bull. 55 (4) 685-687 (2007)) using a heterobifunctional crosslinking agent can be used.

The crosslinking reagents, 6-maleimidohexanoic acid N-hydroxysuccinimide ester (MHSu) and 6-maleimido-hexanoic acid 4-nitrophenyl ester (MHNp), are heterobi-functional reagents for cross-linking between amino and sulfhydryl groups.

The cross-linker is suitably coupled initially through the activated ester moiety to the primary amine of lysine of the polypeptide segment to produce an amide bond. Then it is coupled through the maleimide moiety to the sulfhydryl group on the aptamer to produce a thioether linkage. The sulfhydryl group on the aptamer can be made available by dithiol reduction of suitable thiols on the aptamer fragment. Or it can be introduced by thiolation of the aptamer by well-known derivatization methods.

Synthesis Example Methods

In the examples herein, percentages are by weight unless indicated otherwise. During the synthesis of the composi-tions of the instant invention, it will be understood by those skilled in the art of organic synthesis, that there are certain limitations and conditions as to what compositions will comprise a polymer flexible carrier suitable for pharmaceu-tical use and may therefore be prepared mutatis mutandis. It will also be understood in the art of active agents, aptamers, antibodies, polypeptides and nucleic acids that there are limitations as to which derivatives and/or coupling agents can be used to fulfill their intended function.

The terms "suitable", "suitably modified" and "appropri-ate" refer to derivatization and/or synthesis methods known to those skilled in the art for performing the described reaction, or synthesis and/or other procedures needed to provide the intended composition and/or result of this inven-tion. In the references to follow, the methods are hereby incorporated herein by reference. For example, organic synthesis reactions, including cited references therein, that are useful in the instant invention are described in "The Merck Index", 9, pages ONR-1 to ONR-98, Merck & Co., Rahway, NJ (1976), and suitable protective methods are described by T. W. Greene, "Protective Groups in Organic Synthesis", Wiley-Interscience, NY (1981), among others. For synthesis of NA probes, sequencing and hybridization methods, see "Molecular Cloning", 2nd edition, T. Maniatis, et al, Eds., Cold Spring Harbor Lab., Cold Spring Harbor, NY (1989).

All reagents and substances listed, unless noted otherwise, are commercially available from Applied Biosystems Div., Perkin-Elmer; Aldrich Chem. Co., WI 53233; Sigma Chem. Co., Mo. 63178; Pierce Chem. Co., IL. 61105; Eastman Kodak Co., Rochester, NY; Pharmatec Inc., Alachua FL 32615; and Research Organics, Cleveland, OH. Or, sub-stances are available or can be synthesized through refer-enced methods, including "The Merck Index", 9, Merck & Co., Rahway, NJ (1976). Additional references cited in U.S. Pat. No. 6,048,736 and PCT/US99/30820, are hereby incor-porated herein by reference.

Nucleic Acid Flexible Carrier Synthesis for This Invention.

The general synthesis approach is; (1) produce or modify or protect, as needed, one or more functional groups on a nucleic acid strand, and; (2) using one or more coupling methods, couple an active agent or TM to a nucleic acid directly or through a coupling agent suitable for pharma-ceutical use.

Also, as described below, the flexible carrier may be suitably derivatized to include other useful substances and/ or chemical groups (e.g. targeting molecules), to perform a particular function. Depending on the requirements for chemical synthesis, the derivatization are done before cou-pling the active agent, or afterward, using suitable protection and deprotection methods as needed.

The flexible carrier substance is suitably derivatized and coupled through well-known procedures used for available amino, sulfhydryl, hydroxyl, or vinyl groups. Also, for certain carbohydrates added to the flexible carrier substance, vicinal hydroxyl groups can be appropriately oxidized to produce aldehydes. Any functional group can be suitably added through well-known methods while preserving the flexible carrier substance structure and properties. Examples are: amination, esterification, acylation, N-alkylation, ally-lation, ethynylation, oxidation, halogenation, hydrolysis, reactions with anhydrides, or hydrazines and other amines, including the formation of acetals, aldehydes, amides, imi-des, carbonyls, esters, isopropylidenes, nitrenes, osazones, oximes, propargyls, sulfonates, sulfonyls, sulfonamides, nitrates, carbonates, metal salts, hydrazones, glycosones, mercaptals, and suitable combinations of these. The func-tional groups are then available for suitable coupling or cross-linking using a bifunctional reagent.

Suitable coupling or cross-linking agents for preparing the flexible carriers of the instant invention are a variety of coupling reagents, including oxiranes (epoxides) previously described. Also useful are methods employing acrylic esters such as m-nitrophenyl acrylates, and hexamethylene diamine and p-xylylene-diamine complexes, and aldehydes, ketones, alkyl halides, acyl halides, silicon halides and isothiocyanates.

Synthesis methods that are suitably modified for prepar-ing the compositions of this invention are disclosed in the art, including Kanlidere, Z., et al, Beilstein J. Org. Chem. 12, 2136-2144 (2016); Paris, C. et al, Molecules 2015, 20, 6389-6408; Sanchez, A., et al, Org. Biomol. Chem., 10, 8478 (20120; and Wang, R., et al, Chem. Sci., 7, 2157 (2016), which are incorporated herein, including references therein.

Synthesis of Nucleic Acids with Suitable Functional Groups.

Because conventional automated synthesis of nucleic acids proceeds from 3' to 5', the 5'-terminus is readily available for the addition of functional groups. A general approach to the modification of the 5'-terminus is to use reagents which couple to the 5'-hydroxyl of an oligonucle-otide. In this invention, the phosphoramidite reagents used include active agent phosphoramidites as described herein, and those that are compatible with automated DNA synthe-sizers. Many of these reagents are available from Glen Research Corp., Sterling, VA, and other suppliers.

5'-Modified and Centrally Modified Nucleic Acids.

A preferred group of phosphoramidite reagents is the 5'-Amino-Modifiers. The 5'-Amino-Modifiers are preferably for use in automated synthesizers to functionalize the 5'-ter-minus of a target oligonucleotide. With suitable changes in the methods, said 5'-Amino-Modifiers can also be used in automated synthesizers to incorporate one or more centrally located functional amino groups for coupling suitable active agents. The primary amine is used to attach a variety of functional moieties to the oligonucleotide.

The 5'-Amino-Modifiers include 6-(4-Monomethoxytri-tylamino) hexyl-(2-cyanoethyl)-(N,N-diisopropyl)-phos-phoramidite, M.W.: 589.76; 12-(4-Monomethoxytrity-lamino) dodecyl-(2-cyanoethyl)-(N,N-diisopropyl)-phosphoramidite, M.W.: 673.92 and 2-[2-(4-Monomethoxytrityl) aminoethoxy]ethyl-(2-cyanoethyl)-(N, N-diisopropyl)-phosphoramidite, M.W.: 577.71.

Also included are 6-(Trifluoroacetylamino) propyl-(2-cyanoethyl)-(N,Ndiisopropyl)-phosphoramidite, M.W.:

371.34 and 6-(Trifluoroacetylamino) hexyl-(2-cyanoethyl)-(N,N-diisopropyl)-phosphoramidite.

Another group of preferred reagents for adding an amino group are 5'-amino-modifiers such as β-cyanoethyl (CE) phosphoramidites which, when activated with 1H-tetrazole, can couple to the 5'-terminus of the nucleic acid with similar efficiency as nucleoside phosphoramidites.

5'-Thiol Nucleic Acid.

The phosphorothioate nucleic acids are synthesized using beta-cyanoethyl phosphoramidite chemistry. Acetylation is performed by 0.1 M acetic anhydride/tetrahydrofuran (THF) and 0.1 M imidazole/THF. Sulfurization is done using EDITH reagent.

The commercially available six-carbon thiol linker phosphoramidite (1-O-dimethoxytrityl-hexyl-disulfide-1'-[(2-cyanoethyl)-(N,N-diisopropyl)]-phosphoramidite (Glen Research) is coupled to the 5' end. With suitable changes in the methods, said thiol phosphoramidites can also be used in automated synthesizers to incorporate one or more centrally located functional sulfhydryl groups for coupling suitable active agents. The nucleic acid is suitably recovered and purified and used for conjugation to any active agents or to the active agent-coupled flexible carriers, described herein.

Another preferred phosphoramidite reagent for adding a thiol functional group includes (S-Trityl-6-mercaptohexyl)-(2-cyanoethyl)-(N,N-diisopropyl)-Phosphoramidite, which produces a thiol group at the 5'-terminus (or centrally, as needed), of a synthetic oligonucleotide or nucleic acid. Alternatively, coupling to the 3'-terminus, it is added to any suitable support and then the desired nucleic acid is synthesized. DTT is used during deprotection or after purification of the product nucleic acid to cleave the disulfide linkage.

A. Kumar, et al, in Nucleic Acids Res., 19, 4561 (1991) describes a procedure useful to modify a 5'-amino-modified oligonucleotide to a thiol using N-acetyl-DL-homocystein thiolactone. Another preferred group is those designed to introduce a thiol group to the 3'-terminus (or centrally as needed), of a target oligonucleotide such as 1-O-Dimethoxytrityl-propyl-disulfide, 1'-succinoyl-long chain alkylamino-CPG.

Another preferred group of phosphoramidite reagents in this invention includes spacer phosphoramidites such as 9-O-Dimethoxytrityl-triethyleneglycol, 1-[(2-cyanoethyl)-(N,N-diisopropyl)]-phosphoramidite, 18-O-Dimethoxytrityl-hexaethyleneglycol, 1-[(2-cyanoethyl)-(N,N-diisopropyl)]-phosphoramidite, 3-O-Dimethoxytrityl-propyl-1-[(2-cyanoethyl)-(N,Ndiisopropyl)]-Phosphoramidite, 12-O-Dimethoxytrityl-dodecyl-1-[(2-cyanoethyl)-(N,Ndiisopropyl)]-phosphoramidite and 5'-O-Dimethoxytrityl-1',2'-Dideoxyribose-3'-[(2-cyanoethyl)-(N,N-diisopropyl)]-phosphoramidite.

In this invention, spacer phosphoramidites can be used to insert a mixed polarity 3 to 18 atom spacer arm in a nucleic acid. These compounds may be added in multiple additions if a longer spacer is required, such as in said loop sections of said hairpin nucleic acid zippers. The spacer phosphoramidites can also be added to substitute for bases within a nucleic acid and to mimic an abasic site in an oligonucleotide.

Colored or Fluorescent Labeling.

Another preferred group of phosphoramidite reagents useful in this invention is any suitable colored or fluorescent labeling moiety. This includes any suitable 3' or 5'-labelling reagent. Fluorescent derivatives are useful in tracking nucleic acids and/or the flexible carrier in vivo or in vitro. Included are any fluorescein derivatives (i.e. 6-FAM, HEX and TET, derived from the 6-carboxy fluorescein isomer).

Also included are any cyanine dye derivatives (i.e. Cy3 and Cy5 phosphoramidites) and phosphoramidite reagents with dabcyl or TAMRA labels.

Another preferred group of phosphoramidite reagents for this invention are any suitable 3' or 5'-Biotin (or D-desthiobiotin) phosphoramidite reagents, for adding biotin to the nucleic acid to provide a specific ligand for any suitable avidin, NeutrAvidin or streptavidin, or, to provide a suitable bulky moiety, defined herein. Biotin labeling phosphoramidites can be branched to allow multiple biotins to be introduced at the 3'- or 5'-terminus while biotin-dT can replace dT residues within the oligonucleotide sequence.

3'-Modified and Centrally Modified Nucleic Acids.

In the design and synthesis of antisense nucleic acids in this invention, there are preferred reagents for use in modifying the 3'-terminus of oligonucleotides. This may be achieved by modifying the 3'-terminus with a phosphate group, a phosphate ester, or using an inverted 3'-3' linkage. Nucleic acids modified at the 3'-terminus resist 3'-exonuclease digestion and thereby provide a more effective agent in vivo. With suitable changes in the methods, said 3'-Modifiers can also be used in automated synthesizers to incorporate one or more centrally located functional groups for coupling suitable active agents.

A preferred group of phosphoramidite chemical reagents for 3' phosphorylation (or centrally as needed), includes 2-[2-(4,4'-Dimethoxytrityloxy)ethylsulfonyl] ethyl-(2-cyanoethyl)-(N,N-diisopropyl)-phosphoramidite, among others.

A preferred simpler process is to couple any suitable phosphoramidite reagent that is desired for modifying the 3' end of a nucleic acid onto the support such as controlled pore glass (CPG). The coupled phosphoramidite is used as the starting compound for synthesizing the nucleic acid. Said coupling is designed for subsequent cleavage using suitable chemical methods to provide the desired 3' modification.

A preferred method is described by H. Urata, et al, Tetrahedron Lett., 34, 4015-4018 (1993) for the preparation of oligonucleotides with a 3'-phosphoglyceryl terminus, or, with suitable modification a centrally located phosphoglyceryl can be added for coupling to an active agent. The terminus (or centrally located phosphoglyceryl), is readily oxidized by sodium periodate to form a 3'-phosphoglycaldehyde. The aldehyde may be further oxidized to the corresponding carboxylic acid. Either the aldehyde or the carboxylate may be used for subsequent conjugation to amine-containing active agents, and other moieties.

Another preferred embodiment in synthesizing the compositions of this invention is to couple sense or antisense nucleic acids through the 3'-terminus. One preferred approach to 3' or central base modification is to prepare said nucleic acid with a ribonucleoside (RNA) terminus, or central RNA (i.e. nucleic acid chimera) using an RNA support, or other modifications. Subsequent oxidation of the 2',3'-diol cleaves the 2'-3' bond and generates reactive aldehyde groups. The resulting 3' or centrally located aldehyde group is then available for coupling to suitable linkers and functional groups on the active agents of this invention. The nucleic acid methods and references disclosed in U.S. patent application Ser. No. 10/923,112 are hereby incorporated into this invention.

Synthesis Materials.

All chemicals are reagent grade or purer, include deionized water, and available from well-known suitable suppliers. Some reagents used and their abbreviations are; benzotriazol-1-yloxy-tris (dimethylamino)-phosphonium hexafluorophosphate (BOP), 1-Decene, n-butylamine, 2,2, 2-trifluoroethanol, dicyclohexyl carbodiimide (DCC), 1,3-diisopropyl carbodiimide (DIC), N-(3-dimethylaminopropyl)-N'-ethylcarbo-diimide (EDC), ethylenediamine tetraacetic acid (EDTA), 3-nitrophenol, fluorescein isothiocyanate (FITC), fluorenyl methoxycarbonyl (Fmoc), N-hydroxysuccinimide (NHS), ethanethiol, n-butylamine, 4-(dimethylamino)-pyridine (DMAP), dithiothreitol (DTT), 1,1, 2-trichloroethane (TCE), trifluoroacetic acid (TFA), trityl (Trt) and sodium dodecyl sulfate (SDS). Some suitable solvents are; ethyl acetate (EtOAc), methanol (MetOH), tetrahydrofuran (THF), N,N-dimethyl formamide (DMF), dimethyl sulfoxide (DMSO), isopropanol and n-heptane. Phosphate-buffered saline (PBS) is 0.01 M sodium phosphate and 0.015 M sodium chloride, pH 7.2 or adjusted with 0.1 M HCl, 0.1 M KOH (or NaOH) solution as needed. Testing Procedures.

The active agents and derivatives in the preparations is determined by absorbance or by fluorescence using the appropriate excitation wavelength and reading at the appropriate emission wavelength. The sample concentration is determined by using least squares (linear regression) calculation of the slope and intercept from a standard curve of known concentrations.

Synthesis of Activated Ester Active Agents and Carrier Substances.

With suitable modifications as needed, the following are methods for synthesizing the compositions of this invention, disclosed in the Formulas and Examples herein. Some methods are based on J. T. C. Wojtyk, et al, in Langmuir 18, 6081 (2002), for derivatizing a carboxylate group on any suitable flexible carrier substance to provide an activated ester for coupling to a primary amine on an active agent, nucleic acid, intercalator or any suitable moiety.

In other preferred embodiments, these methods are used under suitable conditions for derivatizing a carboxylate group on any suitable active agent (AA), or NCS, disclosed herein, to provide an activated ester for coupling to a primary amine on any suitable amine-containing substance including flexible carrier substances, targeting moieties, or AA, as defined herein. For instance, with suitable modifications antibiotics are coupled to an active agent using the methods disclosed by B. G. Knecht, et al, in Anal. Chem. 76, 646-654 (2004), and references therein.

If needed, a flexible carrier substance, or an AA with a hydroxyl or amino group such as protein, dextran, cyclodextrin or PEG is first derivatized to provide a carboxylated flexible carrier substance or AA, by reacting it with acetic (or succinic) anhydride in anhydrous solvent such as DMF. If desired, any suitable carbodiimide can be substituted for DIC such as DCC or EDC.

A. Synthesis of 3-Nitrophenyl Activated Active Agents, or NCS, and Carrier Substances.

A1. 3-Nitrophenyl Activated Carrier. In a 100 mL round-bottom flask equipped with a magnetic stirrer and a nitrogen inlet is placed the carboxylated flexible carrier substance such as any suitable nucleic acid strand, or polypeptide sequence or flexible polymer with about 15 acid groups (1.00 g, 0.75 mmole acid) and 3-nitrophenol (0.14 g, 1.0 mmole). The mixture is dissolved in 10 mL of dry THF and cooled to 0° C. before a 10 mL THF solution of DIC (0.13 g, 1.0 mmole) and DMAP (0.012 g, 0.10 mmole) is added drop wise via a syringe over a 10 min period. The mixture is allowed to warm gradually to room temperature and stirred at this temperature for 18 h. The urea byproduct is filtered and the filtrate is precipitated from isopropanol to recover the product.

A2. 3-Nitrophenyl Activated Active Agent, or NCS. In a suitable flask, about 0.10 mmole acid equivalents of the carboxylated active agent (i.e. active agent succinate) or carboxylated AA is combined with about 1.0 mmole of 3-nitrophenol in suitable dry solvent such as THF or DMF, cooled to 0° C. Then about 10 mL of solvent containing 1.0 mmole of DIC is added drop wise. The mixture is stirred 18 hours at rt. The urea byproduct is filtered off and the activated ester (i.e. active agent ONp) is recovered by precipitation from the filtrate, or isolated by chromatography.

B. Synthesis of N-Hydroxy Succinimidyl (NHS) Activated Active Agents, or NCS, and Carriers.

B1. NHS Activated Carrier. In a 100 mL round-bottom flask equipped with a magnetic stirrer and a nitrogen inlet is placed the carboxylated flexible carrier substance such as any suitable nucleic acid strand, or polypeptide sequence or flexible polymer with about 15 acid groups (1.00 g, 0.75 mmole acid) and N-hydroxysuccinimide (NHS, 0.12 g, 1.00 mmole). The mixture is dissolved in 5 mL of dry DMF and cooled to 0° C. before a 5 mL DMF solution of DIC (0.13 g, 1.0 mmole) and DMAP (0.012 g, 0.10 mmole) is added drop wise via a syringe over a 10 min period. The mixture is allowed to warm to room temperature and stirred for 18 h at this temperature. The urea byproduct is filtered off and the filtrate is precipitated from isopropanol to recover the product.

B2. NHS Activated Active Agent, or NCS. In a suitable flask, about 0.10 mmole acid equivalents of the carboxylated active agent (i.e. active agent succinate) or carboxylated AA is combined with about 1.0 mmole of N-hydroxysuccinimide (NHS) in suitable dry solvent such as THE or DMF, cooled to 0° C. Then about 10 mL of solvent containing 1.0 mmole of DIC is added drop wise. The mixture is stirred 18 hours at rt. The urea byproduct is filtered off and the activated ester (i.e. active agent NHS) is recovered by precipitation from the filtrate, or isolated by chromatography.

C. Synthesis of S-Ethyl Activated Active Agents, or NCS, and Carrier Substances.

C1. S-Ethyl Activated Carrier. In a 100 mL round-bottom flask equipped with a magnetic stirrer and a nitrogen inlet is placed the carboxylated flexible carrier substance such as any suitable nucleic acid strand, or polypeptide sequence or flexible polymer with about 15 acid groups (1.00 g, 0.75 mmole acid) and ethanethiol (0.06 g, 1.00 mmole). The mixture is dissolved in 10 mL of dry THF and cooled to 0° C. before a 10 mL THF solution of DIC (0.13 g, 1.0 mmole) and DMAP (0.012 g, 0.10 mmole) is added drop wise via a syringe over a 10 min period. The mixture is stirred for 18 h at 0° C. The urea byproduct is filtered off and the filtrate is precipitated from isopropanol to recover the product.

C2. S-Ethyl Activated Active Agent, or NCS. In a suitable flask, about 0.10 mmole acid equivalents of the carboxylated active agent (i.e. active agent succinate) or carboxylated AA is combined with about 1.0 mmole of ethanethiol in suitable dry solvent such as THF or DMF, cooled to 0° C. Then about 10 mL of solvent containing 1.0 mmole of DIC is added drop wise. The mixture is stirred 18 hours at rt. The urea byproduct is filtered off and the activated ester (i.e. active agent S-ethyl ester) is recovered by precipitation from the filtrate, or isolated by chromatography.

D. Activated Ester Intercalator or Other Moiety.

With suitable modifications, the procedures used to add activated esters to the carboxylated flexible carrier substances described previously, can also be used to add activated esters to carboxylated substances. If needed, an active agent, intercalator or targeting moiety with a hydroxyl or amino group is first carboxylated by reacting it with acetic anhydride in anhydrous solvent such as DMF. These carboxylated substances are then coupled to amino-derivatized flexible carrier substances using carbodiimide.

E. Activated Paclitaxel or Methotrexate Ester.

In this example, methotrexate (MTX), or paclitaxel succinate is activated based on known methods such as from K Riebeseel, et al, Bioconj. Chem. 13, 773-785 (2002), including references therein, for subsequent coupling to any suitable flexible carrier substance that can include other active agents.

To a suitable solution of the carboxylated AA such as paclitaxel succinate and N-hydroxysuccinimide (NHS) dissolved in about 0.25 mL of dry DMF, cooled to 0° C., is added drop wise, a suitable, ice cold solution of DCC in about 0.1 mL DMF with stirring. The mixture is allowed to warm to room temperature and stirred for 18 h at this temperature. The urea byproduct is filtered off and the filtrate is precipitated from solvent (i.e. isopropanol) to recover the NHS-ester AA product. The NHS-ester AA is then coupled by suitable mixing with an amine-containing, cleavable linkage, or CLL, or intermediate substance, defined herein, that can include any suitable flexible carrier substance, aptamer, or coating composition defined herein.

Said flexible carrier substance (i.e. aptamer, amino-PEG, protamine, antibody) can also have other moieties including active agents (i.e. primaquine, HQ-amine, mefloquine amine), coupled thereto.

In another example, the NHS-ester-CCA is coupled to any suitable AA (i.e. NRTI, SQV, quinacrine amine) that has an available coupling group. Alternatively, MTX can be converted to a cyclic anhydride by omitting the NHS in the above procedure in cold DMF. The MTX anhydride is then mixed with a hydroxylated or amine-containing active agent for coupling.

F. Coupling an Activated Moiety to Amino-Containing Cleavable Linkages on Carrier Substances.

With suitable modifications as needed, this procedure is used to conjugate a suitable amino-containing cleavable linkage on a suitable flexible carrier substance (i.e. any suitable aptamer, peptide, protein, antibody, HSA, amino-PEG or amino-dextran) with any suitable activated ester moiety including, active agents, and targeting moieties that have active ester (i.e. NHS) or isothiocyanate functional groups.

At pH 9, conjugation occurs virtually exclusively at the amino group. About 0.2 mmoles of amino-containing flexible carrier substance (i.e., with about 0.1-0.2 mmoles of free primary amines) is dissolved in 1-2 mL of sterile distilled water. To this flexible carrier solution is added 0.1-0.2 mL of 10× conjugation buffer (1M $NaHCO_3$/$Na_2CO_3$, pH 9). A 10 mg/mL DMF solution is freshly prepared of the activated active agent or other moiety containing active ester or isothiocyanate. To the buffered flexible carrier solution is added 0.2-0.4 mL of the DMF solution, mixed and allowed to stand at least 2 hours or overnight. The reaction mixture is desalted on a column of Sephadex G-25 in water and the product is purified using reverse phase HPLC if necessary.

Alternatively, with suitable modification, the methods disclosed by Caculitan, N G, et al, Cancer Res; 77, 1-11 (2017), for preparing Cathepsin-Cleavable linkages, defined herein, can be used in this invention to prepare suitable active agents coupled to suitable thiol groups (i.e. using maleimidocaproyl), available on said carrier aptamers and nanostructures, defined herein. Preferred embodiments include the use of any protease-cleavable linkages, including valine-citrulline (VC(S)) linkers, among others, to conjugate suitable active agents including monomethyl auristatin E (MMAE), monomethyl auristatin F (MMAF), calicheamicin and pyrrolo[2,1-c][1,4]benzodiazepine dimer (PBD), among others.

Preferred embodiments of this invention also include the use of suitably modified synthesis methods of Kratschmer, C., et al, Mol. Ther: Nucleic Acids 10, 227 (2018), Alley, S. C., et al, Bioconj. Chem. 19, 759-765 (2008), and Doronina, S. O., et al, Bioconj. Chem. 19, 1960-1963 (2008), including any Supplemental Information, and references therein, which are incorporated herein.

They disclose several useful methods for conjugating drugs to the flexible carriers of this invention, including thiol-reactive variants of monomethyl auristatin E (MMAE) and monomethyl auristatin F (MMAF) using a cathepsin-cleavable valine-citrulline linker (MC-VC-PAB-) to a cleavable linker, valine-citrulline, and the self-immolative spacer, p-amino-benzyloxy carbonyl (PABC).

Preferred embodiments of this invention can also include the use of anti-transferrin receptor aptamer, Waz, and an anti-epidermal growth factor receptor aptamer, E07, maytansine and auristatin derivatives, and emtansine, a maytansine derivative, which work by inhibiting microtubule assembly.

Though MMAF is less toxic than MMAE, its inability to cross the lipid bilayer into other cells, coupled with its higher aqueous solubility, should result in an improved therapeutic index in vitro if endosomal escape can be facilitated by a cleavable linker.

MMAE and MMAF are now commercially available with a variety of linkers: non-cleavable MMAE and cleavable MMAF, as well as substitutions for the valine-citrulline linkage to other dipeptide linkages and substitutions for the maleimidocaproyl moiety to a bromoacetamidecaproyl moiety can be used. Amination Methods Including Tosylation.

Flexible carrier substances, targeting moieties and active agents that do not normally contain amino groups are suitably aminated to provide them by methods well known in the art as is disclosed for CD derivatives by A. R. Khan, et al, in Chem. Rev. 98, 1977-1996 (1998) and references therein which are hereby incorporated. With suitable modifications as needed, flexible carrier substances including aptamers and nanostructures with suitable hydroxyl groups and/or carbohydrates including inulins, dextrans and cyclo-dextrins, as well as PEG and other hydroxlated polymers with suitable hydroxyl groups are readily aminated through tosylation. The hydroxyl groups are first reacted with p-toluene sulfonyl chloride, in suitable anhydrous solvent. Then the tosylate on the reactive site is displaced by treatment with excess sodium azide. Finally, the azide is reduced to an amine with an appropriate hydrogenation method such as with hydrogen and a noble metal catalyst to provide an amino-containing flexible carrier substance.

Thiolation And Coupling Methods.

In preferred embodiments of this invention, suitable hydrazine or other amino groups on amino-containing flexible carrier substances, aptamers, nanostructures, active agents, NCS, intercalators and targeting moieties, are suitably thiolated, as needed, to provide thiols for disulfide or maleimide coupling. Said coupling is between any suitable flexible carrier substance, defined herein, and any active agent, NCS, or intercalator, defined herein. Succinimidyl 3-[2-pyridyldithio] propionate (SPDP) is a short-length crosslinker for amine to sulfhydryl (thiol) conjugation via its NHS-ester and Pyridyl dithiol reactive group that incorporates a cleavable disulfide bond. Suitable methods using SPDP or 2-iminothiolane are disclosed by E. J. Wawrzynczak, et al, in C. W. Vogel (ed.) "Immunoconjugates; Antibody Conjugates in Radioimaging and Therapy of Cancer." NY; Oxford Univ. Press, pp 28-55, (1987).

With suitable modifications as needed, primary amino groups on an active agent or NCS, or flexible carrier substance are thiolated in PBS, pH 7.5 by adding a 2x molar excess of SPDP in EtOH and letting it react for about 1 hour at rt. Said active agent or NCS is now provided with a pyridyldithiol reactive group for coupling to any suitable sulfhydryl-containing moiety. Excess SPDP can be removed by size exclusion gel chromatography. Alternatively, said pyridyldithiol is reduced with tris (2-carboxyethyl) phosphine (TCEP) or DTT to provide a sulfhydryl group on said active agent or NCS.

Preferred thiol coupling in this invention includes suitable disulfide coupling or the use of maleimide linkers that include, but are not limited to, those disclosed by EJF Prodhomme in; Bioconj. Chem., 14, No. 6, (2003) and Kuan, S L, et al, Chem. Eur. J. 22, 17112-17129 (2016).

Thiol-Disulfide Interchange. With suitable modifications as needed, this is a method useful in this invention for disulfide coupling of two thiolated moieties through their sulfhydryl groups to produce a disulfide linkage. For example, a thiolated flexible carrier substance, antibody, or active agent is first activated by reacting the sulfhydryls with a slight molar excess of 2, 2'-dipyridyl disulfide (2DD), in suitable buffer (i.e. 0.1 M NaHCO$_3$, pH 8), for about 30 minutes. Depending on the type of substance, the excess 2DD is removed by precipitation or gel exclusion chromatography. The 2DD-activated flexible carrier substance, antibody, or active agent, or NCS, is then combined with any suitable thiolated moiety in pH 8 buffer and reacted for 12-24 hours. The substance with disulfide coupled moiety is suitably collected by precipitation or chromatography.

Cleavable Disulfide Linkage Active Agents (AA-DTSP) and NCS-DTSP.

With suitable modifications as needed, any suitable amino-containing active agent (amino-AA), defined herein, is derivatized with a bifunctional, amino cross linker 3, 3'-dithio-bis (propionate N-hydroxy succinimide ester), (DTSP, Sigma-Aldrich), which also contains a cleavable, disulfide linkage. In these examples, the DTSP is used to cross link said amino-AA, to any suitable amino-containing flexible carrier to produce a new composition.

With suitable modifications as needed, any suitable amino-containing Noncovalent Coupling Substance (NCS), defined as an "amino-NCS", can be substituted for said amino-AA in these reactions. Any suitable amino-NCS, includes any suitable amino-containing intercalators, defined herein.

To a solution of about 1 mmole of amino-AA, or amino-NCS, in 10-20 mL of suitable solvent (i.e. 60% DMF and 12% DMSO in water), is added about 0.35 gm (0.9 mmoles) of DTSP in 6 mL of about 16% CH$_2$Cl$_2$ in DMF and reacted in the dark at rt for about 3 hours. When using amino-AA, the resulting coupled product, active agent-DTSP, (AA-DTSP) conjugate is suitably purified by precipitation and/or by gel exclusion chromatography (i.e. Sephadex™ G15) and the product fractions collected, pooled and concentrated by evaporation and/or dialysis.

When using amino-NCS, the resulting coupled product, designated NCS-DTSP conjugate, is suitably purified by precipitation and/or by gel exclusion chromatography, product fractions collected, pooled and concentrated by evaporation and/or dialysis. Said NCS-DTSP is used to prepare cleavable conjugates with any suitable amino-AA, defined herein, to provide an AA-NCS conjugate, defined herein.

Either DTSP conjugated product is stored in suitable solvent (i.e. DMSO). Said AA-DTSP is used to prepare cleavable conjugates with any suitable flexible carrier, defined herein. Any suitable amino-containing active agent (amino-AA), defined herein, includes, but is not limited to, primaquine (PQ), dapsone, pyrimethamine, penicillamine, and any suitable active agents disclosed or referenced herein.

Alternatively, and if suitable, a thiolated active agent or a thiolated NCS can be prepared by suitable reduction of said AA-DTSP or said NCS-DTSP with dithiothreitol (DTT), or dithiobutylamine (DTBA), or tris (2-carboxyethyl) phosphine (TCEP), to provide a sulfhydryl group on said AA or said NCS, respectively. Alternatively, the amino group on said amino-AA is thiolated using 2-iminothiolane to provide thiolated active agent for disulfide coupling to any suitable thiolated flexible carrier substance.

Cleavable Disulfide Linkage Between Active Agent and Carrier Nucleic Acid or Carrier Aptamer.

In another preferred embodiment, said AA-DTSP is coupled to any suitable amino-derivatized carrier aptamer, or carrier nucleic acid, or carrier nucleic acid zipper, or nucleic acid aptamer, or peptide aptamer, defined herein, with an available amino group. For instance, any suitable nucleic acid strand containing an available amino functional group (i.e. phosphoramidite, amino-ODN, or amino-RNA), is suitably combined with a solution of said AA-DTSP to produce said AA-DTSP-nucleic acid. Preferably, said amino group is at or near the central area of said nucleic acid strand so that when a second, complementary nucleic acid strand is added (or said single strand is suitably folded), to form said double-stranded zipper, defined herein, said disulfide bond is suitably protected from cleavage while said zipper is in its closed form, defined herein.

The resulting said AA-nucleic acid then contains a cleavable disulfide linkage between the said AA and said carrier nucleic acid. Also, by incorporating multiple amino groups into said nucleic acid, several said AA moieties are coupled to said carrier nucleic acid.

To about 0.2 mg of suitable aptamer, defined herein, in about 0.5-2.0 mL of 0.002 M NaCO$_3$, pH 8, is added about 1-3 ml of said AA-DTSP solution (about 0.25 mmoles), mixed and left at rt in the dark for 12-48 hours. The resulting product, said AA-DTSP-aptamer conjugate is purified by Sephadex™ G15 gel exclusion chromatography and the leading fractions collected, pooled and concentrated. Amino-AA conc. is determined by suitable absorbance or fluorescence vs. protein conc. by a suitable amino assay.

Also, in preferred embodiments, other amino-containing proteins or peptides, or polypeptides, hydrocarbon-stapled α-helical peptides, and including any flexible carrier peptide zippers, amino derivatized nucleic acid aptamers and peptide aptamers defined herein, can be substituted for said antibodies in this invention. Preferred flexible carrier aptamers include suitably modified aptamer derivatives or conjugates including but not limited to, those with hapten binding domains defined herein.

Carboxylated Active Agents Coupled to Flexible Carriers.

In another preferred embodiment, any suitable carboxylated AA, defined herein, (i.e. NRTI, PI, MTX) or an active agent that has been converted to an active ester (i.e. 3-nitrophenyl, N-hydroxy-succinimidyl or S-ethyl activated ester) as disclosed herein, is suitably coupled to said flexible carrier through available amine groups. In another preferred embodiment, any suitable hydroxyactive agent-aldehyde derivative, defined herein, is suitably coupled to said flexible carrier through available amino groups on said carrier.

Oxidized Aptamers, Antibodies and Carbohydrates.

In another preferred embodiment, hydroxyl groups on the carbohydrate moiety of the any suitable aptamer or nano-structure, is suitably oxidized to provide aldehydes using Dess-Martin periodinane (DMP), oxidation (DB Dess and JC Martin, J. Org. Chem. 48, 4155-4156 (1983) and J. Am. Chem. Soc. 113, 7277 (1991)), to provide an aldehyde that will couple to any suitable amine-containing active agent (amino-AA), or amino-NCS, defined herein. Alternative oxidizing methods can include either $NaIO_4$ (A. Murayama, et al, Immunochem. 15, 532, 1978), or a suitable oxidizing enzyme such as glucose oxidase. Then, a suitable AA such as primaquine or suitably, hydroxyactive agent-hydrazine is coupled to the aldehydes on the protein to provide a cleav-able hydrazone linkage.

For instance, to about 3 mg of suitable aptamer in 2-4 mL of suitable solvent (i.e. contains DMSO), is added about a 5-50× molar excess of DMP and mixed. After reacting for about 1 hour at 4° C., the reaction is quenched with about 30× molar excess of ethylene glycol. The oxidized aptamer is collected by ultra-filtration (50 kDa MWCO) and recon-stituted in PBS. To the oxidized aptamer is added a 20× molar excess of amino-AA in suitable solvent and allowed to couple for 2-3 hours in the dark at rt. The resulting said AA-Aptamer is purified by Sephadex™ gel chromatogra-phy, or by precipitation.

In other preferred embodiments, any suitable carbohy-drates, cyclodextrins (CD) or CD polymers, or glycopro-teins, or glycopeptides, or glycosylated polymers useful as flexible carriers disclosed herein, can be suitably oxidized when substituted for said aptamer.

Active Agent-Coupled Flexible Carrier Nucleic Acid.

In this example, any suitable carrier nucleic acid "zipper" strand, or carrier polypeptide "zipper" sequence, described previously, is coupled to an active agent. Any suitable derivatized nucleic acid (NA), can be used in this example. For instance, a nucleic acid is suitably amino-derivatized (amino-NA), to provide a suitable double-stranded NA, wherein the "Sense" strand(S), contains a central or nearly central amino functional group (i.e. amino-containing phos-phoramidite). And the complementary "Antisense" (AS) sequence can be a separate strand or part of a single strand with the AS sequence at the opposite end. In either case the S and AS sequences can anneal (i.e. by folding if a single strand) to form a zipper structure or loop.

Nucleic Acid Aldehyde. A 500 mg C18 solid phase extraction (SPE) column is preconditioned with 3 mL of MetOH and 2 mL of water. Then about 0.02 micromoles of said amino-nucleic acid, in 0.1 mL of water is allowed to soak into the column, followed with 0.2 mL more water. Then about 0.1 mL of 3% glutaraldehyde is applied, fol-lowed with 0.1 mL water. The column bottom is plugged and let stand for 30 minutes, then washed with 1.0 mL of water, and 1 mL of 5% MetOH and 1.5 mL of 10% MetOH.

The resulting nucleic acid aldehyde (NA-Ald) is then eluted with about 3 mL of 100% MetOH and concentrated by evaporation in the dark, under flowing nitrogen to about 1 mL. The NA-Ald is purified using chromatography. Alde-hyde is determined colorimetrically and NA is measured by absorbance nm.

The NA-Ald is combined with a slight molar excess of amino-AA, defined herein, in water, based on amino content vs. NA-Ald concentration. The reaction is run for about 4 hours in the dark. The resulting NA-AA conjugate is purified by precipitation with 100% isopropanol at –20° C. and centrifugation.

---

What is claimed is:

1. A Drug Carrier Aptamer Composition that is selected from the group of nucleic acid hairpin compositions that is comprised of two stem regions separated by an intermediate loop region, wherein all said regions contain covalently and sequentially coupled moieties and nucleotides that are in the order of;

5'-(TM-A)-AAA-TGCA-{P-(CL-Drug)}-AA CGC ATA TGC AAA-AACAT-AAA GCA TAT-GCG-A-{P-(CL-Drug)}-AA-GCA-AAA-(TM-B)-3', (that includes Seq ID No. 173) and;

wherein said stem regions each independently contain moieties and nucleotide sequences that are sufficiently complementary in nucleotide sequence so that when said hairpin is folded, said stem regions are brought together to provide sufficient base-pair hybridization to suitably stabilize said aptamer composition that is further comprised of;

a. a first stem region containing a terminal 5' targeting moiety (5'-TM-A) that is selected from the group of nucleic acid aptamers and wherein said (5'-TM-A) is independently and covalently coupled to;

b. a nucleic acid sequence of; AAA-TGCA that is covalently coupled to;

c. moiety P of a first drug carrier moiety, {P-(CL-Drug)} wherein said moiety P is also covalently coupled through a cleavable linkage ("CL"), selected from the group of Cleavable Peptide Linkages including para-aminobenzyloxycarbonyl (PABC), to a ("Drug") moiety selected from the group of anticancer active agents, and wherein said moiety P of said drug carrier moiety is covalently coupled to;

d. a nucleic acid sequence of;

AA CGC ATA TGC AAA-AACAT-AAA GCA TAT-GCG-A, (that includes Seq ID No. 173) that contains said intermediate loop region sequence of; AACAT, wherein said nucleic acid sequence is sequentially and covalently coupled to;

e. a second moiety P of second drug carrier moiety, {P-(CL-Drug)} wherein said moiety P is also covalently coupled through a cleavable linkage ("CL"), selected from the group of Cleavable Peptide Linkages including para-aminobenzyloxycarbonyl (PABC), to a ("Drug") moiety selected from the group of anticancer active agents, and wherein said moiety P is also covalently coupled to;

f. a nucleic acid sequence of; AA-GCA-AAA wherein the 3' end of said sequence is covalently coupled to;

g. a terminal 3' targeting moiety (TM-B-3') that is selected from the group of nucleic acid aptamers.

2. The composition of claim 1 wherein said composition contains covalently and sequentially coupled moieties and nucleic acid sequences that are in the order of;

5'-(TM-A)-AAA-TGCA-{P-(CL-Drug)}-AA CGC ATA TGC AAA-AACAT-AAA GCA TAT-GCG-A-{P-(CL-Drug)}-AA-GCA-AAA-(TM-B)-3', (that includes Seq ID No. 173) and;

wherein said terminal 5' targeting moiety (5'-TM-A) is DNA aptamer AS1411 with the sequence of; 5'-TT GGT GGT GGT GGT TGT GGT GGT GGT GGT-3', (that includes Seq ID No. 174) that can bind nucleolin, and;

wherein said cleavable peptide linkage moiety ("CL"), of said first drug carrier moiety, {P-(CL-Drug)} is a valine-citrulline-p-aminobenzylcarbamate (VC-PABC) linker, and said ("Drug") moiety is paclitaxel, and;

wherein said cleavable peptide linkage moiety ("CL"), of said second drug carrier moiety, {P-(CL-Drug)} is a valine-citrulline-p-aminobenzylcarbamate (VC-PABC) linker, and said ("Drug") moiety is calicheamicin, and;

wherein said terminal 3' targeting moiety (TM-B-3') is RNA Aptamer p53R175H-APT that has the nucleic acid sequence of;

5'-A TTA GCG CAT TIT AAC ATA GGG TGC-3' (that includes Seq ID No. 137) and can specifically bind mutated protein p53.

\*   \*   \*   \*   \*

SEQUENCE LISTING

```
<160> NUMBER OF SEQ ID NOS: 174

<210> SEQ ID NO 1
<211> LENGTH: 27
<212> TYPE: PRT
<213> ORGANISM: Unknown
<220> FEATURE:
<223> OTHER INFORMATION: Bee Venom

<400> SEQUENCE: 1

Gly Ile Gly Ala Val Leu Lys Val Leu Thr Thr Gly Leu Pro Ala Leu
1               5                   10                  15

Ile Ser Trp Ile Lys Arg Lys Arg Gln Gln Cys
            20                  25

<210> SEQ ID NO 2
<211> LENGTH: 19
<212> TYPE: PRT
<213> ORGANISM: Artificial Sequence
<220> FEATURE:
<223> OTHER INFORMATION: Synthetic

<400> SEQUENCE: 2

Arg Leu Trp His Leu Leu Trp Arg Leu Trp Arg Arg Leu His Arg Leu
1               5                   10                  15

Leu Arg Cys
```

```
<210> SEQ ID NO 3
<211> LENGTH: 18
<212> TYPE: PRT
<213> ORGANISM: Artificial Sequence
<220> FEATURE:
<223> OTHER INFORMATION: Synthetic

<400> SEQUENCE: 3

Gly Phe Leu Ser Ile Leu Lys Lys Val Leu Lys Val Met Ala His Met
1               5                   10                  15

Lys Cys

<210> SEQ ID NO 4
<211> LENGTH: 22
<212> TYPE: PRT
<213> ORGANISM: Artificial Sequence
<220> FEATURE:
<223> OTHER INFORMATION: Synthetic

<400> SEQUENCE: 4

Lys Trp Lys Leu Phe Lys Lys Ile Phe Lys Arg Ile Val Gln Arg Ile
1               5                   10                  15

Lys Asp Phe Leu Arg Cys
            20

<210> SEQ ID NO 5
<211> LENGTH: 27
<212> TYPE: PRT
<213> ORGANISM: Artificial Sequence
<220> FEATURE:
<223> OTHER INFORMATION: Synthetic

<400> SEQUENCE: 5

Gly Ile Gly Ala Val Leu Lys Val Leu Thr Thr Gly Leu Pro Ala Leu
1               5                   10                  15

Ile Ser Trp Ile His His His His Glu Glu Cys
            20                  25

<210> SEQ ID NO 6
<211> LENGTH: 21
<212> TYPE: PRT
<213> ORGANISM: Artificial Sequence
<220> FEATURE:
<223> OTHER INFORMATION: Synthetic

<400> SEQUENCE: 6

Gly Ile Gly Ala Ile Leu Lys Val Leu Ala Thr Gly Leu Pro Thr Leu
1               5                   10                  15

Ile Ser Trp Ile Cys
            20

<210> SEQ ID NO 7
<211> LENGTH: 24
<212> TYPE: PRT
<213> ORGANISM: Artificial Sequence
<220> FEATURE:
<223> OTHER INFORMATION: Synthetic

<400> SEQUENCE: 7

Leu Ile Arg Leu Trp Ser His Leu Ile His Ile Trp Phe Gln Asn Arg
1               5                   10                  15

Arg Leu Lys Trp Lys Lys Lys Cys
            20
```

```
<210> SEQ ID NO 8
<211> LENGTH: 19
<212> TYPE: PRT
<213> ORGANISM: Artificial Sequence
<220> FEATURE:
<223> OTHER INFORMATION: Synthetic

<400> SEQUENCE: 8

Phe Phe Gly His Leu Phe Lys Leu Ala Thr Lys Ile Ile Pro Ser Leu
1               5                   10                  15

Phe Gln Cys

<210> SEQ ID NO 9
<211> LENGTH: 25
<212> TYPE: PRT
<213> ORGANISM: Artificial Sequence
<220> FEATURE:
<223> OTHER INFORMATION: Synthetic

<400> SEQUENCE: 9

Lys Lys Leu Ala His Ala Leu His Leu Leu Ala Leu Leu Trp Leu His
1               5                   10                  15

Leu Ala His Ala Leu Lys Lys Ala Cys
            20                  25

<210> SEQ ID NO 10
<211> LENGTH: 27
<212> TYPE: PRT
<213> ORGANISM: Artificial Sequence
<220> FEATURE:
<223> OTHER INFORMATION: Synthetic

<400> SEQUENCE: 10

Lys Trp Lys Ser Phe Leu Lys Thr Phe Lys Lys Ala Val Lys Thr Val
1               5                   10                  15

Leu His Thr Ala Leu Lys Ala Ile Ser Ser Cys
            20                  25

<210> SEQ ID NO 11
<211> LENGTH: 27
<212> TYPE: PRT
<213> ORGANISM: Artificial Sequence
<220> FEATURE:
<223> OTHER INFORMATION: Synthetic

<400> SEQUENCE: 11

Leu His Lys Leu Leu His His Leu Leu His His Leu His Lys Leu Leu
1               5                   10                  15

His His Leu His His Leu Leu His Lys Leu Cys
            20                  25

<210> SEQ ID NO 12
<211> LENGTH: 14
<212> TYPE: PRT
<213> ORGANISM: Artificial Sequence
<220> FEATURE:
<223> OTHER INFORMATION: Synthetic

<400> SEQUENCE: 12

Phe Leu Ala Leu Ile Leu Arg Lys Ile Val Thr Ala Leu Cys
1               5                   10

<210> SEQ ID NO 13
```

```
<211> LENGTH: 27
<212> TYPE: PRT
<213> ORGANISM: Artificial Sequence
<220> FEATURE:
<223> OTHER INFORMATION: Synthetic

<400> SEQUENCE: 13

Gly Trp Trp Leu Ala Leu Ala Glu Ala Glu Ala Glu Ala Leu Ala Leu
1               5                   10                  15

Ala Ser Trp Ile Lys Arg Lys Arg Gln Gln Cys
            20                  25

<210> SEQ ID NO 14
<211> LENGTH: 14
<212> TYPE: PRT
<213> ORGANISM: Artificial Sequence
<220> FEATURE:
<223> OTHER INFORMATION: Synthetic

<400> SEQUENCE: 14

Gly Leu Phe Asp Ile Ile Lys Lys Ile Ala Glu Ser Phe Cys
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Synthetic

<400> SEQUENCE: 15

Ile Leu Gly Lys Ile Trp Glu Gly Ile Lys Ser Leu Phe Cys
1               5                   10

<210> SEQ ID NO 16
<211> LENGTH: 26
<212> TYPE: PRT
<213> ORGANISM: Artificial Sequence
<220> FEATURE:
<223> OTHER INFORMATION: Synthetic

<400> SEQUENCE: 16

Ile Trp Leu Thr Ala Leu Lys Phe Leu Gly Lys His Ala Ala Lys His
1               5                   10                  15

Glu Ala Lys Gln Gln Leu Ser Lys Leu Cys
            20                  25

<210> SEQ ID NO 17
<211> LENGTH: 24
<212> TYPE: PRT
<213> ORGANISM: Artificial Sequence
<220> FEATURE:
<223> OTHER INFORMATION: Synthetic

<400> SEQUENCE: 17

Gly Ile His His Trp Leu His Ser Ala His Glu Phe Gly Glu His Phe
1               5                   10                  15

Val His His Ile Met Asn Ser Cys
            20

<210> SEQ ID NO 18
<211> LENGTH: 14
<212> TYPE: PRT
<213> ORGANISM: Artificial Sequence
<220> FEATURE:
<223> OTHER INFORMATION: Synthetic
```

```
<400> SEQUENCE: 18

Pro Lys Leu Leu Lys Thr Phe Leu Ser Lys Trp Ile Gly Cys
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic

<400> SEQUENCE: 19

Tyr Gly Arg Lys Lys Arg Arg Gln Arg Arg Arg Cys
1               5                   10

<210> SEQ ID NO 20
<211> LENGTH: 16
<212> TYPE: PRT
<213> ORGANISM: Artificial Sequence
<220> FEATURE:
<223> OTHER INFORMATION: Synthetic

<400> SEQUENCE: 20

Phe Lys Ile Gly Gly Phe Ile Lys Lys Leu Trp Arg Ser Lys Leu Ala
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Synthetic

<400> SEQUENCE: 21

Phe Lys Ile Gly Gly Phe Ile Lys Lys Leu Trp Arg Ser Leu Leu Ala
1               5                   10                  15

<210> SEQ ID NO 22
<211> LENGTH: 4
<212> TYPE: PRT
<213> ORGANISM: Artificial Sequence
<220> FEATURE:
<223> OTHER INFORMATION: Synthetic

<400> SEQUENCE: 22

Gly Leu Phe Gly
1

<210> SEQ ID NO 23
<211> LENGTH: 4
<212> TYPE: PRT
<213> ORGANISM: Artificial Sequence
<220> FEATURE:
<223> OTHER INFORMATION: Synthetic

<400> SEQUENCE: 23

Ala Leu Ala Leu
1

<210> SEQ ID NO 24
<211> LENGTH: 4
<212> TYPE: PRT
<213> ORGANISM: Artificial Sequence
<220> FEATURE:
<223> OTHER INFORMATION: Synthetic
```

-continued

```
<400> SEQUENCE: 24

Gly Phe Leu Gly
1

<210> SEQ ID NO 25
<211> LENGTH: 4
<212> TYPE: PRT
<213> ORGANISM: Artificial Sequence
<220> FEATURE:
<223> OTHER INFORMATION: Synthetic

<400> SEQUENCE: 25

Tyr Arg Arg Leu
1

<210> SEQ ID NO 26
<211> LENGTH: 25
<212> TYPE: DNA
<213> ORGANISM: Artificial Sequence
<220> FEATURE:
<223> OTHER INFORMATION: Synthetic

<400> SEQUENCE: 26
gttgtgaggc actgcccca ccatg                                    25

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
gttgtgcagc gcctcacaac                                         20

<210> SEQ ID NO 28
<211> LENGTH: 33
<212> TYPE: DNA
<213> ORGANISM: Artificial Sequence
<220> FEATURE:
<223> OTHER INFORMATION: Synthetic

<400> SEQUENCE: 28
gaggtcatgg tgggggcagc gcctcacaac ctc                          33

<210> SEQ ID NO 29
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(12)
<223> OTHER INFORMATION: n is a, c, g, or t

<400> SEQUENCE: 29
gttgtgaggc nctgcccc                                           18

<210> SEQ ID NO 30
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

-continued

```
<222> LOCATION: (11)..(12)
<223> OTHER INFORMATION: n is a, c, g, or t

<400> SEQUENCE: 30
tttcgacata ntgtggtggt g                                              21

<210> SEQ ID NO 31
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(12)
<223> OTHER INFORMATION: n is a, c, g, or t

<400> SEQUENCE: 31
tcgacatagt ntggtggtgc c                                              21

<210> SEQ ID NO 32
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(9)
<223> OTHER INFORMATION: n is a, c, g, or t

<400> SEQUENCE: 32
catgtgtnac agttcctgca                                               20

<210> SEQ ID NO 33
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(9)
<223> OTHER INFORMATION: n is a, c, g, or t

<400> SEQUENCE: 33
catgaacngg aggcccatc                                                19

<210> SEQ ID NO 34
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: n is a, c, g, or t

<400> SEQUENCE: 34
ttgaggtgcn tgtttgtgc                                                19

<210> SEQ ID NO 35
<211> LENGTH: 17
<212> TYPE: DNA
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (8)..(9)
<223> OTHER INFORMATION: n is a, c, g, or t

<400> SEQUENCE: 35
gagagacngg cgcacag                                               17

<210> SEQ ID NO 36
<211> LENGTH: 25
<212> TYPE: DNA
<213> ORGANISM: Artificial Sequence
<220> FEATURE:
<223> OTHER INFORMATION: Synthetic

<400> SEQUENCE: 36
attagcgcat tttaacatag ggtgc                                     25

<210> SEQ ID NO 37
<211> LENGTH: 18
<212> TYPE: DNA
<213> ORGANISM: Artificial Sequence
<220> FEATURE:
<223> OTHER INFORMATION: Synthetic

<400> SEQUENCE: 37
cgctgccccc accatgag                                             18

<210> SEQ ID NO 38
<211> LENGTH: 28
<212> TYPE: DNA
<213> ORGANISM: Artificial Sequence
<220> FEATURE:
<223> OTHER INFORMATION: Synthetic

<400> SEQUENCE: 38
atgttttgcc aactggccaa gacctgcc                                 28

<210> SEQ ID NO 39
<211> LENGTH: 10
<212> TYPE: DNA
<213> ORGANISM: Artificial Sequence
<220> FEATURE:
<223> OTHER INFORMATION: Synthetic

<400> SEQUENCE: 39
ccgcccggca                                                      10

<210> SEQ ID NO 40
<211> LENGTH: 21
<212> TYPE: DNA
<213> ORGANISM: Artificial Sequence
<220> FEATURE:
<223> OTHER INFORMATION: Synthetic

<400> SEQUENCE: 40
ccatcatcac actggaagac t                                         21

<210> SEQ ID NO 41
<211> LENGTH: 16
<212> TYPE: DNA
<213> ORGANISM: Artificial Sequence
<220> FEATURE:
<223> OTHER INFORMATION: Synthetic

<400> SEQUENCE: 41
gtctgtgact tgcacg                                               16
```

-continued

```
<210> SEQ ID NO 42
<211> LENGTH: 13
<212> TYPE: DNA
<213> ORGANISM: Artificial Sequence
<220> FEATURE:
<223> OTHER INFORMATION: Synthetic

<400> SEQUENCE: 42
cccctgcacc agc                                                        13

<210> SEQ ID NO 43
<211> LENGTH: 16
<212> TYPE: DNA
<213> ORGANISM: Artificial Sequence
<220> FEATURE:
<223> OTHER INFORMATION: Synthetic

<400> SEQUENCE: 43
ttctgggaca gccaag                                                     16

<210> SEQ ID NO 44
<211> LENGTH: 14
<212> TYPE: DNA
<213> ORGANISM: Artificial Sequence
<220> FEATURE:
<223> OTHER INFORMATION: Synthetic

<400> SEQUENCE: 44
atccgagtgg aagg                                                       14

<210> SEQ ID NO 45
<211> LENGTH: 14
<212> TYPE: DNA
<213> ORGANISM: Artificial Sequence
<220> FEATURE:
<223> OTHER INFORMATION: Synthetic

<400> SEQUENCE: 45
ccgagtggaa ggat                                                       14

<210> SEQ ID NO 46
<211> LENGTH: 29
<212> TYPE: DNA
<213> ORGANISM: Artificial Sequence
<220> FEATURE:
<223> OTHER INFORMATION: Synthetic

<400> SEQUENCE: 46
ccaccatgag cgctgctcag atagcgatg                                       29

<210> SEQ ID NO 47
<211> LENGTH: 16
<212> TYPE: DNA
<213> ORGANISM: Artificial Sequence
<220> FEATURE:
<223> OTHER INFORMATION: Synthetic

<400> SEQUENCE: 47
ctgcccccag ggagca                                                     16

<210> SEQ ID NO 48
<211> LENGTH: 11
<212> TYPE: DNA
<213> ORGANISM: Artificial Sequence
<220> FEATURE:
```

```
<223> OTHER INFORMATION: Synthetic

<400> SEQUENCE: 48
atttgcgtgt g                                                    11

<210> SEQ ID NO 49
<211> LENGTH: 23
<212> TYPE: DNA
<213> ORGANISM: Artificial Sequence
<220> FEATURE:
<223> OTHER INFORMATION: Synthetic

<400> SEQUENCE: 49
ggcccctgca ccagccccct cct                                       23

<210> SEQ ID NO 50
<211> LENGTH: 41
<212> TYPE: RNA
<213> ORGANISM: Artificial Sequence
<220> FEATURE:
<223> OTHER INFORMATION: Synthetic

<400> SEQUENCE: 50
ccggaguuga ggcguagaug guucagaucc gaacgaugaa g                   41

<210> SEQ ID NO 51
<211> LENGTH: 26
<212> TYPE: DNA
<213> ORGANISM: Artificial Sequence
<220> FEATURE:
<223> OTHER INFORMATION: Synthetic

<400> SEQUENCE: 51
ggtggtggtg gttgtggtgg tggtgg                                    26

<210> SEQ ID NO 52
<211> LENGTH: 5
<212> TYPE: PRT
<213> ORGANISM: Artificial Sequence
<220> FEATURE:
<223> OTHER INFORMATION: Synthetic

<400> SEQUENCE: 52

Cys Asn Gly Arg Cys
1               5

<210> SEQ ID NO 53
<211> LENGTH: 4
<212> TYPE: PRT
<213> ORGANISM: Artificial Sequence
<220> FEATURE:
<223> OTHER INFORMATION: Synthetic

<400> SEQUENCE: 53

Arg Arg Arg Arg
1

<210> SEQ ID NO 54
<211> LENGTH: 5
<212> TYPE: PRT
<213> ORGANISM: Artificial Sequence
<220> FEATURE:
<223> OTHER INFORMATION: Synthetic

<400> SEQUENCE: 54

Arg Arg Arg Arg Lys
```

-continued 1                5

<210> SEQ ID NO 55
<211> LENGTH: 4
<212> TYPE: PRT
<213> ORGANISM: Artificial Sequence
<220> FEATURE:
<223> OTHER INFORMATION: Synthetic

<400> SEQUENCE: 55

Thr Cys Asn Thr
1

<210> SEQ ID NO 56
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(12)
<223> OTHER INFORMATION: X is propargylcine

<400> SEQUENCE: 56

Cys Asn Gly Arg Cys Arg Arg Arg Arg Gly Xaa Gly Arg Arg Arg Arg
1                5                   10                  15

Lys Arg Gly Asp
          20

<210> SEQ ID NO 57
<211> LENGTH: 5
<212> TYPE: PRT
<213> ORGANISM: Artificial Sequence
<220> FEATURE:
<223> OTHER INFORMATION: Synthetic

<400> SEQUENCE: 57

Cys Arg Gly Asp Lys
1                5

<210> SEQ ID NO 58
<211> LENGTH: 4
<212> TYPE: PRT
<213> ORGANISM: Artificial Sequence
<220> FEATURE:
<223> OTHER INFORMATION: Synthetic

<400> SEQUENCE: 58

Arg Gly Pro Asp
1

<210> SEQ ID NO 59
<211> LENGTH: 6
<212> TYPE: PRT
<213> ORGANISM: Artificial Sequence
<220> FEATURE:
<223> OTHER INFORMATION: Synthetic

<400> SEQUENCE: 59

Thr Gly Ala Thr Ala Ala
1                5

<210> SEQ ID NO 60
<211> LENGTH: 6
<212> TYPE: PRT
<213> ORGANISM: Artificial Sequence -continued

```
<220> FEATURE:
<223> OTHER INFORMATION: Synthetic

<400> SEQUENCE: 60

Thr Gly Ala Thr Ala Gly
1               5

<210> SEQ ID NO 61
<211> LENGTH: 6
<212> TYPE: PRT
<213> ORGANISM: Artificial Sequence
<220> FEATURE:
<223> OTHER INFORMATION: Synthetic

<400> SEQUENCE: 61

Ala Gly Ala Thr Ala Ala
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic

<400> SEQUENCE: 62

Ala Gly Ala Thr Ala Gly
1               5

<210> SEQ ID NO 63
<211> LENGTH: 4
<212> TYPE: PRT
<213> ORGANISM: Artificial Sequence
<220> FEATURE:
<223> OTHER INFORMATION: Synthetic

<400> SEQUENCE: 63

Lys Ala Leu Ala
1

<210> SEQ ID NO 64
<211> LENGTH: 10
<212> TYPE: PRT
<213> ORGANISM: Artificial Sequence
<220> FEATURE:
<223> OTHER INFORMATION: Synthetic

<400> SEQUENCE: 64

Glu Gln Lys Leu Ile Ser Glu Glu Asp Leu
1               5                   10

<210> SEQ ID NO 65
<211> LENGTH: 8
<212> TYPE: PRT
<213> ORGANISM: Artificial Sequence
<220> FEATURE:
<223> OTHER INFORMATION: Synthetic

<400> SEQUENCE: 65

Asp Tyr Lys Asp Asp Asp Asp Lys
1               5

<210> SEQ ID NO 66
<211> LENGTH: 9
<212> TYPE: PRT
<213> ORGANISM: Artificial Sequence
<220> FEATURE:
```

<223> OTHER INFORMATION: Synthetic

<400> SEQUENCE: 66

Thr Glu Thr Ser Gln Val Ala Pro Ala
1               5

<210> SEQ ID NO 67
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: n is a phosphoramidite

<400> SEQUENCE: 67
tgcanacgca tatgcaaa                                            18

<210> SEQ ID NO 68
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(15)
<223> OTHER INFORMATION: n is a phosphoramidite

<400> SEQUENCE: 68
aaagcatatg cganagca                                            18

<210> SEQ ID NO 69
<211> LENGTH: 26
<212> TYPE: DNA
<213> ORGANISM: Artificial Sequence
<220> FEATURE:
<223> OTHER INFORMATION: Synthetic

<400> SEQUENCE: 69
ggtggtggtg gttgtggtgg tggtgg                                   26

<210> SEQ ID NO 70
<211> LENGTH: 30
<212> TYPE: DNA
<213> ORGANISM: Artificial Sequence
<220> FEATURE:
<223> OTHER INFORMATION: Synthetic

<400> SEQUENCE: 70
ggtggtgggg ggggttggta gggtgtcttc                               30

<210> SEQ ID NO 71
<211> LENGTH: 15
<212> TYPE: DNA
<213> ORGANISM: Artificial Sequence
<220> FEATURE:
<223> OTHER INFORMATION: Synthetic

<400> SEQUENCE: 71
ggttggtgtg gttgg                                               15

<210> SEQ ID NO 72
<211> LENGTH: 88
<212> TYPE: DNA

-continued

```
<213> ORGANISM: Artificial Sequence
<220> FEATURE:
<223> OTHER INFORMATION: Synthetic

<400> SEQUENCE: 72
cctgccacgc tccgcacttc ggaggagttc tgcagcgatc ttgatcgggg acgggggaga      60
aaggttttaa gcttggcacc cgcatcgt                                        88

<210> SEQ ID NO 73
<211> LENGTH: 30
<212> TYPE: DNA
<213> ORGANISM: Artificial Sequence
<220> FEATURE:
<223> OTHER INFORMATION: Synthetic

<400> SEQUENCE: 73
taccgcaaaa aaaaacaaga atcgctgcag                                      30

<210> SEQ ID NO 74
<211> LENGTH: 15
<212> TYPE: DNA
<213> ORGANISM: Artificial Sequence
<220> FEATURE:
<223> OTHER INFORMATION: Synthetic

<400> SEQUENCE: 74
gcggagcgtg gcagg                                                      15

<210> SEQ ID NO 75
<211> LENGTH: 20
<212> TYPE: DNA
<213> ORGANISM: Artificial Sequence
<220> FEATURE:
<223> OTHER INFORMATION: Synthetic

<400> SEQUENCE: 75
ctctcctctt accagattcg                                                 20

<210> SEQ ID NO 76
<211> LENGTH: 89
<212> TYPE: DNA
<213> ORGANISM: Artificial Sequence
<220> FEATURE:
<223> OTHER INFORMATION: Synthetic

<400> SEQUENCE: 76
cgaatctggt aagaggagag gggtggtttc cgcagcgatt cttgatcgcg gaagtcggtg      60
gggagggtta agcttggcac ccgcatcgt                                       89

<210> SEQ ID NO 77
<211> LENGTH: 91
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(31)
<223> OTHER INFORMATION: n is a, c, g or t
<220> FEATURE:
<221> NAME/KEY: misc_feature
<222> LOCATION: (51)..(70)
<223> OTHER INFORMATION: n is a, c, g or t

<400> SEQUENCE: 77
cctgccacgc tccgcaagct tnnnnnnnnn nctgcagcga ttcttgatcg nnnnnnnnnn      60
```

-continued

```
nnnnnnnnnn taagcttggc acccgcatcg t                              91

<210> SEQ ID NO 78
<211> LENGTH: 48
<212> TYPE: DNA
<213> ORGANISM: Artificial Sequence
<220> FEATURE:
<223> OTHER INFORMATION: Synthetic

<400> SEQUENCE: 78
cctgccacgc tccgctcact gacctggggg agtattgcgg aggaaggt              48

<210> SEQ ID NO 79
<211> LENGTH: 15
<212> TYPE: DNA
<213> ORGANISM: Artificial Sequence
<220> FEATURE:
<223> OTHER INFORMATION: Synthetic

<400> SEQUENCE: 79
gcggagcgtg gcagg                                                 15

<210> SEQ ID NO 80
<211> LENGTH: 21
<212> TYPE: DNA
<213> ORGANISM: Artificial Sequence
<220> FEATURE:
<223> OTHER INFORMATION: Synthetic

<400> SEQUENCE: 80
acgatgcggg tgccaagctt a                                          21

<210> SEQ ID NO 81
<211> LENGTH: 14
<212> TYPE: DNA
<213> ORGANISM: Artificial Sequence
<220> FEATURE:
<223> OTHER INFORMATION: Synthetic

<400> SEQUENCE: 81
gcctcgcacc gtcc                                                  14

<210> SEQ ID NO 82
<211> LENGTH: 12
<212> TYPE: DNA
<213> ORGANISM: Artificial Sequence
<220> FEATURE:
<223> OTHER INFORMATION: Synthetic

<400> SEQUENCE: 82
cccaggtcag tg                                                    12

<210> SEQ ID NO 83
<211> LENGTH: 30
<212> TYPE: DNA
<213> ORGANISM: Artificial Sequence
<220> FEATURE:
<223> OTHER INFORMATION: Synthetic

<400> SEQUENCE: 83
taccgcaaaa aaaaacaaga atcgctgcag                                 30

<210> SEQ ID NO 84
<211> LENGTH: 41
<212> TYPE: DNA
```

<213> ORGANISM: Artificial Sequence
<220> FEATURE:
<223> OTHER INFORMATION: Synthetic

<400> SEQUENCE: 84
atctaactgc tgcgccgccg ggaaaatact gtacggttag a                            41

<210> SEQ ID NO 85
<211> LENGTH: 50
<212> TYPE: DNA
<213> ORGANISM: Artificial Sequence
<220> FEATURE:
<223> OTHER INFORMATION: Synthetic

<400> SEQUENCE: 85
atccagagtg acgcagcatg ccctagttac tactactctt tttagcaaac                   50

<210> SEQ ID NO 86
<211> LENGTH: 47
<212> TYPE: DNA
<213> ORGANISM: Artificial Sequence
<220> FEATURE:
<223> OTHER INFORMATION: Synthetic

<400> SEQUENCE: 86
aacaccggga ggatagttcg gtggctgttc agggtctcct cccggtg                      47

<210> SEQ ID NO 87
<211> LENGTH: 56
<212> TYPE: RNA
<213> ORGANISM: Artificial Sequence
<220> FEATURE:
<223> OTHER INFORMATION: Synthetic

<400> SEQUENCE: 87
gggaggacga ugcggaucag ccauguuuac gucacuccuu gucaauccuc aucggc            56

<210> SEQ ID NO 88
<211> LENGTH: 49
<212> TYPE: DNA
<213> ORGANISM: Artificial Sequence
<220> FEATURE:
<223> OTHER INFORMATION: Synthetic

<400> SEQUENCE: 88
tgagggcgga agaactaatt tgggacggat tgcggccgtt gtctgtggc                     49

<210> SEQ ID NO 89
<211> LENGTH: 28
<212> TYPE: DNA
<213> ORGANISM: Artificial Sequence
<220> FEATURE:
<223> OTHER INFORMATION: Synthetic

<400> SEQUENCE: 89
ttggtggtgg tggttgtggt ggtggtgg                                           28

<210> SEQ ID NO 90
<211> LENGTH: 104
<212> TYPE: RNA
<213> ORGANISM: Artificial Sequence
<220> FEATURE:
<223> OTHER INFORMATION: Synthetic

<400> SEQUENCE: 90
ggcgcuccga ccuuagucuc ugcaagauaa accgugcuau ugaccacccu caacacacuu        60

-continued auuuaaugua uugaacggac cuacgaaccg uguagcacag caga                    104

<210> SEQ ID NO 91
<211> LENGTH: 46
<212> TYPE: DNA
<213> ORGANISM: Artificial Sequence
<220> FEATURE:
<223> OTHER INFORMATION: Synthetic

<400> SEQUENCE: 91
cctactaatg ataaaccact ggtgaatcgc tcaagtcagt agtagg                  46

<210> SEQ ID NO 92
<211> LENGTH: 81
<212> TYPE: RNA
<213> ORGANISM: Artificial Sequence
<220> FEATURE:
<223> OTHER INFORMATION: Synthetic

<400> SEQUENCE: 92
gggaggacga ugcggaauug agggaccacg cgcugcuugu ugugauaagc aguuugucgu   60
gauggcagac gacucgcccg a                                            81

<210> SEQ ID NO 93
<211> LENGTH: 152
<212> TYPE: RNA
<213> ORGANISM: Artificial Sequence
<220> FEATURE:
<223> OTHER INFORMATION: Synthetic

<400> SEQUENCE: 93
gguugauugu ccgucaauca uggcgggagg acgaugcgga auugagggac cacgcgcugc   60
uuguugugau aagcaguuug ucgugauggc agacgacucg cccgucaugu guauguuggg  120
gauuaacgcc ugauugaguu cagcccacau ac                                152

<210> SEQ ID NO 94
<211> LENGTH: 198
<212> TYPE: RNA
<213> ORGANISM: Artificial Sequence
<220> FEATURE:
<223> OTHER INFORMATION: Synthetic

<400> SEQUENCE: 94
gggaggacga ugcggaauug agggaccacg cgcugcuugu ugugauaagc aguuugucgu   60
gauggcagac gacucgcccg aggaauggua cgguacuucc auugucaugu guauguuggg  120
gauuaacgcc ugauugaguu cagcccacau acuuuguuga uuguccguca aucauggcaa  180
aagugcacgc uacuuucc                                                198

<210> SEQ ID NO 95
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(22)
<223> OTHER INFORMATION: X is thioredoxin

<400> SEQUENCE: 95

Xaa Ser Ser Cys Asn Met Gly Trp Asp Thr Pro Ala Cys Cys Val Trp
1               5                   10                  15

```
Phe Pro Tyr Trp Val Xaa
            20

<210> SEQ ID NO 96
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(22)
<223> OTHER INFORMATION: X is thioredoxin

<400> SEQUENCE: 96

Xaa Met Ala Val Gly Leu Val Leu Cys Asp Trp Trp Leu Gly Glu Tyr
1               5                   10                  15

Leu Leu Glu Leu Ala Xaa
            20

<210> SEQ ID NO 97
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(22)
<223> OTHER INFORMATION: X is thioredoxin

<400> SEQUENCE: 97

Xaa Pro Val Leu Gln Pro Ala Leu Ser Leu Ser Cys Gly Pro Glu Pro
1               5                   10                  15

Leu Leu Leu Ser Cys Xaa
            20

<210> SEQ ID NO 98
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(22)
<223> OTHER INFORMATION: X is thioredoxin

<400> SEQUENCE: 98

Xaa Ile Glu Val Thr Phe Val Asn Arg Arg Gly Asp Gly Ala Glu Leu
1               5                   10                  15

Trp Tyr Leu Ser Ala Xaa
            20

<210> SEQ ID NO 99
<211> LENGTH: 20
<212> TYPE: PRT
<213> ORGANISM: Artificial Sequence
<220> FEATURE:
<223> OTHER INFORMATION: Synthetic

<400> SEQUENCE: 99

Ala Leu Ile Met Gly Cys Tyr Val Leu Val Gly Thr Pro Arg Val Val
1               5                   10                  15

Arg Phe Arg Ser
            20
```

-continued

```
<210> SEQ ID NO 100
<211> LENGTH: 42
<212> TYPE: PRT
<213> ORGANISM: Artificial Sequence
<220> FEATURE:
<223> OTHER INFORMATION: Synthetic

<400> SEQUENCE: 100

Leu Asn Phe Tyr Arg His Gly Phe Leu Pro Asn Ala Val Met Ala Ser
1               5                   10                  15

Met Leu Glu Val Gly Pro Trp Phe Glu Leu Leu Gly Leu Cys Gly Leu
            20                  25                  30

Ala Gly His Pro Leu Ser Ser Leu Arg Ile
        35                  40

<210> SEQ ID NO 101
<211> LENGTH: 21
<212> TYPE: PRT
<213> ORGANISM: Artificial Sequence
<220> FEATURE:
<223> OTHER INFORMATION: Synthetic

<400> SEQUENCE: 101

Gly Leu Ala His Gly Val Ala Ile Tyr Thr Glu Leu Pro Leu Thr Arg
1               5                   10                  15

Met Ala Arg Gly Gly
            20

<210> SEQ ID NO 102
<211> LENGTH: 19
<212> TYPE: PRT
<213> ORGANISM: Artificial Sequence
<220> FEATURE:
<223> OTHER INFORMATION: Synthetic

<400> SEQUENCE: 102

Gly Lys Met Asn Gly Val Leu Pro Leu Ala Trp Pro Ser Leu Tyr Leu
1               5                   10                  15

Arg Leu Pro

<210> SEQ ID NO 103
<211> LENGTH: 8
<212> TYPE: PRT
<213> ORGANISM: Artificial Sequence
<220> FEATURE:
<223> OTHER INFORMATION: Synthetic

<400> SEQUENCE: 103

Ser Pro Trp Pro Arg Pro Thr Tyr
1               5

<210> SEQ ID NO 104
<211> LENGTH: 13
<212> TYPE: PRT
<213> ORGANISM: Artificial Sequence
<220> FEATURE:
<223> OTHER INFORMATION: Synthetic

<400> SEQUENCE: 104

Tyr Cys Ala Tyr Tyr Ser Pro Arg His Lys Thr Thr Phe
1               5                   10

<210> SEQ ID NO 105
```

-continued

```
<211> LENGTH: 42
<212> TYPE: PRT
<213> ORGANISM: Artificial Sequence
<220> FEATURE:
<223> OTHER INFORMATION: Synthetic

<400> SEQUENCE: 105

Ala Ser Glu Gly Ala Asp Gly Ala Ile Cys Gly Tyr Asn Leu Ala Thr
1               5                   10                  15

Leu Val Met Leu Gly Pro Ser Glu Arg Val Phe Cys Pro Leu Cys Glu
            20                  25                  30

Pro Cys Ser Ser Asp Ile Tyr Glu Leu Met
        35                  40

<210> SEQ ID NO 106
<211> LENGTH: 14
<212> TYPE: PRT
<213> ORGANISM: Artificial Sequence
<220> FEATURE:
<223> OTHER INFORMATION: Synthetic

<400> SEQUENCE: 106

Ser Gly Lys Lys Arg Tyr Asp Arg Glu Phe Leu Leu Gly Phe
1               5                   10

<210> SEQ ID NO 107
<211> LENGTH: 16
<212> TYPE: PRT
<213> ORGANISM: Artificial Sequence
<220> FEATURE:
<223> OTHER INFORMATION: Synthetic

<400> SEQUENCE: 107

Arg Gln Ile Lys Ile Trp Phe Gln Asn Arg Arg Met Lys Trp Lys Lys
1               5                   10                  15

<210> SEQ ID NO 108
<211> LENGTH: 16
<212> TYPE: PRT
<213> ORGANISM: Artificial Sequence
<220> FEATURE:
<223> OTHER INFORMATION: Synthetic

<400> SEQUENCE: 108

Lys Lys Trp Lys Met Arg Arg Asn Gln Phe Trp Val Lys Val Gln Arg
1               5                   10                  15

<210> SEQ ID NO 109
<211> LENGTH: 16
<212> TYPE: PRT
<213> ORGANISM: Artificial Sequence
<220> FEATURE:
<223> OTHER INFORMATION: Synthetic

<400> SEQUENCE: 109

Arg Arg Trp Arg Arg Trp Trp Arg Arg Trp Trp Arg Arg Trp Arg Arg
1               5                   10                  15

<210> SEQ ID NO 110
<211> LENGTH: 18
<212> TYPE: PRT
<213> ORGANISM: Artificial Sequence
<220> FEATURE:
<223> OTHER INFORMATION: Synthetic

<400> SEQUENCE: 110
```

```
Arg Gln Ile Lys Ile Trp Phe Gln Asn Arg Arg Met Lys Trp Lys Lys
1               5                   10                  15

Glu Asn

<210> SEQ ID NO 111
<211> LENGTH: 7
<212> TYPE: PRT
<213> ORGANISM: Artificial Sequence
<220> FEATURE:
<223> OTHER INFORMATION: Synthetic

<400> SEQUENCE: 111

Arg Arg Met Lys Trp Lys Lys
1               5

<210> SEQ ID NO 112
<211> LENGTH: 13
<212> TYPE: PRT
<213> ORGANISM: Artificial Sequence
<220> FEATURE:
<223> OTHER INFORMATION: Synthetic

<400> SEQUENCE: 112

Gly Arg Lys Lys Arg Arg Gln Arg Arg Arg Pro Pro Gln
1               5                   10

<210> SEQ ID NO 113
<211> LENGTH: 11
<212> TYPE: PRT
<213> ORGANISM: Artificial Sequence
<220> FEATURE:
<223> OTHER INFORMATION: Synthetic

<400> SEQUENCE: 113

Tyr Gly Arg Lys Lys Arg Arg Gln Arg Arg Arg
1               5                   10

<210> SEQ ID NO 114
<211> LENGTH: 14
<212> TYPE: PRT
<213> ORGANISM: Artificial Sequence
<220> FEATURE:
<223> OTHER INFORMATION: Synthetic

<400> SEQUENCE: 114

Pro Thr Ser Gln Ser Arg Gly Asp Pro Thr Gly Pro Lys Glu
1               5                   10

<210> SEQ ID NO 115
<211> LENGTH: 17
<212> TYPE: PRT
<213> ORGANISM: Artificial Sequence
<220> FEATURE:
<223> OTHER INFORMATION: Synthetic

<400> SEQUENCE: 115

Ala Val Gly Ala Ile Gly Ala Leu Phe Leu Gly Phe Leu Gly Ala Ala
1               5                   10                  15

Gly

<210> SEQ ID NO 116
<211> LENGTH: 17
<212> TYPE: PRT
<213> ORGANISM: Artificial Sequence
<220> FEATURE:
<223> OTHER INFORMATION: Synthetic
```

-continued

<400> SEQUENCE: 116

Gly Ala Leu Phe Leu Gly Trp Leu Gly Ala Ala Gly Ser Thr Met Gly
1               5                   10                  15

Ala

<210> SEQ ID NO 117
<211> LENGTH: 30
<212> TYPE: PRT
<213> ORGANISM: Artificial Sequence
<220> FEATURE:
<223> OTHER INFORMATION: Synthetic

<400> SEQUENCE: 117

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val Met Pro Gly
            20                  25                  30

<210> SEQ ID NO 118
<211> LENGTH: 24
<212> TYPE: PRT
<213> ORGANISM: Artificial Sequence
<220> FEATURE:
<223> OTHER INFORMATION: Synthetic

<400> SEQUENCE: 118

Asp Arg Val Ile Glu Val Val Gln Gly Ala Tyr Arg Ala Ile Arg Asn
1               5                   10                  15

Ile Pro Arg Arg Ile Arg Gln Gly
            20

<210> SEQ ID NO 119
<211> LENGTH: 17
<212> TYPE: PRT
<213> ORGANISM: Artificial Sequence
<220> FEATURE:
<223> OTHER INFORMATION: Synthetic

<400> SEQUENCE: 119

Met Gly Leu Gly Leu His Leu Leu Val Leu Ala Ala Ala Leu Gln Gly
1               5                   10                  15

Ala

<210> SEQ ID NO 120
<211> LENGTH: 27
<212> TYPE: PRT
<213> ORGANISM: Artificial Sequence
<220> FEATURE:
<223> OTHER INFORMATION: Synthetic

<400> SEQUENCE: 120

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 121
<211> LENGTH: 12
<212> TYPE: PRT
<213> ORGANISM: Artificial Sequence
<220> FEATURE:
<223> OTHER INFORMATION: Synthetic

<400> SEQUENCE: 121

Pro Leu Ser Ser Ile Phe Ser Arg Ile Gly Asp Pro
1               5                   10

<210> SEQ ID NO 122
<211> LENGTH: 27
<212> TYPE: PRT
<213> ORGANISM: Artificial Sequence
<220> FEATURE:
<223> OTHER INFORMATION: Synthetic

<400> SEQUENCE: 122

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 123
<211> LENGTH: 18
<212> TYPE: PRT
<213> ORGANISM: Artificial Sequence
<220> FEATURE:
<223> OTHER INFORMATION: Synthetic

<400> SEQUENCE: 123

Arg Gly Gly Arg Leu Ser Tyr Ser Arg Arg Phe Ser Thr Ser Thr
1               5                   10                  15

Gly Arg

<210> SEQ ID NO 124
<211> LENGTH: 16
<212> TYPE: PRT
<213> ORGANISM: Artificial Sequence
<220> FEATURE:
<223> OTHER INFORMATION: Synthetic

<400> SEQUENCE: 124

Ala Ala Val Ala Leu Leu Pro Ala Val Leu Leu Ala Leu Leu Ala Pro
1               5                   10                  15

<210> SEQ ID NO 125
<211> LENGTH: 12
<212> TYPE: PRT
<213> ORGANISM: Artificial Sequence
<220> FEATURE:
<223> OTHER INFORMATION: Synthetic

<400> SEQUENCE: 125

Ala Ala Val Leu Leu Pro Val Leu Leu Ala Ala Pro
1               5                   10

<210> SEQ ID NO 126
<211> LENGTH: 15
<212> TYPE: PRT
<213> ORGANISM: Artificial Sequence
<220> FEATURE:
<223> OTHER INFORMATION: Synthetic

<400> SEQUENCE: 126

Val Thr Val Leu Ala Leu Gly Ala Leu Ala Gly Val Gly Val Gly
1               5                   10                  15

<210> SEQ ID NO 127
<211> LENGTH: 30
<212> TYPE: PRT

-continued

```
<213> ORGANISM: Artificial Sequence
<220> FEATURE:
<223> OTHER INFORMATION: Synthetic

<400> SEQUENCE: 127

Val Ala Tyr Ile Ser Arg Gly Gly Val Ser Thr Tyr Tyr Ser Asp Thr
1               5                   10                  15

Val Lys Gly Arg Phe Thr Arg Gln Lys Tyr Asn Lys Arg Ala
            20                  25                  30

<210> SEQ ID NO 128
<211> LENGTH: 18
<212> TYPE: PRT
<213> ORGANISM: Artificial Sequence
<220> FEATURE:
<223> OTHER INFORMATION: Synthetic

<400> SEQUENCE: 128

Lys Leu Ala Leu Lys Leu Ala Leu Lys Ala Leu Lys Ala Ala Leu Lys
1               5                   10                  15

Leu Ala

<210> SEQ ID NO 129
<211> LENGTH: 30
<212> TYPE: PRT
<213> ORGANISM: Artificial Sequence
<220> FEATURE:
<223> OTHER INFORMATION: Synthetic

<400> SEQUENCE: 129

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 130
<211> LENGTH: 24
<212> TYPE: PRT
<213> ORGANISM: Artificial Sequence
<220> FEATURE:
<223> OTHER INFORMATION: Synthetic

<400> SEQUENCE: 130

Gly Leu Phe Glu Ala Ile Ala Gly Phe Ile Glu Asn Gly Trp Glu Gly
1               5                   10                  15

Met Ile Asp Gly Gly Gly Tyr Cys
            20

<210> SEQ ID NO 131
<211> LENGTH: 7
<212> TYPE: PRT
<213> ORGANISM: Artificial Sequence
<220> FEATURE:
<223> OTHER INFORMATION: Synthetic

<400> SEQUENCE: 131

Arg Arg Arg Arg Arg Arg Arg
1               5

<210> SEQ ID NO 132
<211> LENGTH: 26
<212> TYPE: PRT
<213> ORGANISM: Artificial Sequence
<220> FEATURE:
<223> OTHER INFORMATION: Synthetic
```

<400> SEQUENCE: 132

Ala Ala Val Ala Leu Leu Pro Ala Val Leu Leu Ala Leu Leu Ala Pro
1               5                   10                  15

Val Gln Arg Lys Arg Gln Lys Leu Met Pro
            20                  25

<210> SEQ ID NO 133
<211> LENGTH: 23
<212> TYPE: PRT
<213> ORGANISM: Artificial Sequence
<220> FEATURE:
<223> OTHER INFORMATION: Synthetic

<400> SEQUENCE: 133

Met Gly Leu Gly Leu His Leu Leu Val Leu Ala Ala Ala Leu Gln Gly
1               5                   10                  15

Ala Lys Lys Lys Arg Lys Val
            20

<210> SEQ ID NO 134
<211> LENGTH: 14
<212> TYPE: PRT
<213> ORGANISM: Artificial Sequence
<220> FEATURE:
<223> OTHER INFORMATION: Synthetic

<400> SEQUENCE: 134

Thr Gln Pro Arg Glu Glu Gln Tyr Asn Ser Thr Phe Arg Val
1               5                   10

<210> SEQ ID NO 135
<211> LENGTH: 14
<212> TYPE: PRT
<213> ORGANISM: Artificial Sequence
<220> FEATURE:
<223> OTHER INFORMATION: Synthetic

<400> SEQUENCE: 135

Asp Gly Cys Ser Lys Ala Pro Lys Leu Pro Ala Ala Leu Cys
1               5                   10

<210> SEQ ID NO 136
<211> LENGTH: 8
<212> TYPE: PRT
<213> ORGANISM: Artificial Sequence
<220> FEATURE:
<223> OTHER INFORMATION: Synthetic

<400> SEQUENCE: 136

Tyr Gly Gly Phe Leu Arg Arg Gly
1               5

<210> SEQ ID NO 137
<211> LENGTH: 25
<212> TYPE: DNA
<213> ORGANISM: Artificial Sequence
<220> FEATURE:
<223> OTHER INFORMATION: Synthetic

<400> SEQUENCE: 137
attagcgcat tttaacatag ggtgc                                         25

<210> SEQ ID NO 138
<211> LENGTH: 28

-continued

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a phosphoramidite

<400> SEQUENCE: 138
naaatcccgc aaatttacgg cgtataaa                                          28

<210> SEQ ID NO 139
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (28)..(28)
<223> OTHER INFORMATION: n is a phosphoramidite

<400> SEQUENCE: 139
aaaatacgcc gtaaatttgc gggaaaan                                          28

<210> SEQ ID NO 140
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: n is a phosphoramidite

<400> SEQUENCE: 140
naaatcccnc aaatttacgg cgtataaa                                          28

<210> SEQ ID NO 141
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(45)
<223> OTHER INFORMATION: n is a phosphoramidite

<400> SEQUENCE: 141
naaatccana attagcgcat tttaacatag ggtgcaaagg aaaan                       45

<210> SEQ ID NO 142
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(6)
<223> OTHER INFORMATION: n is a phosphoramidite

<400> SEQUENCE: 142
tcccncaaat ttacggcgta taaa                                              24

<210> SEQ ID NO 143
```

```
<211> LENGTH: 24
<212> TYPE: DNA
<213> ORGANISM: Artificial Sequence
<220> FEATURE:
<223> OTHER INFORMATION: Synthetic

<400> SEQUENCE: 143
aaaatacgcc gtaaatttgc ggga                                               24

<210> SEQ ID NO 144
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(14)
<223> OTHER INFORMATION: n is a phosphoramidite

<400> SEQUENCE: 144
nccatagtgg attncgaaa                                                     19

<210> SEQ ID NO 145
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a phosphoramidite

<400> SEQUENCE: 145
ngcaatcctg agcacg                                                        16

<210> SEQ ID NO 146
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(16)
<223> OTHER INFORMATION: n is a phosphoramidite

<400> SEQUENCE: 146
ngtgctcacc gaatgnaaa                                                     19

<210> SEQ ID NO 147
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(19)
<223> OTHER INFORMATION: n is a phosphoramidite

<400> SEQUENCE: 147
aaancantcg gactatggn                                                     19

<210> SEQ ID NO 148
<211> LENGTH: 33
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (1)..(31)
<223> OTHER INFORMATION: n is a phosphoramidite

<400> SEQUENCE: 148
nccccccncc tgttgggngg ggggtttttt ntt                                  33

<210> SEQ ID NO 149
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(31)
<223> OTHER INFORMATION: n is a phosphoramidite

<400> SEQUENCE: 149
nccccccncc tgttggggng ggggtttttt ntt                                  33

<210> SEQ ID NO 150
<211> LENGTH: 17
<212> TYPE: DNA
<213> ORGANISM: Artificial Sequence
<220> FEATURE:
<223> OTHER INFORMATION: Synthetic

<400> SEQUENCE: 150
gtctgaggca gttgaga                                                    17

<210> SEQ ID NO 151
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(16)
<220> FEATURE:
<221> NAME/KEY: misc_feature
<222> LOCATION: (15)..(16)
<223> OTHER INFORMATION: n is a phosphoramidite

<400> SEQUENCE: 151
gatctcgaac attccn                                                     16

<210> SEQ ID NO 152
<211> LENGTH: 16
<212> TYPE: DNA
<213> ORGANISM: Artificial Sequence
<220> FEATURE:
<223> OTHER INFORMATION: Synthetic

<400> SEQUENCE: 152
taagtctgaa gatcca                                                     16

<210> SEQ ID NO 153
<211> LENGTH: 31
<212> TYPE: DNA
<213> ORGANISM: Artificial Sequence
<220> FEATURE:
<223> OTHER INFORMATION: Synthetic

<400> SEQUENCE: 153
```
tttatcacca gctgctgcac gccatagtag a                                        31

<210> SEQ ID NO 154
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(15)
<223> OTHER INFORMATION: n is a phosphoramidite

<400> SEQUENCE: 154
cgtatcacct gtccn                                                         15

<210> SEQ ID NO 155
<211> LENGTH: 17
<212> TYPE: DNA
<213> ORGANISM: Artificial Sequence
<220> FEATURE:
<223> OTHER INFORMATION: Synthetic

<400> SEQUENCE: 155
agctacttgc tacacga                                                       17

<210> SEQ ID NO 156
<211> LENGTH: 31
<212> TYPE: DNA
<213> ORGANISM: Artificial Sequence
<220> FEATURE:
<223> OTHER INFORMATION: Synthetic

<400> SEQUENCE: 156
ggatcttcag acttaggaat gttcgagatc a                                       31

<210> SEQ ID NO 157
<211> LENGTH: 31
<212> TYPE: DNA
<213> ORGANISM: Artificial Sequence
<220> FEATURE:
<223> OTHER INFORMATION: Synthetic

<400> SEQUENCE: 157
catgcgagga ctcggtccaa taccgtacta a                                       31

<210> SEQ ID NO 158
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(15)
<223> OTHER INFORMATION: n is a phosphoramidite

<400> SEQUENCE: 158
cgattacaga tcaan                                                         15

<210> SEQ ID NO 159
<211> LENGTH: 15
<212> TYPE: DNA
<213> ORGANISM: Artificial Sequence
<220> FEATURE:
<223> OTHER INFORMATION: Synthetic -continued

```
<400> SEQUENCE: 159
cagctggtga taaaa                                                  15

<210> SEQ ID NO 160
<211> LENGTH: 31
<212> TYPE: DNA
<213> ORGANISM: Artificial Sequence
<220> FEATURE:
<223> OTHER INFORMATION: Synthetic

<400> SEQUENCE: 160
cgtgtagcaa gtagctttga tctgtaatcg a                                31

<210> SEQ ID NO 161
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(16)
<223> OTHER INFORMATION: n is a phosphoramidite

<400> SEQUENCE: 161
ctctacggga agagcn                                                 16

<210> SEQ ID NO 162
<211> LENGTH: 16
<212> TYPE: DNA
<213> ORGANISM: Artificial Sequence
<220> FEATURE:
<223> OTHER INFORMATION: Synthetic

<400> SEQUENCE: 162
atgcccatcc ggctca                                                 16

<210> SEQ ID NO 163
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(17)
<223> OTHER INFORMATION: n is a phosphoramidite

<400> SEQUENCE: 163
ctactatggc gtgcagn                                                17

<210> SEQ ID NO 164
<211> LENGTH: 15
<212> TYPE: DNA
<213> ORGANISM: Artificial Sequence
<220> FEATURE:
<223> OTHER INFORMATION: Synthetic

<400> SEQUENCE: 164
cgagtcctcg catga                                                  15

<210> SEQ ID NO 165
<211> LENGTH: 31
<212> TYPE: DNA
<213> ORGANISM: Artificial Sequence
<220> FEATURE:
<223> OTHER INFORMATION: Synthetic
```

-continued

<400> SEQUENCE: 165
ctcaactgcc tcagacggac aggtgatacg a                               31

<210> SEQ ID NO 166
<211> LENGTH: 31
<212> TYPE: DNA
<213> ORGANISM: Artificial Sequence
<220> FEATURE:
<223> OTHER INFORMATION: Synthetic

<400> SEQUENCE: 166
gagccggatg ggcatgctct tcccgtagag a                               31

<210> SEQ ID NO 167
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(17)
<223> OTHER INFORMATION: n is a phosphoramidite

<400> SEQUENCE: 167
cggtattgga catgatn                                               17

<210> SEQ ID NO 168
<211> LENGTH: 80
<212> TYPE: DNA
<213> ORGANISM: Artificial Sequence
<220> FEATURE:
<223> OTHER INFORMATION: Synthetic

<400> SEQUENCE: 168
cccgcagatg actaattttt tttttacatt cctaagtctg aaacattaca gcttgctaca    60
cgagaagagc cgccatagta                                           80

<210> SEQ ID NO 169
<211> LENGTH: 55
<212> TYPE: DNA
<213> ORGANISM: Artificial Sequence
<220> FEATURE:
<223> OTHER INFORMATION: Synthetic

<400> SEQUENCE: 169
tatcaccagg cagttgacag tgtagcaagc tgtaatagat gcgagggtcc aatac          55

<210> SEQ ID NO 170
<211> LENGTH: 55
<212> TYPE: DNA
<213> ORGANISM: Artificial Sequence
<220> FEATURE:
<223> OTHER INFORMATION: Synthetic

<400> SEQUENCE: 170
tcaactgcct ggtgataaaa cgacactacg tgggaatcta ctatggcggc tcttc          55

<210> SEQ ID NO 171
<211> LENGTH: 55
<212> TYPE: DNA
<213> ORGANISM: Artificial Sequence
<220> FEATURE:
<223> OTHER INFORMATION: Synthetic -continued

```
<400> SEQUENCE: 171
ttcagactta ggaatgtgct tcccacgtag tgtcgtttgt attggaccct cgcat                 55

<210> SEQ ID NO 172
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(24)
<223> OTHER INFORMATION: n is a phosphoramidite

<400> SEQUENCE: 172
aaaatacgcc gtaaatttgc gggn                                                    24

<210> SEQ ID NO 173
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 173
aacgcatatg caaaaacata aagcatatgc ga                                          32

<210> SEQ ID NO 174
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 174
ttggtggtgg tggttgtggt ggtggtggt                                              29
```